(12) United States Patent
Hernandez et al.

(10) Patent No.: US 8,742,097 B2
(45) Date of Patent: Jun. 3, 2014

(54) TRIAZOLE COMPOUNDS I

(75) Inventors: Maria-Clemencia Hernandez, Delemont (CH); Matthew C. Lucas, Verona, NJ (US); Andrew Thomas, Binningen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 77 days.

(21) Appl. No.: 13/287,149

(22) Filed: Nov. 2, 2011

(65) Prior Publication Data

US 2012/0115844 A1 May 10, 2012

(30) Foreign Application Priority Data

Nov. 9, 2010 (EP) ..................................... 10190415

(51) Int. Cl.
| | | |
|---|---|---|
| C07D 401/12 | (2006.01) | |
| C07D 403/10 | (2006.01) | |
| C07D 403/12 | (2006.01) | |
| C07D 403/14 | (2006.01) | |
| C07D 405/14 | (2006.01) | |
| C07D 409/14 | (2006.01) | |
| C07D 413/14 | (2006.01) | |
| C07D 471/04 | (2006.01) | |
| C07D 491/107 | (2006.01) | |

(52) U.S. Cl.
CPC ............ *C07D 401/12* (2013.01); *C07D 403/10* (2013.01); *C07D 403/12* (2013.01); *C07D 403/14* (2013.01); *C07D 405/14* (2013.01); *C07D 409/14* (2013.01); *C07D 413/14* (2013.01); *C07D 471/04* (2013.01); *C07D 491/107* (2013.01)
USPC ........... 544/114; 544/120; 544/131; 544/238; 544/405; 546/256; 546/268.4

(58) Field of Classification Search
USPC .......................................... 514/359; 548/255
See application file for complete search history.

(56) References Cited

U.S. PATENT DOCUMENTS 8,106,077 B2 * 1/2012 Bell et al. ...................... 514/359

FOREIGN PATENT DOCUMENTS

| WO | 2007/140174 | 6/2007 | |
|---|---|---|---|
| WO | WO 2007/140174 | * | 12/2007 |
| WO | 2009/154300 | 12/2009 | |

OTHER PUBLICATIONS

McKernan et al., "Recombinant Cell Surface Receptors: Focal Point for Therapeutic Intervention, M. J. Browne (Ed.)" ((R. G. Landes Co., Austin, Texas)), 18:155-173 ( 1997).
Solis-Anez et al., "Investigacion Clinica" 48:529-541 ( 2007).
Cui et al., "Cell" 135:549-560 ( 2008).
Papadimitriou et al., "Neuropsychobiology" 43(3):141-144 ( 2001).
Fernandez et al., "Nature Neuroscience" 10:411-413 ( 2007).
Oyama, S., "Psychobiology" 21(1):101-105 ( 1988).
Delong, R., "Autism" 11(2):135-147 ( 2007).
Otani et al., "Neuroscience Letters" 381:108-113 ( 2005).
"International Search Report—PCT/EP2011/069496 mailed Jan. 12, 2012".
Rueda et al., "Neuroscience Letters" 433:22-27 ( 2008).
McCauley et al., "Amer. J. Med. Genetics" 131B:51-59 ( 2004).

* cited by examiner

*Primary Examiner* — Alicia L Otton

(57) ABSTRACT

The present invention is concerned with novel triazole compounds of formula (I)

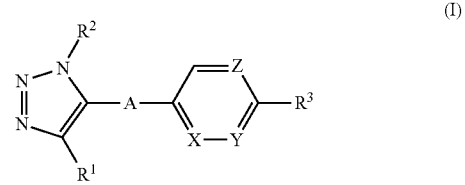

(I)

wherein A, X, Y, Z, $R^1$, $R^2$, and $R^3$ are as described herein, as well as pharmaceutically acceptable salts and esters thereof. The active compounds of present invention have affinity and selectivity for the GABA A α5 receptor. Further the present invention is concerned with the manufacture of the compounds of formula (I), pharmaceutical compositions comprising them and their use as medicaments.

19 Claims, No Drawings

TRIAZOLE COMPOUNDS I

PRIORITY TO RELATED APPLICATION(S)

This application claims the benefit of European Patent Application No. 10190415.9, filed Nov. 9, 2010, which is hereby incorporated by reference in its entirety.

BACKGROUND OF THE INVENTION

Receptors for the major inhibitory neurotransmitter, gamma-aminobutyric acid (GABA), are divided into two main classes: (1) GABA A receptors, which are members of the ligand-gated ion channel superfamily and (2) GABA B receptors, which are members of the G-protein linked receptor family. The GABA A receptor complex which is a membrane-bound heteropentameric protein polymer is composed principally of α, β and γ subunits. Presently a total number of 21 subunits of the GABA A receptor have been cloned and sequenced. Three types of subunits (α, β and γ) are required for the construction of recombinant GABA A receptors which most closely mimic the biochemical, electrophysiological and pharmacological functions of native GABA A receptors obtained from mammalian brain cells. There is strong evidence that the benzodiazepine binding site lies between the α and γ subunits. Among the recombinant GABA A receptors, α1β2γ2 mimics many effects of the classical type-I benzodiazepine receptor (BzR) subtypes, whereas α2β2γ2, α3β2γ2 and α5β2γ2 ion channels are termed type-II BzR (R. M. McKernan, P. J. Whiting, in Recombinant Cell Surface Receptors: Focal Point for Therapeutic Intervention, M. J. Browne (Ed.) (1997) Chapter 8:155-173, R.G. Landes Co., Austin, Tex.).

It has been shown by McNamara and Skelton (Psychobiology (1993) 21:101-108) that the benzodiazepine receptor inverse agonist β-CCM enhance spatial learning in the Morris watermaze. However, β-CCM and other conventional benzodiazepine receptor inverse agonists are proconvulsant or convulsant which prevents their use as cognition enhancing agents in humans. In addition, these compounds are non-selective within the GABA A receptor subunits, whereas a GABA A α5 receptor partial or full inverse agonist which is relatively free of activity at GABA A α1 and/or α2 and/or α3 receptor binding sites can be used to provide a medicament which is useful for enhancing cognition with reduced or without proconvulsant activity. It is also possible to use GABA A α5 inverse agonists which are not free of activity at GABA A α1 and/or α2 and/or α3 receptor binding sites but which are functionally selective for α5 containing subunits. However, inverse agonists which are selective for GABA A α5 subunits and are relatively free of activity at GABA A α1, α2 and α3 receptor binding sites are preferred.

Literature has been published to establish the link between GABA A α5 subunits and the treatment of various diseases of the Central Nervous System (Neuroscience Letts. (2005) 381: 108-13, Neuropsychobiology (2001) 43 (3):141-44, Amer. J. Med. Genetics (2004) 131B:51-9, Autism (2007) 11 (2):135-47, Investigacion Clinica (2007) 48:529-41, Nature Neuroscience (2007) 10:411-13, Neuroscience Letts. (2008) 433: 22-7, Cell (2008) 135:549-60).

SUMMARY OF THE INVENTION

The present invention provides triazole compounds having affinity and selectivity for the GABA A α5 receptor, their manufacture, pharmaceutical compositions containing them and their use as pharmaceuticals.

The present invention is related to compounds of formula (I)

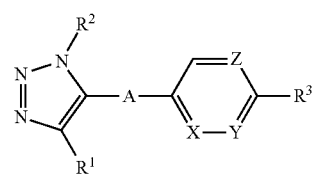

wherein A, X, Y, Z, $R^1$, $R^2$ and $R^3$ are as described below and in the claims, and pharmaceutically acceptable salts and esters thereof.

The present invention provides compounds of formula I and their pharmaceutically acceptable salts and esters, preparation of the above mentioned compounds, pharmaceutical compositions containing them and their manufacture as well as use of the above mentioned compounds in the treatment or prevention of diseases related to the GABA A α5 receptor. The compounds of present invention are preferably inverse agonists of GABA A α5.

The compounds of present invention and their pharmaceutically acceptable salts and esters have high affinity and selectivity for the GABA A α5 receptor and can be used, alone or in combination with other drugs, as cognitive enhancers or for the treatment or prevention of acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders.

DETAILED DESCRIPTION OF THE INVENTION

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below.

The nomenclature used in this Application is based on IUPAC systematic nomenclature, unless indicated otherwise.

Any open valency appearing on a carbon, oxygen, sulfur or nitrogen atom in the structures herein indicates the presence of a hydrogen, unless indicated otherwise.

The definitions described herein apply irrespective of whether the terms in question appear alone or in combination. It is contemplated that the definitions described herein may be appended to form chemically-relevant combinations, such as e.g. "heterocycloalkyl-aryl", "haloalkyl-heteroaryl", "aryl-alkyl-heterocycloalkyl", or "alkoxy-alkyl". The last member of the combination is a radical which is substituted by the other members of the combination in inverse order.

When indicating the number of substituents, the term "one or more" refers to the range from one substituent to the highest possible number of substitution, i.e. replacement of one hydrogen up to replacement of all hydrogens by substituents.

The term "optional" or "optionally" denotes that a subsequently described event or circumstance may, but need not, occur and that the description includes instances where the event or circumstance occurs and instances in which it does not.

The term "substituent" denotes an atom or a group of atoms replacing a hydrogen atom on the parent molecule.

The term "substituted" denotes that a specified group bears one or more substituents. Where any group can carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents.

The term "compound(s) of this invention" and "compound(s) of the present invention" refers to compounds of formula (I) and stereoisomers, tautomers, solvates, and salts (e.g., pharmaceutically acceptable salts) thereof.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable esters" denotes derivatives of the compounds of present invention, in which a carboxy group has been converted to an ester. Alkyl, hydroxyalkyl, alkoxy-alkyl, amino-alkyl, cycloalkyl-alkyl, heterocycloalkyl-alkyl, heteroaryl-alkyl, and aryl-alkyl esters are examples of suitable esters. The term "pharmaceutically acceptable esters" furthermore embraces derivatives of the compounds of present invention in which hydroxy groups have been converted to the corresponding esters with inorganic or organic acids such as nitric acid, sulfuric acid, phosphoric acid, citric acid, formic acid, maleic acid, acetic acid, succinic acid, tartaric acid, methanesulfonic acid, or p-toluenesulfonic acid, which are non toxic to living organisms.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

The term "solvate" denotes crystal forms having either stoichiometric or nonstoichiometric amounts of a solvent incorporated in the crystal lattice. If the incorporated solvent is water, the solvate formed is a hydrate. When the incorporated solvent is alcohol, the solvate formed is an alcoholate.

The term "stereoisomer" denotes a compound that possesses identical molecular connectivity and bond multiplicity, but which differs in the arrangement of its atoms in space.

The term "halo," "halogen," and "halide" are used interchangeably herein and denote fluoro, chloro, bromo, or iodo. Particular examples of halo are fluoro and chloro.

The term "alkyl" denotes a monovalent linear or branched saturated hydrocarbon group of 1 to 12 carbon atoms, in particular of 1 to 7 carbon atoms, more particular of 1 to 4 carbon atoms, for example, methyl, ethyl, propyl, isopropyl, n-butyl, iso-butyl, sec-butyl, or tert-butyl. Particular examples of alkyl are methyl, ethyl, n-propyl, isopropyl and tert-butyl, particularly methyl and iso-propyl.

The term "alkoxy" denotes a group of the formula —O—R', wherein R' is an alkyl group. Examples of alkoxy moieties include methoxy, ethoxy, isopropoxy, and tert-butoxy. Particular examples of alkoxy are methoxy and ethoxy.

The term "haloalkyl" denotes an alkyl group wherein at least one of the hydrogen atoms of the alkyl group has been replaced by same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl. The term "perhaloalkyl" denotes an alkyl group where all hydrogen atoms of the alkyl group have been replaced by the same or different halogen atoms.

The term "hydroxyalkyl" denotes an alkyl group wherein at least one of the hydrogen atoms of the alkyl group has been replaced by a hydroxy group. Examples of hydroxyalkyl include hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl or 2-(hydroxymethyl)-3-hydroxypropyl. Particular examples of hydroxyalkyl are hydroxy-ethyl and hydroxy-tert-butyl, particularly hydroxy-tert-butyl.

The term "halohydroxyalkyl" denotes an alkyl group wherein at least one of the hydrogen atoms of the alkyl group has been replaced by a halo group and at least one further of the hydrogen atoms of the alkyl group has been replaced by a hydroxy group. Examples of hydroxyalkyl include 3,3,3-trifluoro-2-hydroxy-propyl.

The term "cycloalkyl" denotes a monovalent saturated monocyclic or bicyclic hydrocarbon group of 3 to 10 ring carbon atoms, particularly a monovalent saturated monocyclic hydrocarbon group of 3 to 8 ring carbon atoms. Bicyclic means consisting of two saturated carbocycles having two carbon atoms in common, i.e. the bridge separating the two rings is either a single bond or a chain of one or two carbon atoms. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl, bicyclo[2.2.2]octanyl or adamantanyl. A particular example of cycloalkyl includes cyclopropyl.

The term "cycloalkylalkyl" denotes an alkyl group wherein at least one of the hydrogen atoms of the alkyl group is replaced by a cycloalkyl group. Examples of cycloalkylalkyl include cyclopropylmethyl, cyclopropylethyl, cyclobutylpropyl and cyclopentylbutyl. A particular example of cycloalkyl includes cyclopropylmethyl.

The term "heterocycloalkyl" denotes a monovalent saturated or partly unsaturated mono- or bicyclic ring system of 4 to 9 ring atoms, comprising 1, 2, or 3 ring heteroatoms selected from N, O and S, the remaining ring atoms being carbon. Bicyclic means consisting of two rings having two ring atoms in common, i.e. the bridge separating the two rings is either a single bond or a chain of one or two ring atoms. Examples for monocyclic saturated heterocycloalkyl are azetidinyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, or dihydropyranyl. Particular examples of heterocycloalkyl include oxetanyl, oxetanyl substituted by methyl, tetrahydro-1,6-thiophenyl, 1,1-dioxo-tetrahydro-1,6-thiophenyl, tetrahydro-pyranyl, morpholinyl, thiomorpholinyl, dioxo-thiomorpholinyl, and 2-oxa-6-azaspiro[3.3]heptanyl. Particular examples of heterocycloalkyl include oxetanyl substituted by methyl, tetrahydro-pyranyl, and morpholinyl.

The term "aryl" denotes a monovalent aromatic carbocyclic mono- or bicyclic ring system comprising 6 to 10 carbon ring atoms. Examples of aryl moieties include phenyl and naphthyl. A particular example of aryl includes phenyl.

The term "aryloxy" denotes a group of the formula —O—R', wherein R' is aryl. An example of aryloxy is phenoxy.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, quinoxalinyl, carbazolyl, or acridinyl. A particular example of heteroaryl includes pyridinyl.

The term "alkylene" denotes a linear saturated divalent hydrocarbon group of 1 to 7 carbon atoms or a divalent branched saturated divalent hydrocarbon group of 3 to 7 carbon atoms. Examples of alkylene groups include methylene, ethylene, propylene, 2-methylpropylene, butylene, 2-ethylbutylene, pentylene, hexylene. A particular example of alkylene includes methylene.

The term "amino" denotes a group of the formula —NR'R" wherein R' and R" are independently hydrogen, alkyl, alkoxy, cycloalkyl, heterocycloalkyl, aryl or heteroaryl. Alternatively, R' and R", together with the nitrogen to which they are attached, can form a heterocycloalkyl. The term "primary amino" denotes a group wherein both R' and R" are hydrogen. The term "secondary amino" denotes a group wherein R' is hydrogen and R" is not. The term "tertiary amino" denotes a group wherein both R' and R" are not hydrogen. Particular secondary and tertiary amines are methylamine, ethylamine, propylamine, isopropylamine, phenylamine, benzylamine, dimethylamine, diethylamine, dipropylamine and diisopropylamine. A particular example of amino includes dimethylamine.

The term "active pharmaceutical ingredient" (or "API") denotes the compound in a pharmaceutical composition that has a particular biological activity.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

The term "pharmaceutical composition" (or "composition") denotes a mixture or solution comprising a therapeutically effective amount of an active pharmaceutical ingredient together with pharmaceutically acceptable excipients to be administered to a mammal, e.g., a human in need thereof.

The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values (−log Ki), in which higher values indicate exponentially greater potency.

The term "therapeutically effective amount" denotes an amount of a compound of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, disease state being treated, the severity or the disease treated, the age and relative health of the subject, the route and form of administration, the judgement of the attending medical or veterinary practitioner, and other factors.

The term "treating" or "treatment" of a disease state includes (1) preventing the disease state, i.e. causing the clinical symptoms of the disease state not to develop in a subject that may be exposed to or predisposed to the disease state, but does not yet experience or display symptoms of the disease state, (2) inhibiting the disease state, i.e., arresting the development of the disease state or its clinical symptoms, or (3) relieving the disease state, i.e., causing temporary or permanent regression of the disease state or its clinical symptoms.

The term "subject" denotes a vertebrate. In certain embodiments, the vertebrate is a mammal. Mammals include humans, non-human primates such as chimpanzees and other apes and monkey species, farm animals such as cattle, horses, sheep, goats, and swine, domestic animals such as rabbits, dogs, and cats, laboratory animals including rodents, such as rats, mice, and guinea pigs. In certain embodiments, a mammal is a human. The term subject does not denote a particular age or sex.

In particular, the present invention provides compounds of formula (I)

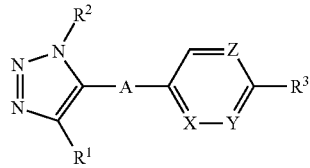

(I)

wherein
A is —CH$_2$—O—, —CH═CH— or —C≡C—;
X is N or CH;
Y is N or CR$^9$;
Z is N or CR$^{10}$;
R$^1$ and R$^2$ are each independently alkyl, aryl optionally substituted by one halo or heteroaryl optionally substituted by one halo, wherein one of R$^1$ or R$^2$ is alkyl;
R$^3$ is halo, cyano, haloalkyl, —C(O)R$^4$, or —C(O)NR$^5$R$^6$;
R$^4$ is H, hydroxy, alkoxy or aryloxy;
R$^5$ is H, alkyl, haloalkyl, hydroxyalkyl, halohydroxyalkyl, —(CH$_2$)$_n$-cycloalkyl, —(CH$_2$)$_n$-heterocycloalkyl, or —(CH$_2$)$_n$—NR$^7$R$^8$, wherein cycloalkyl and heterocycloalkyl are optionally substituted by one or more halo, alkyl, haloalkyl, hydroxyalkyl, alkoxy, or oxo;
R$^6$ is H, alkyl, or is alkylene together with R$^9$ or R$^{10}$;
or R$^5$ and R$^6$ together with the nitrogen to which they are bound form a heterocycloalkyl optionally substituted by one or more oxo;
R$^7$ and R$^8$ are each independently H, alkyl, or aryl;
R$^9$ and R$^{10}$ are each independently H, or one of R$^9$ or R$^{10}$ is alkylene together with R$^6$; and
n is an integer from 0 to 6;
and pharmaceutically acceptable salts and esters thereof.

Particular embodiments of present invention are compounds of formula (I) and pharmaceutically acceptable salts thereof and pharmaceutically acceptable esters thereof.

A particular embodiment of invention is concerned with compounds of formula (I), wherein
A is —CH$_2$—O—, —CH═CH— or —C≡C—;
X is N or CH;
Y is N or CR$^9$;
Z is N or CR$^{10}$;
R$^1$ and R$^2$ are each independently alkyl, aryl optionally substituted by one halo or heteroaryl optionally substituted by one halo, wherein one of R$^1$ or R$^2$ is alkyl;
R$^3$ is halo, —C(O)R$^4$, or —C(O)NR$^5$R$^6$;
R$^4$ is alkoxy;
R$^5$ is alkyl, haloalkyl, hydroxyalkyl, halohydroxyalkyl, —(CH$_2$)$_n$-cycloalkyl, —(CH$_2$)$_n$-heterocycloalkyl, or —(CH$_2$)$_n$—NR$^7$R$^8$, wherein heterocycloalkyl is optionally substituted by one or two alkyl or oxo;
R$^6$ is H, or is alkylene together with R$^9$, R$^{10}$;
or R$^5$ and R$^6$ together with the nitrogen to which they are bound form a heterocycloalkyl optionally substituted by one or two oxo;
R$^7$ and R$^8$ are each independently alkyl;
R$^9$ and R$^{10}$ are each independently H, or one of R$^9$ or R$^{10}$ is alkylene together with R$^6$; and
n is an integer from 0 to 1;
and pharmaceutically acceptable salts and esters thereof.

Further, it is to be understood that every embodiment relating to a specific residue A, X, Y, Z, R$^1$, R$^2$, R$^3$, R$^4$, R$^5$, R$^6$, R$^7$, R$^8$, R$^9$ or R$^{10}$ as disclosed herein can be combined with any other embodiment relating to another residue A, X, Y, Z, R$^1$, R$^2$, R$^3$, R$^4$, R$^5$, R$^6$, R$^7$, R$^8$, R$^9$ or R$^{10}$ as disclosed herein.

In a particular embodiment of the invention, A is bound to the triazole ring via a carbon atom.

In a particular embodiment of the invention, A is —CH$_2$—O—.

In a particular embodiment of the invention, at least one of X or Y is N.

In a particular embodiment of the invention, X is N, Y is CR$^9$ and Z is CR$^{10}$; or X is CH, Y is N and Z is CR$^{10}$; or X is N, Y is CR$^9$ and Z is N; or X is N, Y is N and Z is CR$^{10}$.

In a particular embodiment of the invention, X, Y and Z together with the carbon atoms to which they are bound form a heteroaryl selected from pyrazinyl, pyridazinyl, and pyridinyl, more particularly pyrazinyl and pyridinyl.

A particular embodiment of the invention relates to compounds of formula (Ia)

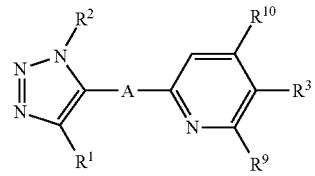

(Ia)

wherein A, R$^1$, R$^2$, R$^3$, R$^9$ and R$^{10}$ are as defined above.

A particular embodiment of the invention relates to compounds of formula (Ib)

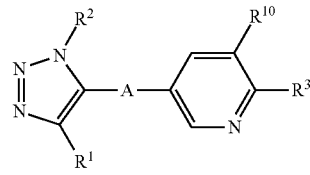

(Ib)

wherein A, R$^1$, R$^2$, R$^3$, and R$^{10}$ are as defined above.

A particular embodiment of the invention relates to compounds of formula (Ic)

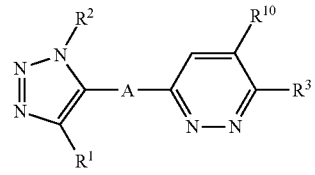

(Ic)

wherein A, R$^1$, R$^2$, R$^3$ and R$^{10}$ are as defined above.

A particular embodiment of the invention relates to compounds of formula (Id)

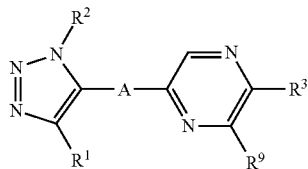

wherein A, $R^1$, $R^2$, $R^3$ and $R^9$ are as defined above.

A particular embodiment of the invention relates to compounds of formula (I')

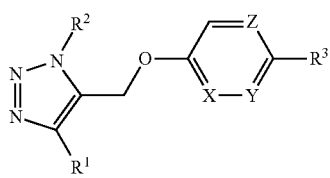

wherein X, Y, Z, $R^1$, $R^2$ and $R^3$ are as defined above.

A particular embodiment of the invention relates to compounds of formula (I")

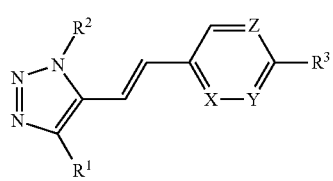

wherein X, Y, Z, $R^1$, $R^2$ and $R^3$ are as defined above.

A particular embodiment of the invention relates to compounds of formula (I''')

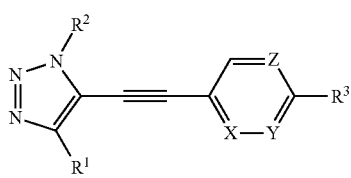

wherein X, Y, Z, $R^1$, $R^2$ and $R^3$ are as defined above.

In a particular embodiment of the invention, one of $R^1$ and $R^2$ is alkyl, and the other one is aryl optionally substituted by one halo or heteroaryl optionally substituted by one halo.

In a particular embodiment of the invention, one of $R^1$ and $R^2$ is methyl, ethyl or butyl, and the other one is phenyl optionally substituted by one halo, or pyridinyl optionally substituted by one halo.

In a particular embodiment of the invention, one of $R^1$ and $R^2$ is methyl, and the other one is phenyl, phenyl substituted by one fluoro, pyridinyl, or pyridinyl substituted by one fluoro.

In a particular embodiment of the invention, one of $R^1$ and $R^2$ is methyl, and the other one is phenyl, phenyl substituted by one fluoro in ortho or para position, pyridinyl, or pyridinyl substituted by one fluoro.

In a particular embodiment of the invention, $R^1$ is alkyl; and $R^2$ is aryl, or aryl substituted by one halo.

In a particular embodiment of the invention, $R^1$ is methyl; and $R^2$ is phenyl, or phenyl substituted by one fluoro, most particularly in para position.

In a particular embodiment of the invention, $R^1$ is methyl; and $R^2$ is phenyl, 2-fluoro-phenyl, or 4-fluoro-phenyl.

In a particular embodiment of the invention, $R^2$ is alkyl; and $R^1$ is aryl, aryl substituted by one halo, heteroaryl, or heteroaryl substituted by one halo.

In a particular embodiment of the invention, $R^2$ is methyl; and $R^1$ is phenyl, phenyl substituted by one fluoro, most particularly in para position, pyridinyl, or pyridinyl substituted by one fluoro.

In a particular embodiment of the invention, $R^2$ is methyl; and $R^1$ is phenyl, 2-fluoro-phenyl, 4-fluoro-phenyl, pyridin-2-yl, or 5-fluoro-pyridin-2-yl.

In a particular embodiment of the invention, $R^3$ is halo, —C(O)$R^4$, or —C(O)N$R^5R^6$.

In a particular embodiment of the invention, $R^3$ is Cl, —C(O)$R^4$, or —C(O)N$R^5R^6$.

In a particular embodiment of the invention, $R^3$ is —C(O)N$R^5R^6$.

In a particular embodiment of the invention, $R^3$ is —C(O)$R^4$.

In a particular embodiment of the invention, $R^4$ is unsubstituted alkoxy, particularly methoxy or ethoxy.

In a particular embodiment of the invention, $R^3$ is —C(O)$R^4$ and $R^4$ is alkoxy.

In a particular embodiment of the invention, $R^5$ is alkyl, haloalkyl, hydroxyalkyl, halohydroxyalkyl, cycloalkylalkyl, cycloalkyl, heterocycloalkyl, heterocycloalkyl substituted by alkyl, or N$R^7R^8$.

In a particular embodiment of the invention, $R^5$ is isopropyl, trifluoro-ethyl, hydroxy-ethyl, 2-hydroxy-1,1-dimethyl-ethyl, 3,3,3-trifluoro-2-hydroxy-propyl, cyclopropylmethyl, cyclopropyl, methyl-oxetanyl, dioxo-tetrahydro-thiophenyl, tetrahydro-pyranyl, morpholinyl, or N(CH$_3$)$_2$.

In a particular embodiment of the invention, $R^6$ is H.

In a particular embodiment of the invention, $R^5$ and $R^6$ together with the nitrogen to which they are bound form a heterocycloalkyl optionally substituted by one or more oxo.

In a particular embodiment of the invention, $R^5$ and $R^6$ together with the nitrogen to which they are bound form dioxo-thiomorpholinyl and 2-oxa-6-azaspiro[3.3]heptan-6-yl.

In a particular embodiment of the invention, $R^7$ and $R^8$ are both alkyl, particularly methyl.

In a particular embodiment of the invention, $R^9$ is H.

In a particular embodiment of the invention, $R^{10}$ is H.

In a particular embodiment of the invention, $R^6$ together with $R^{10}$ is alkylene, particularly methylene.

A particular embodiment of the present invention relates to compounds of formula (I) as described in the examples as individual compounds as well as pharmaceutically acceptable salts as well as pharmaceutically acceptable esters thereof. Furthermore, the substituents as found in the specific examples described below, individually constitute separate particular embodiments of the present invention.

Particular compounds of formula (I) of present invention are those selected from the group consisting of:

N-Isopropyl-6-(3-methyl-5-phenyl-3H-[1,2,3]triazol-4-ylmethoxy)-nicotinamide;
6-(3-Methyl-5-phenyl-3H-[1,2,3]triazol-4-ylmethoxy)-N-(tetrahydro-pyran-4-yl)-nicotinamide;
6-(3-Methyl-5-phenyl-3H-[1,2,3]triazol-4-ylmethoxy)-N-morpholin-4-yl-nicotinamide;
N-Cyclopropyl-6-(3-methyl-5-phenyl-3H-[1,2,3]triazol-4-ylmethoxy)-nicotinamide;
N-Cyclopropylmethyl-6-(3-methyl-5-phenyl-3H-[1,2,3]triazol-4-ylmethoxy)-nicotinamide;
N-(1,1-Dioxo-tetrahydro-1,6-thiophen-3-yl)-6-(3-methyl-5-phenyl-3H-[1,2,3]triazol-4-ylmethoxy)-nicotinamide;
6-(3-Methyl-5-phenyl-3H-[1,2,3]triazol-4-ylmethoxy)-N-(2,2,2-trifluoro-ethyl)-nicotinamide;
N-(2-Hydroxy-ethyl)-6-(3-methyl-5-phenyl-3H-[1,2,3]triazol-4-ylmethoxy)-nicotinamide;
6-[5-(4-Fluoro-phenyl)-3-methyl-3H-[1,2,3]triazol-4-ylmethoxy]-nicotinic acid methyl ester;
6-[5-(4-Fluoro-phenyl)-3-methyl-3H-[1,2,3]triazol-4-ylmethoxy]-N-(tetrahydro-pyran-4-yl)-nicotinamide;
6-[5-(4-Fluoro-phenyl)-3-methyl-3H-[1,2,3]triazol-4-ylmethoxy]-N-isopropyl-nicotinamide;
6-[5-(4-Fluoro-phenyl)-3-methyl-3H-[1,2,3]triazol-4-ylmethoxy]-N-(2-hydroxy-1,1-dimethyl-ethyl)-nicotinamide;
6-[5-(4-Fluoro-phenyl)-3-methyl-3H-[1,2,3]triazol-4-ylmethoxy]-N-(3-methyl-oxetan-3-yl)-nicotinamide;
6-[5-(4-Fluoro-phenyl)-3-methyl-3H-[1,2,3]triazol-4-ylmethoxy]-N-morpholin-4-yl-nicotinamide;
6-[5-(4-Fluoro-phenyl)-3-methyl-3H-[1,2,3]triazol-4-ylmethoxy]-N-(3,3,3-trifluoro-2-hydroxy-propyl)-nicotinamide;
6-[5-(4-Fluoro-phenyl)-3-methyl-3H-[1,2,3]triazol-4-ylmethoxy]-N-(2-hydroxy-ethyl)-nicotinamide;
6-((4-(4-Fluorophenyl)-1-methyl-1H-1,2,3-triazol-5-yl)methoxy)-2-isopropyl-1H-pyrrolo[3,4-c]pyridin-3(2H)-one;
Methyl 6-((4-(2-fluorophenyl)-1-methyl-1H-1,2,3-triazol-5-yl)methoxy)nicotinate;
6-((4-(2-Fluorophenyl)-1-methyl-1H-1,2,3-triazol-5-yl)methoxy)-N-(tetrahydro-2H-pyran-4-yl)nicotinamide;
6-((4-(2-Fluorophenyl)-1-methyl-1H-1,2,3-triazol-5-yl)methoxy)-N-isopropylnicotinamide;
6-((4-(2-Fluorophenyl)-1-methyl-1H-1,2,3-triazol-5-yl)methoxy)-N-(3-methyloxetan-3-yl)nicotinamide;
(1,1-Dioxo-1,6-thiomorpholin-4-yl)-{6-[5-(2-fluoro-phenyl)-3-methyl-3H-[1,2,3]triazol-4-ylmethoxy]-pyridin-3-yl}-methanone;
(6-((4-(2-Fluorophenyl)-1-methyl-1H-1,2,3-triazol-5-yl)methoxy)pyridin-3-yl)(2-oxa-6-azaspiro[3.3]heptan-6-yl)methanone;
6-((4-(2-Fluorophenyl)-1-methyl-1H-1,2,3-triazol-5-yl)methoxy)-N-morpholinonicotinamide;
6-(3-Methyl-5-pyridin-2-yl-3H-[1,2,3]triazol-4-ylmethoxy)-nicotinic acid methyl ester;
6-(3-Methyl-5-pyridin-2-yl-3H-[1,2,3]triazol-4-ylmethoxy)-N-(tetrahydro-pyran-4-yl)-nicotinamide;
N-Isopropyl-6-(3-methyl-5-pyridin-2-yl-3H-[1,2,3]triazol-4-ylmethoxy)-nicotinamide;
N-(2-Hydroxy-1,1-dimethyl-ethyl)-6-(3-methyl-5-pyridin-2-yl-3H-[1,2,3]triazol-4-ylmethoxy)-nicotinamide;
N-(2-Hydroxy-ethyl)-6-(3-methyl-5-pyridin-2-yl-3H-[1,2,3]triazol-4-ylmethoxy)-nicotinamide;
N-(3-Methyl-oxetan-3-yl)-6-(3-methyl-5-pyridin-2-yl-3H-[1,2,3]triazol-4-ylmethoxy)-nicotinamide;
6-(3-Methyl-5-pyridin-2-yl-3H-[1,2,3]triazol-4-ylmethoxy)-N-morpholin-4-yl-nicotinamide;
6-(3-Methyl-5-pyridin-2-yl-3H-[1,2,3]triazol-4-ylmethoxy)-nicotinic acid N,N'-dimethyl-hydrazide;
6-(3-Methyl-5-pyridin-2-yl-3H-[1,2,3]triazol-4-ylmethoxy)-N-(3,3,3-trifluoro-2-hydroxy-propyl)-nicotinamide;
6-[5-(5-Fluoro-pyridin-2-yl)-3-methyl-3H-[1,2,3]triazol-4-ylmethoxy]-nicotinic acid methyl ester;
6-[5-(5-Fluoro-pyridin-2-yl)-3-methyl-3H-[1,2,3]triazol-4-ylmethoxy]-N-(tetrahydro-pyran-4-yl)-nicotinamide;
6-[5-(5-Fluoro-pyridin-2-yl)-3-methyl-3H-[1,2,3]triazol-4-ylmethoxy]-N-isopropyl-nicotinamide;
6-[5-(5-Fluoro-pyridin-2-yl)-3-methyl-3H-[1,2,3]triazol-4-ylmethoxy]-N-(2-hydroxy-1,1-dimethyl-ethyl)-nicotinamide;
6-[5-(5-Fluoro-pyridin-2-yl)-3-methyl-3H-[1,2,3]triazol-4-ylmethoxy]-N-(3-methyl-oxetan-3-yl)-nicotinamide;
6-[5-(5-Fluoro-pyridin-2-yl)-3-methyl-3H-[1,2,3]triazol-4-ylmethoxy]-N-morpholin-4-yl-nicotinamide;
5-[5-(5-Fluoro-pyridin-2-yl)-3-methyl-3H-[1,2,3]triazol-4-ylmethoxy]-pyridine-2-carboxylic acid isopropylamide;
6-[5-(4-Fluoro-phenyl)-3-methyl-3H-[1,2,3]triazol-4-ylmethoxy]-pyridazine-3-carboxylic acid ethyl ester;
6-[5-(4-Fluoro-phenyl)-3-methyl-3H-[1,2,3]triazol-4-ylmethoxy]-pyridazine-3-carboxylic acid (tetrahydro-pyran-4-yl)-amide;
6-[5-(4-Fluoro-phenyl)-3-methyl-3H-[1,2,3]triazol-4-ylmethoxy]-pyridazine-3-carboxylic acid isopropylamide;
6-[5-(4-Fluoro-phenyl)-3-methyl-3H-[1,2,3]triazol-4-ylmethoxy]-pyridazine-3-carboxylic acid (2-hydroxy-1,1-dimethyl-ethyl)-amide;
6-[5-(4-Fluoro-phenyl)-3-methyl-3H-[1,2,3]triazol-4-ylmethoxy]-pyridazine-3-carboxylic acid morpholin-4-ylamide;
3-Chloro-6-(3-methyl-5-pyridin-2-yl-3H-[1,2,3]triazol-4-ylmethoxy)-pyridazine;
6-(3-Methyl-5-pyridin-2-yl-3H-[1,2,3]triazol-4-ylmethoxy)-pyridazine-3-carboxylic acid ethyl ester;
6-(3-Methyl-5-pyridin-2-yl-3H-[1,2,3]triazol-4-ylmethoxy)-pyridazine-3-carboxylic acid (tetrahydro-pyran-4-yl)-amide;
6-(3-Methyl-5-pyridin-2-yl-3H-[1,2,3]triazol-4-ylmethoxy)-pyridazine-3-carboxylic acid isopropylamide;
3-Chloro-6-[5-(5-fluoro-pyridin-2-yl)-3-methyl-3H-[1,2,3]triazol-4-ylmethoxy]-pyridazine;
6-[5-(5-Fluoro-pyridin-2-yl)-3-methyl-3H-[1,2,3]triazol-4-ylmethoxy]-pyridazine-3-carboxylic acid (2-hydroxy-1,1-dimethyl-ethyl)-amide;
6-[5-(5-Fluoro-pyridin-2-yl)-3-methyl-3H-[1,2,3]triazol-4-ylmethoxy]-pyridazine-3-carboxylic acid morpholin-4-ylamide;
5-[5-(4-Fluoro-phenyl)-3-methyl-3H-[1,2,3]triazol-4-ylmethoxy]-pyrazine-2-carboxylic acid isopropylamide;
5-[5-(4-Fluoro-phenyl)-3-methyl-3H-[1,2,3]triazol-4-ylmethoxy]-pyrazine-2-carboxylic acid (tetrahydro-pyran-4-yl)-amide;
6-{(E)-2-[5-(4-Fluoro-phenyl)-3-methyl-3H-[1,2,3]triazol-4-yl]-vinyl}-nicotinic acid methyl ester;
6-{(E)-2-[5-(4-Fluoro-phenyl)-3-methyl-3H-[1,2,3]triazol-4-yl]-vinyl}-N-isopropyl-nicotinamide;
6-{(E)-2-[5-(4-Fluoro-phenyl)-3-methyl-3H-[1,2,3]triazol-4-yl]-vinyl}-N-(tetrahydro-pyran-4-yl)-nicotinamide;
6-[5-(4-Fluoro-phenyl)-3-methyl-3H-[1,2,3]triazol-4-yl-ethynyl]-N-isopropyl-nicotinamide;
6-[5-(4-Fluoro-phenyl)-3-methyl-3H-[1,2,3]triazol-4-yl-ethynyl]-N-(tetrahydro-pyran-4-yl)-nicotinamide;

6-[3-(4-Fluoro-phenyl)-5-methyl-3H-[1,2,3]triazol-4-yl-methoxy]-nicotinic acid methyl ester;
6-[3-(4-Fluoro-phenyl)-5-methyl-3H-[1,2,3]triazol-4-yl-methoxy]-N-(tetrahydro-pyran-4-yl)-nicotinamide;
6-[3-(4-Fluoro-phenyl)-5-methyl-3H-[1,2,3]triazol-4-yl-methoxy]-N-isopropyl-nicotinamide;
6-[3-(4-Fluoro-phenyl)-5-methyl-3H-[1,2,3]triazol-4-yl-methoxy]-N-(2-hydroxy-1,1-dimethyl-ethyl)-nicotinamide;
6-[3-(4-Fluoro-phenyl)-5-methyl-3H-[1,2,3]triazol-4-yl-methoxy]-N-morpholin-4-yl-nicotinamide;
6-[3-(4-Fluoro-phenyl)-5-methyl-3H-[1,2,3]triazol-4-yl-methoxy]-N-(3-methyl-oxetan-3-yl)-nicotinamide;
Methyl 6-((1-(2-fluorophenyl)-4-methyl-1H-1,2,3-triazol-5-yl)methoxy)nicotinate;
6-((1-(2-Fluorophenyl)-4-methyl-1H-1,2,3-triazol-5-yl)methoxy)-N-isopropylnicotinamide;
6-((1-(2-Fluorophenyl)-4-methyl-1H-1,2,3-triazol-5-yl)methoxy)-N-(tetrahydro-2H-pyran-4-yl)nicotinamide;
6-((1-(2-Fluorophenyl)-4-methyl-1H-1,2,3-triazol-5-yl)methoxy)-N-(3-methyloxetan-3-yl)nicotinamide;
6-((1-(2-Fluorophenyl)-4-methyl-1H-1,2,3-triazol-5-yl)methoxy)-N-morpholinonicotinamide;
N-Cyclopropyl-6-((1-(2-fluorophenyl)-4-methyl-1H-1,2,3-triazol-5-yl)methoxy)nicotinamide;
N-(Cyclopropylmethyl)-6-((1-(2-fluorophenyl)-4-methyl-1H-1,2,3-triazol-5-yl)methoxy)nicotinamide;
3-Chloro-6-[3-(4-fluoro-phenyl)-5-methyl-3H-[1,2,3]triazol-4-ylmethoxy]-pyridazine;
6-[3-(4-Fluoro-phenyl)-5-methyl-3H-[1,2,3]triazol-4-yl-methoxy]-pyridazine-3-carboxylic acid ethyl ester;
6-[3-(4-Fluoro-phenyl)-5-methyl-3H-[1,2,3]triazol-4-yl-methoxy]-pyridazine-3-carboxylic acid isopropylamide;
6-[3-(4-Fluoro-phenyl)-5-methyl-3H-[1,2,3]triazol-4-yl-methoxy]-pyridazine-3-carboxylic acid morpholin-4-ylamide;
6-[3-(4-Fluoro-phenyl)-5-methyl-3H-[1,2,3]triazol-4-yl-methoxy]-pyridazine-3-carboxylic acid (3-methyl-oxetan-3-yl)-amide;
6-[3-(4-Fluoro-phenyl)-5-methyl-3H-[1,2,3]triazol-4-yl-methoxy]-pyridazine-3-carboxylic acid (tetrahydro-pyran-4-yl)-amide;
6-((1-(4-Fluorophenyl)-4-methyl-1H-1,2,3-triazol-5-yl)methoxy)-2-isopropyl-1H-pyrrolo[3,4-c]pyridin-3(2H)-one;
5-[3-(4-Fluoro-phenyl)-5-methyl-3H-[1,2,3]triazol-4-yl-methoxy]-pyrazine-2-carboxylic acid (tetrahydro-pyran-4-yl)-amide;
5-[3-(4-Fluoro-phenyl)-5-methyl-3H-[1,2,3]triazol-4-yl-methoxy]-pyrazine-2-carboxylic acid isopropylamide;
5-[3-(4-Fluoro-phenyl)-5-methyl-3H-[1,2,3]triazol-4-yl-methoxy]-pyrazine-2-carboxylic acid (2-hydroxy-1,1-dimethyl-ethyl)-amide;
5-[3-(4-Fluoro-phenyl)-5-methyl-3H-[1,2,3]triazol-4-yl-methoxy]-pyrazine-2-carboxylic acid morpholin-4-ylamide;
5-[3-(4-Fluoro-phenyl)-5-methyl-3H-[1,2,3]triazol-4-yl-methoxy]-pyrazine-2-carboxylic acid (3-methyl-oxetan-3-yl)-amide; and
pharmaceutically acceptable salts and esters thereof.

Particular compounds of formula (I) of present invention are those selected from the group consisting of:
N-Cyclopropyl-6-(3-methyl-5-phenyl-3H-[1,2,3]triazol-4-ylmethoxy)-nicotinamide;
6-[5-(4-Fluoro-phenyl)-3-methyl-3H-[1,2,3]triazol-4-yl-methoxy]-N-isopropyl-nicotinamide;
6-[5-(4-Fluoro-phenyl)-3-methyl-3H-[1,2,3]triazol-4-yl-methoxy]-N-morpholin-4-yl-nicotinamide;
N-(2-Hydroxy-1,1-dimethyl-ethyl)-6-(3-methyl-5-pyridin-2-yl-3H-[1,2,3]triazol-4-ylmethoxy)-nicotinamide;
6-(3-Methyl-5-pyridin-2-yl-3H-[1,2,3]triazol-4-yl-methoxy)-nicotinic acid N,N'-dimethyl-hydrazide;
6-[5-(5-Fluoro-pyridin-2-yl)-3-methyl-3H-[1,2,3]triazol-4-ylmethoxy]-N-(2-hydroxy-1,1-dimethyl-ethyl)-nicotinamide;
6-[5-(5-Fluoro-pyridin-2-yl)-3-methyl-3H-[1,2,3]triazol-4-ylmethoxy]-N-morpholin-4-yl-nicotinamide;
6-[5-(4-Fluoro-phenyl)-3-methyl-3H-[1,2,3]triazol-4-yl-ethynyl]-N-(tetrahydro-pyran-4-yl)-nicotinamide;
6-[3-(4-Fluoro-phenyl)-5-methyl-3H-[1,2,3]triazol-4-yl-methoxy]-N-(2-hydroxy-1,1-dimethyl-ethyl)-nicotinamide;
6-[3-(4-Fluoro-phenyl)-5-methyl-3H-[1,2,3]triazol-4-yl-methoxy]-N-(3-methyl-oxetan-3-yl)-nicotinamide;
6-((1-(2-Fluorophenyl)-4-methyl-1H-1,2,3-triazol-5-yl)methoxy)-N-(tetrahydro-2H-pyran-4-yl)nicotinamide;
6-((1-(2-Fluorophenyl)-4-methyl-1H-1,2,3-triazol-5-yl)methoxy)-N-(3-methyloxetan-3-yl)nicotinamide; and
pharmaceutically acceptable salts and esters thereof.

The invention further relates to a process for the preparation of compounds of formula (I) as defined above, comprising:

a) the reaction of a compound of formula (II) with a compound of formula (III), wherein $R^a$ is chloro or hydroxy, to give a compound of formula (I') wherein A is —CH$_2$—O—

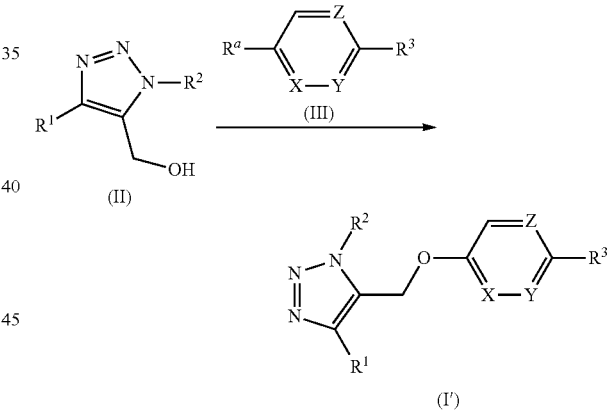

or b) the reaction of a compound of formula (IV) with a compound of formula (V) to give a compound of formula (I") wherein A is —CH=CH—

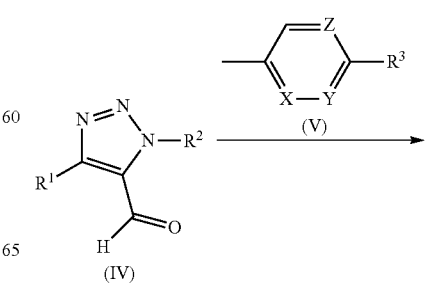

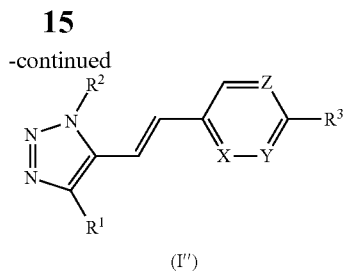

(I″)

or c) the reaction of a compound of formula (VI) with a compound of formula (VII) to give a compound of formula (I‴) wherein A is —CH═CH—

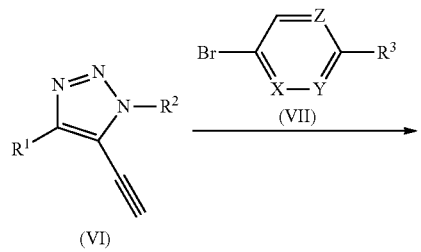

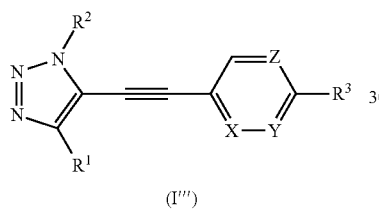

(I‴)

wherein X, Y, Z, $R^1$, $R^2$ and $R^3$ are as defined in any of claims 1 to 10.

The invention further relates to compounds of formula (I) as defined above obtainable by a process as described above.

Compounds of formula (I) can be prepared following standard methods as described below, wherein A, X, Y, Z, $R^1$, $R^2$, $R^3$, $R^4$, $R^5$, and $R^6$ are as described above and in the claims, unless mentioned otherwise.

The present compounds of formula (I') wherein A is —$CH_2$—O— and $R^2$ is alkyl and their pharmaceutically acceptable salts can be prepared in accordance to schemes 1, 2 and 3.

Scheme 1

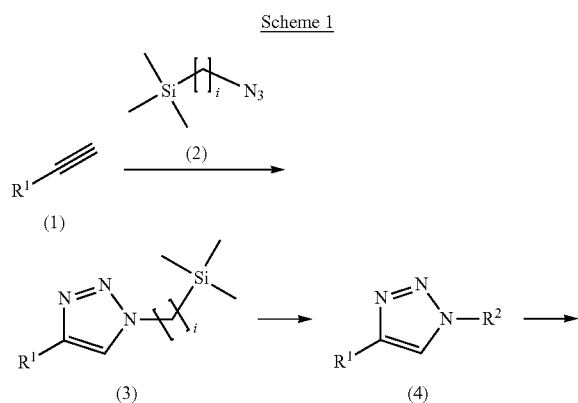

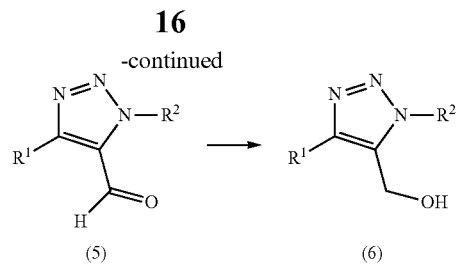

In a first step, a compound of formula (1) is reacted with a compound of formula (2), wherein i is an integer from 1 to 7, particularly 1, in the presence of Cu(I)I in a suitable solvent such as DMF in the presence of a base such as DIPEA to give a compound of formula (3) which can then be treated with TBAF in a suitable solvent such as THF in water to give a compound of formula (4). Alternatively a compound of formula (1) can be treated with Cu(I)I with sodium azide and a compound of formula I$R^2$ in the presence of ascorbic acid under activating conditions such as sonication to give a compound of formula (4). Compounds of formula (4) can then be treated with a strong base such as BuLi in a suitable solvent such as THF and then reacted with DMF to give a compound of formula (5). Treatment of compounds of formula (5) with a reducing agent such as sodiumborohydride in a suitable solvent such as methanol gives a compound of formula (6).

Scheme 2

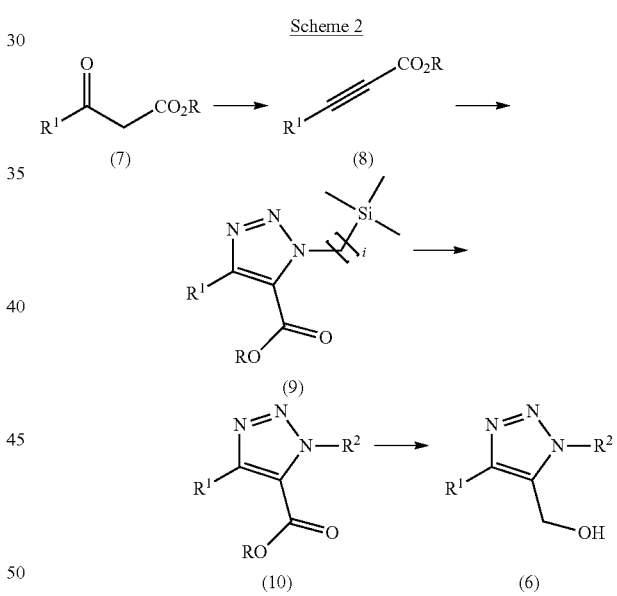

In another instance (Scheme 2) compounds of formula (7), wherein R is alkyl, can be reacted with triphenylphosphine oxide and $Tf_2O$ in the presence of a base such as triethylamine in a suitable solvent such as 1,2-dichloroethane to give a compound of formula (8). Alternatively compounds of formula (1) can be treated with a strong base such as BuLi in the presence of ethyl chloroformate in a suitable solvent to give compounds of formula (8). Compounds of formula (8) can be reacted with a compound of formula (2), wherein i is an integer from 1 to 7, particularly 1, in a suitable solvent such as benzene upon heating to give a compound of formula (9). Compounds of formula (9) can be treated with TBAF in a suitable solvent such as THF in water to give a compound of formula (10) which can be treated with a reducing agent such as lithiumaluminiumhydride in a suitable solvent such as THF to give a compound of formula (6), or ethylchloroformate in the presence of sodiumborohydride in a suitable solvent such as THF or water to give a compound of formula (6).

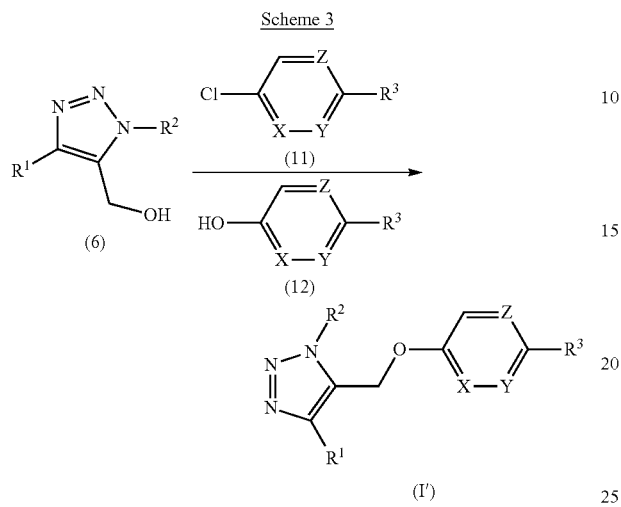

According to Scheme 3, compounds of formula (6) can be reacted with compounds of formula (11) in the presence of a suitable base, such as sodium hydride, in a suitable solvent, such as THF, or alternatively compounds of formula (6) can be reacted with compounds of formula (12) in the presence of triphenylphosphine and diethylazodicarboxylate, in a suitable solvent, such as THF to give a compound of formula (I') wherein A is —$CH_2$—O— and $R^2$ is alkyl. The present compounds of formula (I') wherein A is —$CH_2$—O— and $R^1$ is alkyl and their pharmaceutically acceptable salts can be prepared according to scheme 4.

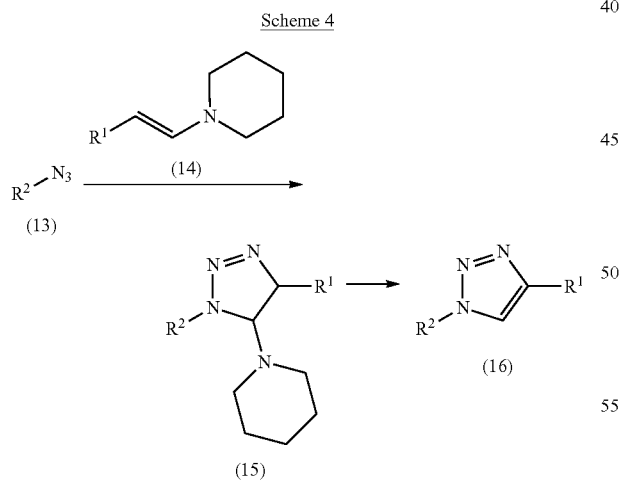

Compounds of formula (13) can be treated with compounds of formula (14) to give compounds of formula (15) which upon treatment with a base such as potassium hydroxide in a suitable solvent such as methanol gives compounds of formula (16). Compounds of formula (16) are equivalent to compounds of formula (4) in their subsequent reactivity and can be manipulated accordingly as shown above, e.g. in Scheme 1.

The present compounds of formula (I") wherein A is —CH=CH— and $R^2$ is alkyl and their pharmaceutically acceptable salts can be prepared according to Scheme 5.

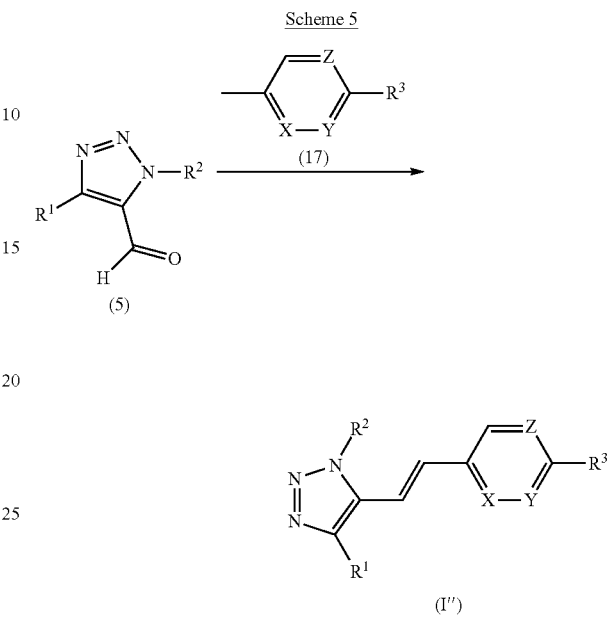

Compounds of formula (5) can be treated with compounds of formula (17) in the presence of acetic anhydride in acetic anhydride upon heating at 120° C. to give compounds of formula (I").

The present compounds of formula (I") wherein A is —CH=CH— and $R^1$ is alkyl and their pharmaceutically acceptable salts can be prepared according to Schemes 4, 1 and 5. Compounds of formula (16) are equivalent to compounds of formula (4) in their subsequent reactivity and can be manipulated accordingly as shown above.

The present compounds of formula (I') wherein A is —CH≡CH— and $R^2$ is alkyl and their pharmaceutically acceptable salts can be prepared according to Scheme 6.

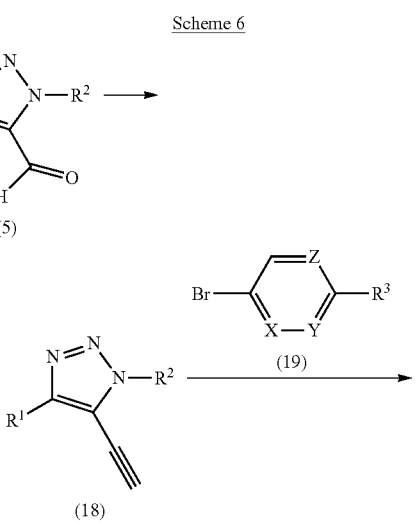

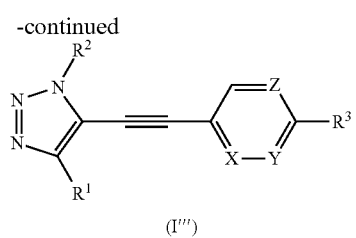

(I''')

Compounds of formula (5) can be treated with the Bestmann-Ohira reagent to give compounds of formula (18) which are then reacted under Sonogashira reaction conditions with compounds of formula (19) to give compounds of formula (I''').

The present compounds of formula (I''') wherein A is —CH═CH— and R$^1$ is alkyl and their pharmaceutically acceptable salts can be prepared according to Schemes 4, 1 and 6. Compounds of formula (16) are equivalent to compounds of formula (4) in their subsequent reactivity and can be manipulated accordingly as shown above.

In accordance with Scheme 7, compounds of formula (1) wherein R$^3$═—C(O)NR$^5$R$^6$ can be prepared following standard methods from compounds of formula (I) wherein R$^3$═—C(O)R$^4$.

EDAC=1-ethyl-3-(3-dimethylaminopropyl)carbodiimide hydrochloride
HOBt=hydroxybenzotriazole
hv=high vacuum
on=overnight
r.t.=room temperature
TBD=1,5,7-triazabicyclo[4.4.0]dec-5-ene
TBTU=O-(benzotriazol-1-yl)-N,N,N',N'-tetramethyluronium tetrafluoroborate
Tf$_2$O=trifluoromethanesulfonic anhydride
THF=tetrahydrofuran Another embodiment provides pharmaceutical compositions or medicaments containing the compounds of the invention and a therapeutically inert carrier, diluent or excipient, as well as methods of using the compounds of the invention to prepare such compositions and medicaments.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention can be administered by any suitable means, including oral, topical (including buccal Scheme 7

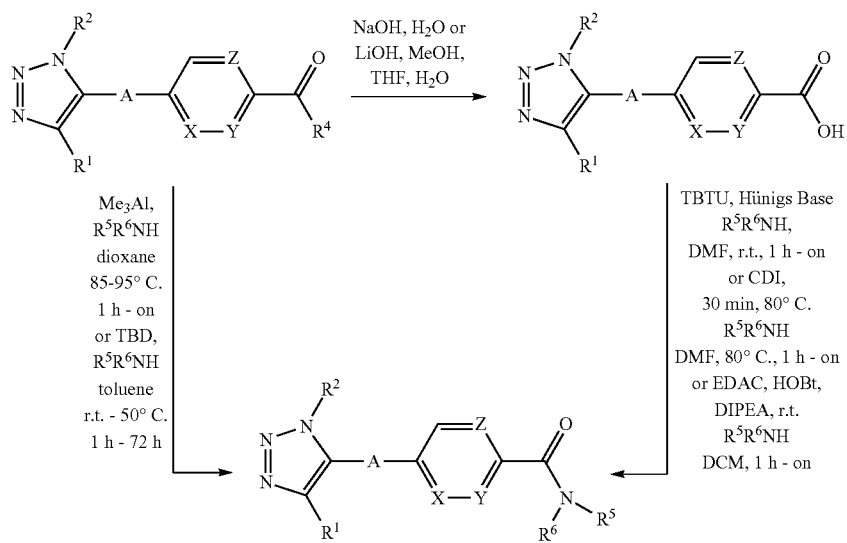

Insofar as their preparation is not described in the examples, the compounds of formula (I) as well as all intermediate products can be prepared according to analogous methods or according to the methods set forth above. Starting materials are commercially available, known in the art or can be prepared by methods known in the art or in analogy thereto.

The present invention also relates to compounds of formula (I) as defined above, when prepared by a process as described above.
BuLi=n-butyllithium
CDI=1,1'-carbonyldiimidazole
DCM=dichloromethane
DIPEA=N,N-diisopropylethylamine (Hünigs Base)
DMF=dimethylformamid and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention can be administered in any convenient administrative form, e.g., tablets, powders, capsules, solutions, dispersions, suspensions, syrups, sprays, suppositories, gels, emulsions, patches, etc. Such compositions can comprise components conventional in pharmaceutical preparations, e.g., diluents, carriers, pH modifiers, preservatives, solubilizers, stabilizers, wetting agents, emulsifiers, sweeteners, colorants, flavorants, salts for varying the osmotic pressure, buffers, masking agents, antioxidants, and further active agents. They can also comprise still other therapeutically valuable substances.

A typical formulation is prepared by mixing a compound of the present invention and a carrier or excipient. Suitable carriers and excipients are well known to those skilled in the art and are described in detail in, e.g., Ansel H. C. et al., *Ansel's Pharmaceutical Dosage Forms and Drug Delivery Systems* (2004) Lippincott, Williams & Wilkins, Philadelphia; Gennaro A. R. et al., *Remington: The Science and Practice of Pharmacy* (2000) Lippincott, Williams & Wilkins, Philadelphia; and Rowe R. C, *Handbook of Pharmaceutical Excipients* (2005) Pharmaceutical Press, Chicago. The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The dosage at which compounds of the invention can be administered can vary within wide limits and will, of course, be fitted to the individual requirements in each particular case. In general, in the case of oral administration a daily dosage of about 0.1 to 1000 mg per person of a compound of general formula (I) should be appropriate, although the above upper limit can also be exceeded when necessary.

An example of a suitable oral dosage form is a tablet containing about 100 mg to 500 mg of the compound of the invention compounded with about 90 to 30 mg anhydrous lactose, about 5 to 40 mg sodium croscarmellose, about 5 to 30 mg polyvinylpyrrolidone (PVP) K30, and about 1 to 10 mg magnesium stearate. The powdered ingredients are first mixed together and then mixed with a solution of the PVP. The resulting composition can be dried, granulated, mixed with the magnesium stearate and compressed to tablet form using conventional equipment.

An example of an aerosol formulation can be prepared by dissolving the compound, for example 10 to 100 mg, of the invention in a suitable buffer solution, e.g. a phosphate buffer, adding a tonicifier, e.g. a salt such as sodium chloride, if desired. The solution can be filtered, e.g., using a 0.2 μm filter, to remove impurities and contaminants.

As described above, the novel compounds of the present invention and their pharmaceutically acceptable salts and esters possess valuable pharmacological properties and have been found to be ligands for GABA A α5 receptors. The compounds of the present invention can therefore be used, either alone or in combination with other drugs, for the treatment or prevention of diseases which are modulated by ligands for GABA A receptors containing the α5 subunit. These diseases include, but are not limited to acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke, attentional disorders and need for cognition enhancement.

The invention therefore also relates to pharmaceutical compositions containing a compound as defined above and a pharmaceutically acceptable carrier and/or adjuvant.

The invention likewise embraces compounds as described above for use as therapeutically active substances.

The invention likewise embraces compounds as described above for use as therapeutically active substances for the treatment or prevention of diseases which are related to the GABA A α5 receptor.

The invention likewise embraces compounds as described above for use as therapeutically active substances for the treatment or prevention of acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for use as cognitive enhancers.

The invention likewise embraces compounds as described above for the treatment or prevention of acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for use as cognitive enhancers.

In another embodiment, the invention relates to a method for the treatment or prevention of diseases which are related to the GABA A α5 receptor.

In another embodiment, the invention relates to a method for the treatment or prevention of acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for cognition enhancement, which method comprises administering a compound as defined above to a human being or animal.

The invention also embraces the use of compounds as defined above for the treatment or prevention of diseases which are related to the GABA A α5 receptor.

The invention also embraces the use of compounds as defined above for the treatment or prevention of acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for cognition enhancement.

The invention also relates to the use of compounds as described above for the preparation of medicaments for the treatment or prevention of diseases which are related to the GABA A α5 receptor, particularly for the treatment or prevention of acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for the preparation of cognitive enhancers. Such medicaments comprise a compound as described above.

More particularly, the present invention relates to the use of compounds as described above for the treatment, prevention and/or delay of progression of CNS conditions caused by neurodevelopmental defects which result in excessive GABAergic inhibition in the cortex and hippocampus, wherein the CNS condition is selected from cognitive deficits in Down Syndrome, in autism, in neurofibromatosis type I, or after stroke.

The treatment or prevention of cognitive disorders, Alzheimer's disease, schizophrenia, positive, negative and/or cognitive symptoms associated with schizophrenia, Down syndrome, and neurofibromatosis type I, are particular embodiments of present invention.

A particular embodiment of the invention embraces the treatment or prevention of Alzheimer's disease.

A particular embodiment of the invention embraces the treatment or prevention of Down syndrome.

A particular embodiment of the invention embraces the treatment or prevention of neurofibromatosis type I.

The invention will be more fully understood by reference to the following examples. They should not, however, be construed as limiting the scope of the invention.

Example 1

N-Isopropyl-6-(3-methyl-5-phenyl-3H-[1,2,3]triazol-4-ylmethoxy)-nicotinamide

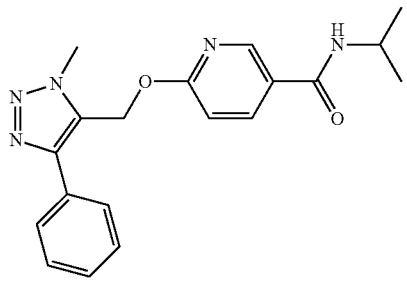 [SMILES: CC(C)NC(=O)c1ccc(OCc2c(-c3ccccc3)nnn2C)nc1]

4-Phenyl-1-trimethylsilanylmethyl-1H-[1,2,3]triazole

To a suspension of copper(I)iodide (19 mg, 0.1 mmol) in DMF (10 mL) was added DIPEA (171 µL, 1.00 mmol) and phenylacetylene (110 µL, 1.00 mmol) at room temperature and then trimethyl(triazomethyl)silane (646 mg, 5.00 mmol) was added. The resulting reaction mixture was stirred at room temperature for 18 h. The mixture was poured into water: brine (1:1) and then extracted with ethyl acetate. The combined organic extracts were then washed with brine, dried over sodium sulphate, filtered and evaporated. Purification by chromatography (silica, 0 to 50% ethyl acetate in heptane) afforded the title compound (179 mg, 77%) as a yellow solid. MS: m/e=231.0 [M]$^+$.

b) 1-Methyl-4-phenyl-1H-[1,2,3]triazole

Method A: A mixture of phenylacetylene (549 µL, 5.00 mmol), sodium azide (325 mg, 5.00 mmol), iodomethane (311 µL, 5.00 mmol), copper(I)iodide (190 mg, 1.00 mmol) and ascorbic acid (176 mg, 1.00 mmol) in water (12.5 mL) was sonicated for 6 h at room temperature. The mixture was then extracted with ethyl acetate (25 mL) and the solids filtered off. The aqueous layer of the filtrate was extracted with ethyl acetate and the combined organic extracts washed with brine, dried over sodium sulphate, filtered and evaporated. Purification by chromatography (silica, 50 to 100% ethyl acetate in heptane) afforded the title compound (118 mg, 15%) as a white solid. MS: m/e=160.1 [M+H]$^+$.

Method B: To a solution of 4-phenyl-1-trimethylsilanylmethyl-1H-[1,2,3]triazole (153 mg, 0.66 mmol) in THF (11 mL) was added water (23 µL, 1.32 mmol) and then tetrabutylammonium fluoride (1 M in THF, 394 µL, 0.79 mmol) was added dropwise at 0° C. The reaction mixture was stirred at 0° C. for 1 h. The resulting mixture was poured into water and then the THF was evaporated. The aqueous layer was then extracted with ethyl acetate and the combined organic extracts washed with brine, dried over sodium sulphate, filtered and evaporated. Purification by chromatography (silica, 0 to 100% ethyl acetate in heptane) afforded the title compound (98 mg, 93%) as a light brown solid. MS: m/e=160.1 [M+H]$^+$.

c) 3-Methyl-5-phenyl-3H-[1,2,3]triazole-4-carbaldehyde

To a solution of 1-methyl-4-phenyl-1H-[1,2,3]triazole (165 mg, 1.04 mmol) in THF (5.2 mL) was added n-BuLi (1.6 M in hexane, 777 µL, 1.24 mmol) dropwise at −75° C. under Argon. The resulted orange solution was stirred at −75° C. for 40 min, then DMF (104 µL, 1.35 mmol) was added dropwise at −75° C. and the reaction mixture was allowed to warm up to room temperature over 1 h. The mixture was then poured into saturated ammonium chloride solution and extracted with ethyl acetate and the combined organic extracts washed with brine, dried over sodium sulphate, filtered and evaporated. Purification by chromatography (silica, 0 to 50% ethyl acetate in heptane) afforded the title compound (131 mg, 68%) as a white solid. MS: m/e=187.0 [M]⁺.

d) (3-Methyl-5-phenyl-3H-[1,2,3]triazol-4-yl)-methanol

Method A: To a solution of 3-methyl-5-phenyl-3H-[1,2,3]triazole-4-carbaldehyde (102 mg, 0.545 mmol) in MeOH (10 mL) was added sodiumborohydride (41 mg, 1.09 mmol) under Argon at room temperature and the reaction mixture was allowed to warm up to room temperature over 1 h. The mixture was then poured into saturated ammonium chloride solution and extracted with ethyl acetate and the combined organic extracts washed with brine, dried over sodium sulphate, filtered and evaporated. Purification by chromatography (silica, 0 to 100% ethyl acetate in heptane) afforded the title compound (85 mg, 82%) as a white solid. MS: m/e=190.3 [M+H]⁺.

e) 6-(3-Methyl-5-phenyl-3H-[1,2,3]triazol-4-ylmethoxy)-nicotinic acid methyl ester A solution of (3-methyl-5-phenyl-3H-[1,2,3]triazol-4-yl)-methanol (189 mg, 1.0 mmol) in THF (3 mL) was added dropwise at 0° C. to a suspension of NaH (55% in oil, 48 mg, 1.1 mmol) in THF (1.5 mL) and the reaction mixture was then stirred at room temperature for 30 min. Then a solution of methyl 6-chloronicotinate (189 mg, 1.1 mmol) in THF (3 mL) was added dropwise at 0° C. and the reaction mixture stirred at room temperature for 20 h. The mixture was then poured into water extracted with ethyl acetate and the combined organic extracts washed with brine, dried over sodium sulphate, filtered and evaporated. Purification by chromatography (silica, 0 to 100% ethyl acetate in heptane) afforded the title compound (203 mg, 63%) as an off white solid. MS: m/e=325.2 [M+H]⁺.

f) N-Isopropyl-6-(3-methyl-5-phenyl-3H-[1,2,3]triazol-4-ylmethoxy)-nicotinamide To a solution of isopropylamine (95 µL, 1.11 mmol) in dioxane (5.5 mL) was added dropwise trimethylaluminium (2 M in heptane, 600 µL, 1.11 mmol). The resulting solution was stirred at room temperature for 1 h, then a solution of 6-(3-methyl-5-phenyl-3H-[1,2,3]triazol-4-ylmethoxy)-nicotinic acid methyl ester (90 mg, 0.28 mmol) in dioxane (2.8 mL) was added and the reaction mixture was stirred at 90° C. for 5 h. After cooling to room temperature the mixture was poured into a Na—K-tartrate solution extracted with ethyl acetate and the combined organic extracts washed with brine, dried over sodium sulphate, filtered and evaporated to afford the title compound (83 mg, 85%) as a white solid. MS: m/e=352.3 [M+H]⁺.

Example 2

6-(3-Methyl-5-phenyl-3H-[1,2,3]triazol-4-ylmethoxy)-N-(tetrahydro-pyran-4-yl)-nicotinamide

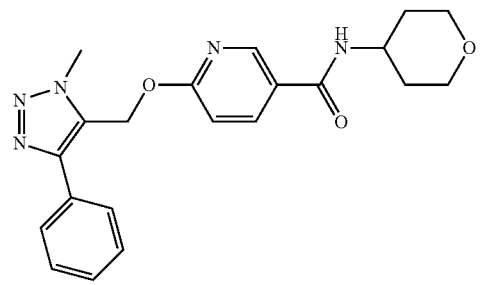

a) 6-(3-Methyl-5-phenyl-3H-[1,2,3]triazol-4-ylmethoxy)-nicotinic acid

A solution of lithium hydroxide monohydrate (40 mg, 0.96 mmol) in water (1.2 mL) was added dropwise to a suspension of 6-(3-methyl-5-phenyl-3H-[1,2,3]triazol-4-ylmethoxy)-nicotinic acid methyl ester (156 mg, 0.96 mmol) in THF (1.2 mL) and MeOH (0.3 mL). The reaction mixture was then stirred at room temperature for 2 h. The reaction mixture was then evaporated and the residue dissolved in water, acidified with HCl (1N), and the resulting precipitate filtered off to afford the title product (129 mg, 86%) as a white solid. MS: m/e=309.4 [M−H]⁻.

b) 6-(3-Methyl-5-phenyl-3H-[1,2,3]triazol-4-ylmethoxy)-N-(tetrahydro-pyran-4-yl)-nicotinamide To a solution of 6-(3-methyl-5-phenyl-3H-[1,2,3]triazol-4-ylmethoxy)-nicotinic acid (155 mg, 0.50 mmol) and TBTU (177 mg, 0.55 mmol) in DMF (2.5 mL) was added DIPEA (428 µL, 2.50 mmol). Then 4-aminotetrahydropyran (56 mg, 0.55 mmol) was added and the mixture was stirred at room temperature under Ar for 1 h. The mixture was then evaporated and purification by chromatography (silica, 0 to 100% ethyl acetate in heptane, then 5% methanol in dichloromethane) afforded the title compound (43 mg, 22%) as a white solid after recrystallisation from ethyl acetate/heptane. MS: m/e=394.1 [M+H]⁺.

Example 3

6-(3-Methyl-5-phenyl-3H-[1,2,3]triazol-4-ylmethoxy)-N-morpholin-4-yl-nicotinamide

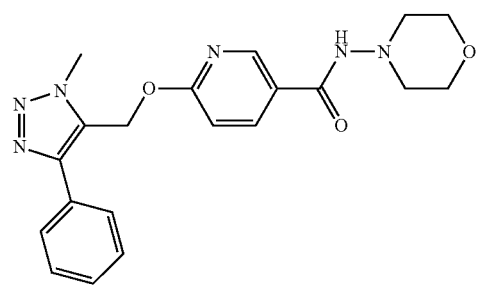

As described for example 2b, 6-(3-methyl-5-phenyl-3H-[1,2,3]triazol-4-ylmethoxy)-nicotinic acid (155 mg, 0.5 mmol) was converted, using N-aminomorpholine instead of 4-aminotetrahydropyran, to the title compound (165 mg, 84%) which was obtained as a white solid. MS: m/e=395.2 [M+H]$^+$.

Example 4

N-Cyclopropyl-6-(3-methyl-5-phenyl-3H-[1,2,3]triazol-4-ylmethoxy)-nicotinamide

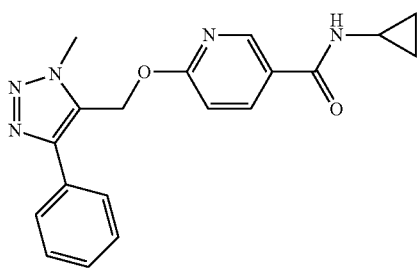 [SMILES: Cn1nnc(-c2ccccc2)c1COc1ccc(C(=O)NC2CC2)cn1]

As described for example 2b, 6-(3-methyl-5-phenyl-3H-[1,2,3]triazol-4-ylmethoxy)-nicotinic acid (155 mg, 0.5 mmol) was converted, using cyclopropylamine instead of 4-aminotetrahydropyran, to the title compound (167 mg, 96%) which was obtained as a white solid. MS: m/e=350.3 [M+H]$^+$.

Example 5

N-Cyclopropylmethyl-6-(3-methyl-5-phenyl-3H-[1,2,3]triazol-4-ylmethoxy)-nicotinamide

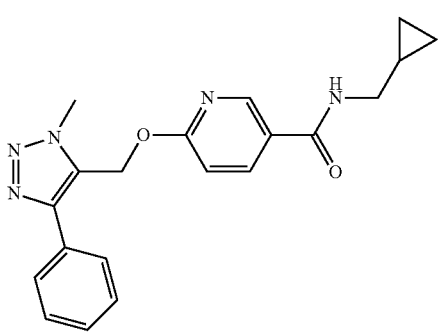 [SMILES: Cn1nnc(-c2ccccc2)c1COc1ccc(C(=O)NCC2CC2)cn1]

As described for example 2b, 6-(3-methyl-5-phenyl-3H-[1,2,3]triazol-4-ylmethoxy)-nicotinic acid (155 mg, 0.5 mmol) was converted, using aminomethylcyclopropane instead of 4-aminotetrahydropyran, to the title compound (143 mg, 79%) which was obtained as a white solid. MS: m/e=364.2 [M+H]$^+$.

Example 6

N-(1,1-Dioxo-tetrahydro-1,6-thiophen-3-yl)-6-(3-methyl-5-phenyl-3H-[1,2,3]triazol-4-ylmethoxy)-nicotinamide

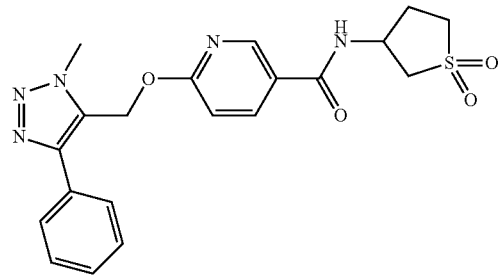 [SMILES: Cn1nnc(-c2ccccc2)c1COc1ccc(C(=O)NC2CCS(=O)(=O)C2)cn1]

As described for example 2b, 6-(3-methyl-5-phenyl-3H-[1,2,3]triazol-4-ylmethoxy)-nicotinic acid (155 mg, 0.5 mmol) was converted, using 1,1-dioxidotetrahydrothien-3-ylamine instead of 4-aminotetrahydropyran, to the title compound (176 mg, 82%) which was obtained as a white solid. MS: m/e=428.2 [M+H]$^+$.

Example 7

6-(3-Methyl-5-phenyl-3H-[1,2,3]triazol-4-ylmethoxy)-N-(2,2,2-trifluoro-ethyl)-nicotinamide

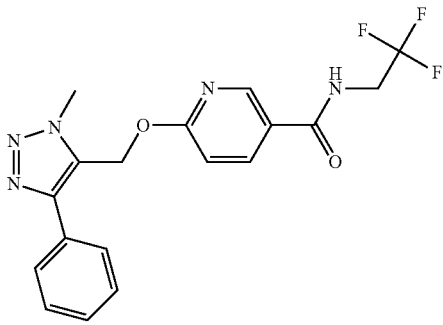 [SMILES: Cn1nnc(-c2ccccc2)c1COc1ccc(C(=O)NCC(F)(F)F)cn1]

As described for example 2b, 6-(3-methyl-5-phenyl-3H-[1,2,3]triazol-4-ylmethoxy)-nicotinic acid (155 mg, 0.5 mmol) was converted, using 2,2,2-trifluoroethylamine instead of 4-aminotetrahydropyran, to the title compound (127 mg, 58%) which was obtained as a white solid after a further recrystallisation from ethyl acetate. MS: m/e=392.1 [M+H]$^+$.

Example 8

N-(2-Hydroxy-ethyl)-6-(3-methyl-5-phenyl-3H-[1,2,3]triazol-4-ylmethoxy)-nicotinamide

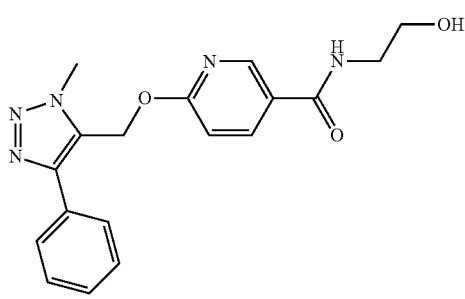 [SMILES: Cn1nnc(-c2ccccc2)c1COc1ccc(C(=O)NCCO)cn1]

As described for example 2b, 6-(3-methyl-5-phenyl-3H-[1,2,3]triazol-4-ylmethoxy)-nicotinic acid (155 mg, 0.5 mmol) was converted, using aminoethanol instead of 4-aminotetrahydropyran, to the title compound (103 mg, 58%) which was obtained as a white solid after a further recrystallisation from ethyl acetate. MS: m/e=354.2 [M+H]+.

Example 9

6-[5-(4-Fluoro-phenyl)-3-methyl-3H-[1,2,3]triazol-4-ylmethoxy]-nicotinic acid methyl ester

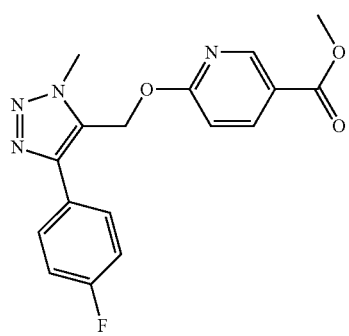 [SMILES: COC(=O)c1ccc(OCc2c(-c3ccc(F)cc3)nnn2C)nc1]

(4-Fluoro-phenyl)-propynoic acid ethyl ester

Prepared in analogy to Synthesis Communications (1989) 3:217-218. To a solution of triphenylphosphine oxide (3.77 g, 14 mmol) in 1,2-dichloroethane (42 mL) was added trifluoromethanesulfonic anhydride (2.25 mL, 14 mmol) dropwise at 0° C. and the grey suspension was stirred at 0° C. for 15 min. Then a solution of 3-(4-fluoro-phenyl)-3-oxo-propionic acid ethyl ester (2.85 g, 14 mmol) in 1,2-dichloroethane (14 mL) was added followed by a dropwise addition of triethylamine (3.78 mL, 28 mmol) at 0° C. The brown solution was refluxed for 2.5 h. After cooling the mixture was poured onto ice-water and the organic layer separated and washed with brine, dried over sodium sulphate, filtered and evaporated. Purification by chromatography (silica, 0 to 20% ethyl acetate in heptane) afforded the title compound (1.53 g, 59%) as a yellow solid. MS: m/e=193.2 [M+H]+.

b) 5-(4-Fluoro-phenyl)-3-trimethylsilanylmethyl-3H-[1,2,3]-triazole-4-carboxylic acid ethyl ester To a solution of (4-fluoro-phenyl)-propynoic acid ethyl ester (1.45 g, 7.55 mmol) in benzene (25 mL) was added azidomethyl-trimethyl-silane (1.17 g, 9.05 mmol) and the reaction mixture was refluxed under nitrogen for 72 h. A subsequent batch of azidomethyl-trimethyl-silane (0.29 g, 2.26 mmol) was added and refluxing was continued for 5 h. The mixture was then evaporated and purification by chromatography (silica, 0 to 50% ethyl acetate in heptane) afforded the title compound (1.0 g, 41%) as a yellow oil. MS: m/e=322.2 [M+H]+.

c) [5-(4-Fluoro-phenyl)-3-trimethylsilanylmethyl-3H-[1,2,3]triazol-4-yl]-methanol To a solution of 5-(4-fluoro-phenyl)-3-trimethylsilanylmethyl-3H-[1,2,3]triazole-4-carboxylic acid ethyl ester (880 mg, 2.74 mmol) in dry THF (8.2 mL) was added portionwise lithiumaluminiumhydride (119 mg, 3.15 mmol) at 0° C. and the reaction mixture was stirred at 0° C. for 1 h. Then water (119 μL) and NaOH (15%, 119 μL) was added followed by water (357 μL). The precipitate was then filtered off and the filtrate evaporated. Purification by chromatography (silica, 0 to 100% ethyl acetate in heptane) afforded the title compound (649 mg, 85%) as a white solid. MS: m/e=280.1 [M+H]+.

d) [5-(4-Fluoro-phenyl)-3-methyl-3H-[1,2,3]triazol-4-yl]-methanol

To a solution of [5-(4-fluoro-phenyl)-3-trimethylsilanylmethyl-3H-[1,2,3]triazol-4-yl]-methanol (616 mg, 2.20 mmol) in THF (37 mL) was added water (79 μL, 4.41 mmol) and then tetrabutylammonium fluoride (1 M in THF, 2.65 mL, 2.65 mmol) added dropwise at 0° C. The reaction mixture was stirred at 0° C. for 15 min. The resulting mixture was poured into water and then the THF was evaporated. The aqueous layer was then extracted with ethyl acetate and the combined organic extracts washed with brine, dried over sodium sulphate, filtered and evaporated. Purification by chromatography (silica, 0 to 100% ethyl acetate in heptane) afforded the title compound (410 mg, 90%) as an off white solid. MS: m/e=208.0 [M+H]+.

e) 6-[5-(4-Fluoro-phenyl)-3-methyl-3H-[1,2,3]-triazol-4-ylmethoxy]-nicotinic acid methyl ester A solution of [5-(4-fluoro-phenyl)-3-methyl-3H-[1,2,3]triazol-4-yl]-methanol (380 mg, 2.02 mmol) in THF (5.5 mL) was added dropwise at 0° C. to a suspension of NaH (55% in oil, 88 mg, 2.02 mmol) in THF (2.7 mL) and the reaction mixture was then stirred at room temperature for 30 min. Then a solution of methyl 6-chloronicotinate (346 mg, 2.02 mmol) in THF (5.5 mL) was added dropwise at 0° C. and the reaction mixture stirred at room temperature for 16 h. The mixture was then poured into water extracted with ethyl acetate and the combined organic extracts washed with brine, dried over sodium sulphate, filtered and evaporated. Purification by chromatography (silica, 0 to 100% ethyl acetate in heptane) afforded the title compound (449 mg, 72%) as a white solid. MS: m/e=343.1 [M+H]+.

Example 10

6-[5-(4-Fluoro-phenyl)-3-methyl-3H-[1,2,3]triazol-4-ylmethoxy]-N-(tetrahydro-pyran-4-yl)-nicotinamide

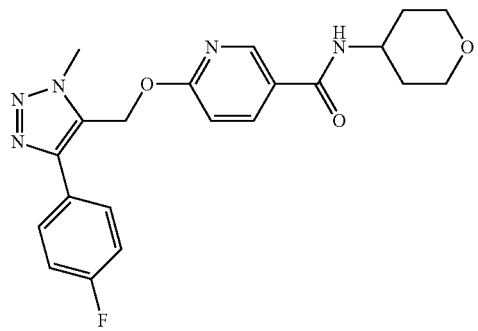 [SMILES: Cn1nnc(-c2ccc(F)cc2)c1COc1ccc(C(=O)NC2CCOCC2)cn1]

a) 6-[5-(4-Fluoro-phenyl)-3-methyl-3H-[1,2,3]triazol-4-ylmethoxy]-nicotinic acid A solution of lithium hydroxide monohydrate (101 mg, 2.41 mmol) in water (3 mL) was added dropwise to a suspension of 6-[5-(4-fluoro-phenyl)-3-methyl-3H-[1,2,3]triazol-4-ylmethoxy]-nicotinic acid methyl ester (413 mg, 1.21 mmol) in THF (3 mL) and MeOH (0.6 mL). The reaction mixture was then stirred at room temperature for 1 h. The reaction mixture was then evaporated and the residue dissolved in water, acidified with HCl (1N), and the resulting precipitate filtered off to afford the title product (380 mg, 96%) as a white solid. MS: m/e=327.3 [M−H]⁻.

b) 6-[5-(4-Fluoro-phenyl)-3-methyl-3H-[1,2,3]triazol-4-ylmethoxy]-N-isopropyl-nicotinamide To a solution of 6-[5-(4-fluoro-phenyl)-3-methyl-3H-[1,2,3]triazol-4-ylmethoxy]-nicotinic acid (94 mg, 0.29 mmol) and TBTU (101 mg, 0.32 mmol) in DMF (1.5 mL) was added DIPEA (245 µL, 1.43 mmol). Then 4-aminotetrahydropyran (56 mg, 0.55 mmol) was added and the mixture was stirred at room temperature under Ar for 1 h. The mixture was then evaporated and purification by chromatography (silica, 50 to 100% ethyl acetate in heptane) afforded the title compound (82 mg, 70%) as a white solid after recrystallisation from methanol/water. MS: m/e=412.2 [M+H]⁺.

Example 11

6-[5-(4-Fluoro-phenyl)-3-methyl-3H-[1,2,3]triazol-4-ylmethoxy]-N-isopropyl-nicotinamide

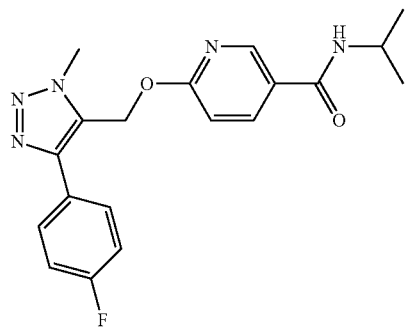 [SMILES: CC(C)NC(=O)c1ccc(OCc2c(-c3ccc(F)cc3)nnn2C)nc1]

As described for example 10b, 6-[5-(4-fluoro-phenyl)-3-methyl-3H-[1,2,3]triazol-4-ylmethoxy]-nicotinic acid (94 mg, 0.29 mmol) was converted, using isopropylamine instead of 4-aminotetrahydropyran, to the title compound (69 mg, 65%) which was obtained as a white solid. MS: m/e=370.2 [M+H]⁺.

Example 12

6-[5-(4-Fluoro-phenyl)-3-methyl-3H-[1,2,3]triazol-4-ylmethoxy]-N-(2-hydroxy-1,1-dimethyl-ethyl)-nicotinamide

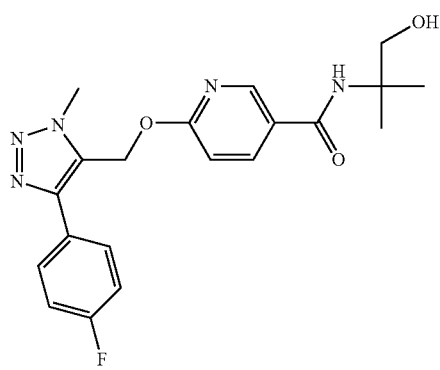 [SMILES: Cn1nnc(-c2ccc(F)cc2)c1COc1ccc(C(=O)NC(C)(C)CO)cn1]

As described for example 10b, 6-[5-(4-fluoro-phenyl)-3-methyl-3H-[1,2,3]triazol-4-ylmethoxy]-nicotinic acid (94 mg, 0.29 mmol) was converted, using 2-amino-2-methyl-1-propanol instead of 4-aminotetrahydropyran, to the title compound (65 mg, 57%) which was obtained as a white solid. MS: m/e=400.3 [M+H]⁺.

Example 13

6-[5-(4-Fluoro-phenyl)-3-methyl-3H-[1,2,3]triazol-4-ylmethoxy]-N-(3-methyl-oxetan-3-yl)-nicotinamide

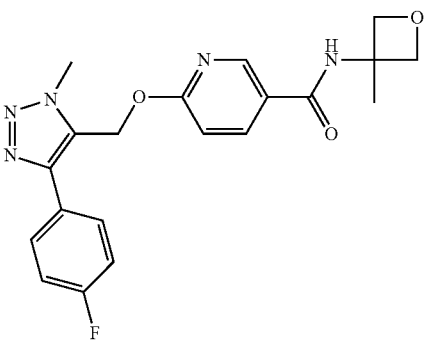

As described for example 10b, 6-[5-(4-fluoro-phenyl)-3-methyl-3H-[1,2,3]triazol-4-ylmethoxy]-nicotinic acid (68 mg, 0.21 mmol) was converted, using 3-methyl-oxetanamine instead of 4-aminotetrahydropyran, to the title compound (21 mg, 26%) which was obtained as a white solid. MS: m/e=398.2 [M+H]⁺.

Example 14

6-[5-(4-Fluoro-phenyl)-3-methyl-3H-[1,2,3]triazol-4-ylmethoxy]-N-morpholin-4-yl-nicotinamide

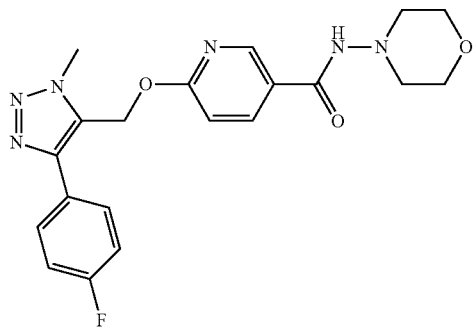

As described for example 10b, 6-[5-(4-fluoro-phenyl)-3-methyl-3H-[1,2,3]triazol-4-ylmethoxy]-nicotinic acid (68 mg, 0.21 mmol) was converted, using N-aminomorpholine instead of 4-aminotetrahydropyran, to the title compound (65 mg, 76%) which was obtained as a white solid. MS: m/e=413.2 [M+H]$^+$.

Example 15

6-[5-(4-Fluoro-phenyl)-3-methyl-3H-[1,2,3]triazol-4-ylmethoxy]-N-(3,3,3-trifluoro-2-hydroxy-propyl)-nicotinamide

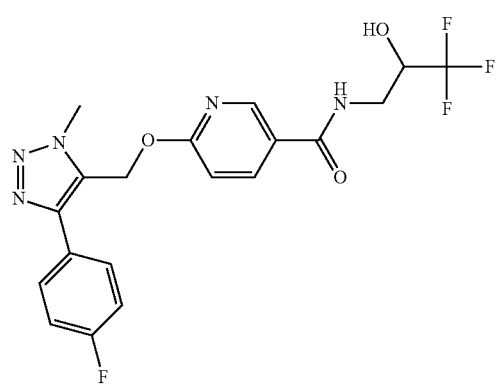 [SMILES: Cn1nnc(-c2ccc(F)cc2)c1COc1ccc(C(=O)NCC(O)C(F)(F)F)cn1]

As described for example 10b, 6-[5-(4-fluoro-phenyl)-3-methyl-3H-[1,2,3]triazol-4-ylmethoxy]-nicotinic acid (68 mg, 0.21 mmol) was converted, using 3-amino-1,1,1-trifluoro-2-propanol instead of 4-aminotetrahydropyran, to the title compound (69 mg, 76%) which was obtained as a white solid. MS: m/e=440.3 [M+H]$^+$.

Example 16

6-[5-(4-Fluoro-phenyl)-3-methyl-3H-[1,2,3]triazol-4-ylmethoxy]-N-(2-hydroxy-ethyl)-nicotinamide

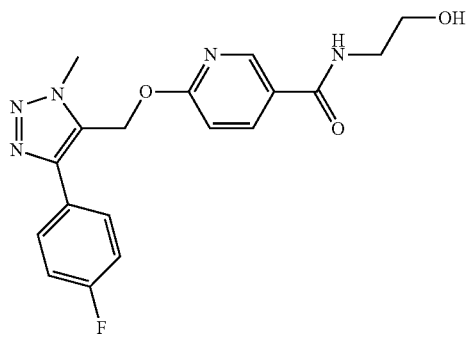 [SMILES: Cn1nnc(-c2ccc(F)cc2)c1COc1ccc(C(=O)NCCO)cn1]

As described for example 10b, 6-[5-(4-fluoro-phenyl)-3-methyl-3H-[1,2,3]triazol-4-ylmethoxy]-nicotinic acid (68 mg, 0.21 mmol) was converted, using ethanolamine instead of 4-aminotetrahydropyran, to the title compound (55 mg, 72%) which was obtained as an off white solid. MS: m/e=372.1 [M+H]$^+$.

Example 17

6-((4-(4-Fluorophenyl)-1-methyl-1H-1,2,3-triazol-5-yl)methoxy)-2-isopropyl-1H-pyrrolo[3,4-c]pyridin-3(2H)-one

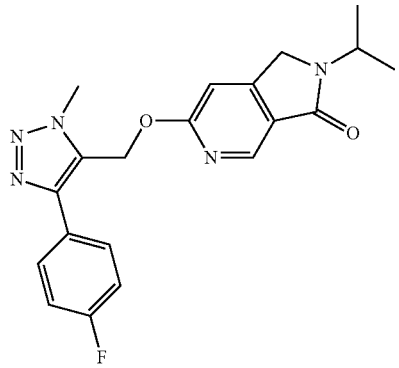 [SMILES: CC(C)N1Cc2cc(OCc3c(-c4ccc(F)cc4)nnn3C)ncc2C1=O]

To a solution of [5-(4-fluoro-phenyl)-3-methyl-3H-[1,2,3]triazol-4-yl]-methanol (251 mg, 1.21 mmol) in THF (30 mL) was added 6-hydroxy-2-isopropyl-1H-pyrrolo[3,4-c]pyridin-3(2H)-one (232 mg, 1.21 mmol) and triphenylphosphine (413 mg, 1.58 mmol) at ambient temperature under an argon atmosphere. Then diethyl azodicarboxylate (624 μL, 1.58 mmol) was added and the reaction mixture was stirred for 72 h at room temperature. Concentration and purification by chromatography (silica, 20 to 50% ethyl acetate in heptane) afforded the title compound (87 mg, 19%) as a white solid. MS: m/e=382.2 [M+H]$^+$.

Example 18

Methyl 6-((4-(2-fluorophenyl)-1-methyl-1H-1,2,3-triazol-5-yl)methoxy)nicotinate

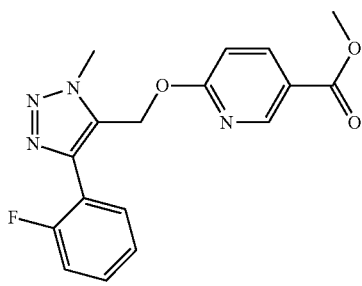 [SMILES: COC(=O)c1ccc(OCc2c(-c3ccccc3F)nnn2C)nc1]

a) 4-(2-Fluorophenyl)-1-methyl-1H-1,2,3-triazole

As described for example 1a, Method A, 2-fluorophenylacetylene instead of phenylacetylene afforded the title compound (20.6 g, 75%) as an off white solid. MS: m/e=178.1 [M+H]$^+$.

b) 4-(2-Fluorophenyl)-1-methyl-1H-1,2,3-triazole-5-carbaldehyde

To a solution of 4-(2-fluorophenyl)-1-methyl-1H-1,2,3-triazole (1.44 g, 8.1 mmol) in THF (41 mL) was added n-BuLi (1.6 M in hexane, 6.10 mL, 9.8 mmol) dropwise at −75° C. under Argon. The resulted orange solution was stirred at −75° C. for 1 h, then DMF (0.82 mL, 10.6 mmol) was added dropwise at −75° C. and the reaction mixture was allowed to warm up to room temperature over 1 h. The mixture was then poured into saturated ammonium chloride solution and extracted with ethyl acetate and the combined organic extracts washed with brine, dried over sodium sulphate, filtered and evaporated. Purification by chromatography (silica, 0 to 50% ethyl acetate in heptane) afforded the title compound (1.45 g, 87%) as an off white solid. MS: m/e=206.0 [M]$^+$.

c) (4-(2-Fluorophenyl)-1-methyl-1H-1,2,3-triazol-5-yl)methanol

To a solution of 4-(2-fluorophenyl)-1-methyl-1H-1,2,3-triazole-5-carbaldehyde (411 mg, 2.0 mmol) in MeOH (42 mL) was added sodiumborohydride (38 mg, 1.00 mmol) under Argon at room temperature and the reaction mixture was allowed to warm up to room temperature over 0.5 h. The mixture was then poured into saturated ammonium chloride solution and extracted with ethyl acetate and the combined organic extracts washed with brine, dried over sodium sulphate, filtered and evaporated. Purification by chromatography (silica, 0 to 100% ethyl acetate in heptane) afforded the title compound (360 mg, 87%) as a white solid. MS: m/e=208.1 [M+H]$^+$.

d) Methyl 6-((4-(2-fluorophenyl)-1-methyl-1H-1,2,3-triazol-5-yl)methoxy)nicotinate A solution of (4-(2-fluorophenyl)-1-methyl-1H-1,2,3-triazol-5-yl)methanol (100 mg, 0.48 mmol) in THF (1.4 mL) was added dropwise at 0° C. to a suspension of NaH (60% in oil, 21 mg, 0.53 mmol) in THF (0.7 mL) and the reaction mixture was then stirred at room temperature for 30 min. Then a solution of methyl 6-chloronicotinate (91 mg, 0.53 mmol) in THF (1 mL) was added dropwise at 0° C. and the reaction mixture stirred at room temperature for 16 h. The mixture was then poured into water extracted with ethyl acetate and the combined organic extracts washed with brine, dried over sodium sulphate, filtered and evaporated. Purification by chromatography (silica, 0 to 100% ethyl acetate in heptane) afforded the title compound (110 mg, 67%) as a colourless gum. MS: m/e=343.1 [M+H]$^+$.

Example 19

6-((4-(2-Fluorophenyl)-1-methyl-1H-1,2,3-triazol-5-yl)methoxy)-N-(tetrahydro-2H-pyran-4-yl)nicotinamide

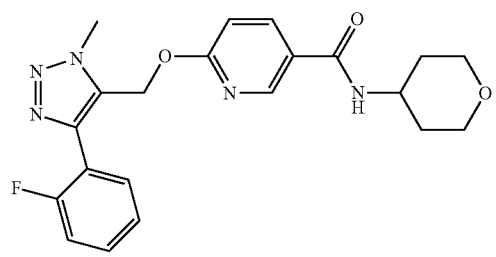 [SMILES: Cn1nnc(-c2ccccc2F)c1COc1ccc(C(=O)NC2CCOCC2)cn1]

a) 6-((4-(2-Fluorophenyl)-1-methyl-1H-1,2,3-triazol-5-yl)methoxy)nicotinic acid A solution of lithium hydroxide monohydrate (23 mg, 0.56 mmol) in water (0.8 mL) was added dropwise to a suspension of methyl 6-((4-(2-fluorophenyl)-1-methyl-1H-1,2,3-triazol-5-yl)methoxy)nicotinate (95 mg, 0.28 mmol) in THF (0.8 mL). The reaction mixture was then stirred at room temperature for 2 h. The reaction mixture was then evaporated and the residue dissolved in water, acidified with HCl (1N), and the resulting precipitate filtered off to afford the title product (68 mg, 75%) as a white solid. MS: m/e=327.1 [M−H]$^-$.

b) 6-((4-(2-Fluorophenyl)-1-methyl-1H-1,2,3-triazol-5-yl)methoxy)-N-(tetrahydro-2H-pyran-4-yl)nicotinamide To a solution of 6-((4-(2-fluorophenyl)-1-methyl-1H-1,2,3-triazol-5-yl)methoxy)nicotinic acid (98 mg, 0.3 mmol) and TBTU (105 mg, 0.33 mmol) in DMF (1 mL) was added DIPEA (261 µL, 1.49 mmol). Then 4-aminotetrahydropyran (34 µL, 0.33 mmol) was added and the mixture was stirred at room temperature under Ar for 1 h. The mixture was then evaporated and purification by chromatography (silica, 50 to 100% ethyl acetate in heptane) afforded the title compound (108 mg, 88%) as a white solid after recrystallisation from ethyl acetate/heptane. MS: m/e=412.3 [M+H]$^+$.

Example 20

6-((4-(2-Fluorophenyl)-1-methyl-1H-1,2,3-triazol-5-yl)methoxy)-N-isopropylnicotinamide

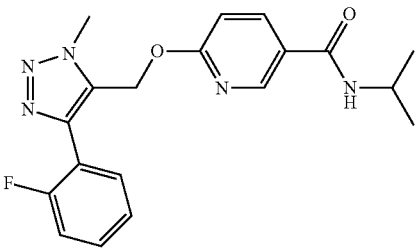 [SMILES: CC(C)NC(=O)c1ccc(OCc2c(-c3ccccc3F)nnn2C)nc1]

As described for example 19b, 6-((4-(2-fluorophenyl)-1-methyl-1H-1,2,3-triazol-5-yl)methoxy)nicotinic acid (98 mg, 0.3 mmol) was converted, using isopropylamine instead of 4-aminotetrahydropyran, to the title compound (94 mg, 85%) which was obtained as a white solid. MS: m/e=370.1 [M+H]+.

Example 21

6-((4-(2-Fluorophenyl)-1-methyl-1H-1,2,3-triazol-5-yl)methoxy)-N-(3-methyloxetan-3-yl)nicotinamide

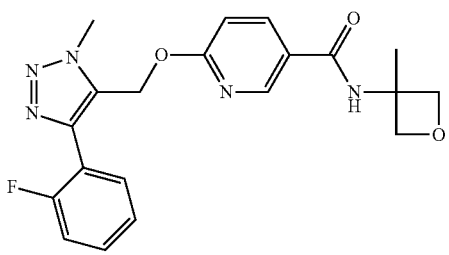 [SMILES: Cn1nnc(-c2ccccc2F)c1COc1ccc(C(=O)NC2(C)COC2)cn1]

As described for example 19b, 6-((4-(2-fluorophenyl)-1-methyl-1H-1,2,3-triazol-5-yl)methoxy)nicotinic acid (98 mg, 0.3 mmol) was converted, using 3-methyl-3-oxetanamine instead of 4-aminotetrahydropyran, to the title compound (72 mg, 61%) which was obtained as a white solid. MS: m/e=398.2 [M+H]+.

Example 22

(1,1-Dioxo-1,6-thiomorpholin-4-yl)-{6-[5-(2-fluorophenyl)-3-methyl-3H-[1,2,3]triazol-4-ylmethoxy]-pyridin-3-yl}-methanone

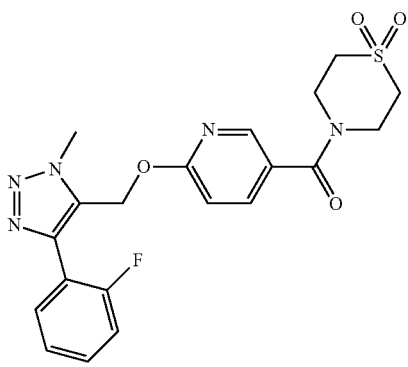 [SMILES: Cn1nnc(-c2ccccc2F)c1COc1ccc(C(=O)N2CCS(=O)(=O)CC2)cn1]

As described for example 19b, 6-((4-(2-fluorophenyl)-1-methyl-1H-1,2,3-triazol-5-yl)methoxy)nicotinic acid (98 mg, 0.3 mmol) was converted, using thiomorpholine 1,1-dioxide instead of 4-aminotetrahydropyran, to the title compound (76 mg, 57%) which was obtained as a white solid. MS: m/e=446.3 [M+H]+.

Example 23

(6-((4-(2-Fluorophenyl)-1-methyl-1H-1,2,3-triazol-5-yl)methoxy)pyridin-3-yl)(2-oxa-6-azaspiro[3.3]heptan-6-yl)methanone

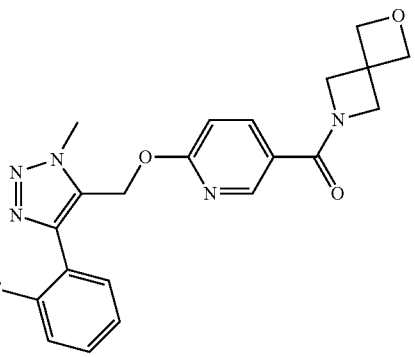

As described for example 19b, 6-((4-(2-fluorophenyl)-1-methyl-1H-1,2,3-triazol-5-yl)methoxy)nicotinic acid (98 mg, 0.3 mmol) was converted, using 2-oxa-6-azonia-spiro[3.3]heptane oxalate salt instead of 4-aminotetrahydropyran, to the title compound (77 mg, 63%) which was obtained as a white foam. MS: m/e=410.3 [M+H]+.

Example 24

6-((4-(2-Fluorophenyl)-1-methyl-1H-1,2,3-triazol-5-yl)methoxy)-N-morpholinonicotinamide

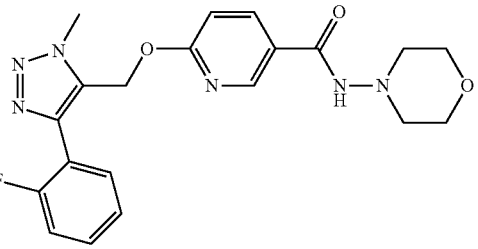

As described for example 19b, 6-((4-(2-fluorophenyl)-1-methyl-1H-1,2,3-triazol-5-yl)methoxy)nicotinic acid (98 mg, 0.3 mmol) was converted, using 4-aminomorpholine instead of 4-aminotetrahydropyran, to the title compound (89 mg, 72%) which was obtained as a white foam. MS: m/e=413.4 [M+H]+.

Example 25

6-(3-Methyl-5-pyridin-2-yl-3H-[1,2,3]triazol-4-ylmethoxy)-nicotinic acid methyl ester

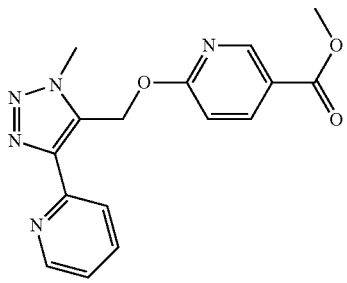 [SMILES: COC(=O)c1ccc(OCc2c(-c3ccccn3)nnn2C)nc1]

a) 2-Ethynyl-pyridine

A solution of 2-trimethylsilanylethynyl-pyridine (3.05 g, 14 mmol) in MeOH (8.5 mL) was added dropwise to potassium hydroxide solution (1 N, 14 mL) and the reaction mixture was stirred at room temperature for 1 h and then acidified with HCl (3 N, 8.5 mL) and the mixture concentrated. The residue was then diluted with water and make alkaline with solid sodium carbonate, extracted with diethyl ether and the combined organic extracts washed with brine, dried over sodium sulphate, filtered and evaporated. Purification by chromatography (silica, diethylether) afforded the title compound (1.3 g, 75%) as a brown liquid. MS: m/e=176.0 [M+H]+.

b) Pyridin-2-yl-propynoic acid ethyl ester

To a solution of 2-ethynyl-pyridine (309 mg, 3 mmol) in THF (6 mL) was added BuLi (1.6 M in hexane, 1.88 mL, 3 mmol) dropwise at −75° C. and the reaction mixture was stirred at −75° C. for 30 min, then ethyl chloroformate (286 µL, 3 mmol) was added dropwise at −75° C. and the reaction mixture was stirred at −75° C. for 1 h. The mixture was then poured into ice water and extracted with ethyl acetate and the combined organic extracts washed with brine, dried over sodium sulphate, filtered and evaporated. Purification by chromatography (silica, 0 to 50% ethyl acetate in heptane) afforded the title compound (349 mg, 66%) as a brown solid. MS: m/e=176.2 [M+H]+.

c) 5-Pyridin-2-yl-3-trimethylsilanylmethyl-3H-[1,2,3]triazole-4-carboxylic acid ethyl ester To a solution of pyridin-2-yl-propynoic acid ethyl ester (1.25 g, 7.14 mmol) in benzene (22 mL) was added azidomethyl-trimethyl-silane (1.11 g, 8.56 mmol) and the reaction mixture was refluxed under nitrogen for 72 h. The mixture was then evaporated and purification by chromatography [silica, 0 to 50% ethyl acetate in heptane then HPLC (Chiralpak AD, ethanol in heptane)] afforded the title compound (477 mg, 23%) as a yellow oil. MS: m/e=305.2 [M+H]+.

d) (5-Pyridin-2-yl-3-trimethylsilanylmethyl-3H-[1,2,3]-triazol-4-yl)-methanol To a solution of 5-pyridin-2-yl-3-trimethylsilanylmethyl-3H-[1,2,3]triazole-4-carboxylic acid ethyl ester (1.67 g, 5.49 mmol) in dry THF (17 mL) was added portionwise lithiumaluminiumhydride (0.24 g, 6.31 mmol) at 0° C. and the reaction mixture was stirred at 0° C. for 1 h. Then water (240 µL) and NaOH (15%, 240 µL) was added followed by water (720 µL). The precipitate was then filtered off and the filtrate evaporated. Purification by chromatography (silica, 0 to 10% methanol in dichloromethane) afforded the title compound (379 mg, 26%) as a white solid. MS: m/e=263.1 [M+H]+.

e) (3-Methyl-5-pyridin-2-yl-3H-[1,2,3]-triazol-4-yl)-methanol

To a solution of (5-pyridin-2-yl-3-trimethylsilanylmethyl-3H-[1,2,3]triazol-4-yl)-methanol (364 mg, 1.39 mmol) in THF (23 mL) was added water (50 µL, 2.78 mmol) and then tetrabutylammonium fluoride (1 M in THF, 1.66 mL, 1.66 mmol) added dropwise at 0° C. The reaction mixture was stirred at 0° C. for 15 min. The resulting mixture was poured into water and then the THF was evaporated. The aqueous layer was then extracted with ethyl acetate and the combined organic extracts washed with brine, dried over sodium sulphate, filtered and evaporated. Purification by chromatography (silica, 0 to 100% ethyl acetate in heptane) afforded the title compound (161 mg, 61%) as an off white solid. MS: m/e=191.2 [M+H]+.

f) 6-(3-Methyl-5-pyridin-2-yl-3H-[1,2,3]-triazol-4-ylmethoxy)-nicotinic acid methyl ester A solution of (3-methyl-5-pyridin-2-yl-3H-[1,2,3]triazol-4-yl)-methanol (158 mg, 0.83 mmol) in THF (2.4 mL) was added dropwise at 0° C. to a suspension of NaH (60% in oil, 40 mg, 0.91 mmol) in THF (1.2 mL) and the reaction mixture was then stirred at room temperature for 30 min. Then a solution of methyl 6-chloronicotinate (157 mg, 0.91 mmol) in THF (2.4 mL) was added dropwise at 0° C. and the reaction mixture stirred at room temperature for 18 h. The mixture was then poured into water extracted with ethyl acetate and the combined organic extracts washed with brine, dried over sodium sulphate, filtered and evaporated. Purification by chromatography (silica, 0 to 100% ethyl acetate in heptane) afforded the title compound (209 mg, 77%) as a white solid. MS: m/e=326.1 [M+H]+.

Example 26

6-(3-Methyl-5-pyridin-2-yl-3H-[1,2,3]triazol-4-yl-methoxy)-N-(tetrahydro-pyran-4-yl)-nicotinamide

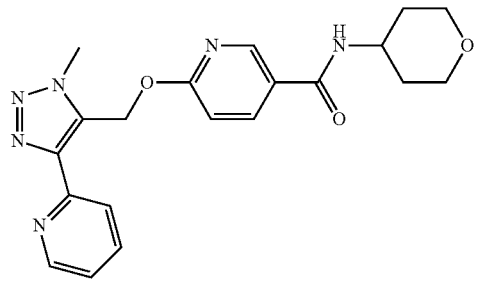 [SMILES: Cn1nnc(-c2ccccn2)c1COc1ccc(C(=O)NC2CCOCC2)cn1]

a) 6-(3-Methyl-5-pyridin-2-yl-3H-[1,2,3]triazol-4-ylmethoxy)-nicotinic acid

A solution of lithium hydroxide monohydrate (51 mg, 1.22 mmol) in water (1.5 mL) was added dropwise to a suspension of 6-(3-methyl-5-pyridin-2-yl-3H-[1,2,3]triazol-4-yl-methoxy)-nicotinic acid methyl ester (199 mg, 0.61 mmol) in THF (1.5 mL) and MeOH (0.3 mL). The reaction mixture was then stirred at room temperature for 2 h. The reaction mixture was then evaporated and the residue dissolved in water, acidified with HCl (1N), and the resulting precipitate filtered off to afford the title product (162 mg, 70%) as a white solid. MS: m/e=310.3 [M−H]−.

b) 6-(3-Methyl-5-pyridin-2-yl-3H-[1,2,3]triazol-4-ylmethoxy)-N-(tetrahydro-pyran-4-yl)-nicotinamide To a solution of 6-(3-methyl-5-pyridin-2-yl-3H-[1,2,3]triazol-4-ylmethoxy)-nicotinic acid (76 mg, 0.24 mmol) and TBTU (86 mg, 0.27 mmol) in DMF (1.2 mL) was added DIPEA (209 µL, 1.22 mmol). Then 4-aminotetrahydropyran (27 mg, 0.27 mmol) was added and the mixture was stirred at room temperature under Ar for 1 h. The mixture was then evaporated and purification by chromatography (silica, 50 to 100% ethyl acetate in heptane) afforded the title compound (67 mg, 70%) as a white solid after recrystallisation from methanol/water. MS: m/e=395.1 [M+H]+.

Example 27

N-Isopropyl-6-(3-methyl-5-pyridin-2-yl-3H-[1,2,3]triazol-4-ylmethoxy)-nicotinamide

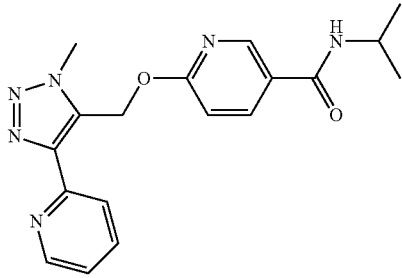

As described for example 26b, 6-(3-methyl-5-pyridin-2-yl-3H-[1,2,3]triazol-4-ylmethoxy)-nicotinic acid (76 mg, 0.24 mmol) was converted, using isopropylamine instead of 4-aminotetrahydropyran, to the title compound (61 mg, 71%) which was obtained as a white solid. MS: m/e=353.2 [M+H]$^+$.

Example 28

N-(2-Hydroxy-1,1-dimethyl-ethyl)-6-(3-methyl-5-pyridin-2-yl-3H-[1,2,3]triazol-4-ylmethoxy)-nicotinamide

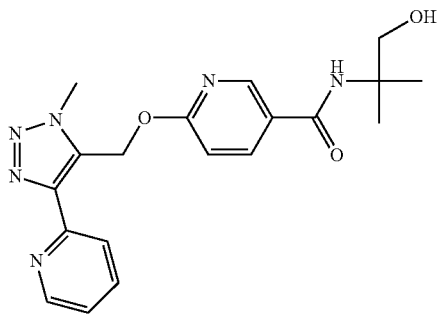 [SMILES: Cn1nnc(-c2ccccn2)c1COc1ccc(C(=O)NC(C)(C)CO)cn1]

As described for example 26b, 6-(3-methyl-5-pyridin-2-yl-3H-[1,2,3]triazol-4-ylmethoxy)-nicotinic acid (80 mg, 0.26 mmol) was converted, using 2-amino-2-methyl-1-propanol instead of 4-aminotetrahydropyran, to the title compound (78 mg, 79%) which was obtained as a white solid. MS: m/e=383.2 [M+H]$^+$.

Example 29

N-(2-Hydroxy-ethyl)-6-(3-methyl-5-pyridin-2-yl-3H-[1,2,3]triazol-4-ylmethoxy)-nicotinamide

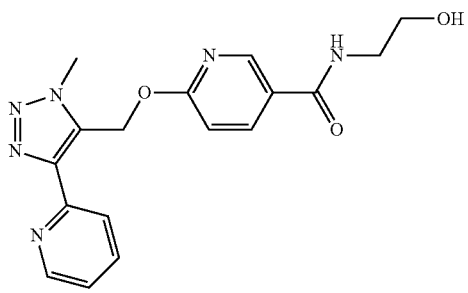

As described for example 26b, 6-(3-methyl-5-pyridin-2-yl-3H-[1,2,3]triazol-4-ylmethoxy)-nicotinic acid (80 mg, 0.26 mmol) was converted, using ethanolamine instead of 4-aminotetrahydropyran, to the title compound (82 mg, 90%) which was obtained as an off white solid. MS: m/e=355.2 [M+H]$^+$.

Example 30

N-(3-Methyl-oxetan-3-yl)-6-(3-methyl-5-pyridin-2-yl-3H-[1,2,3]triazol-4-ylmethoxy)-nicotinamide

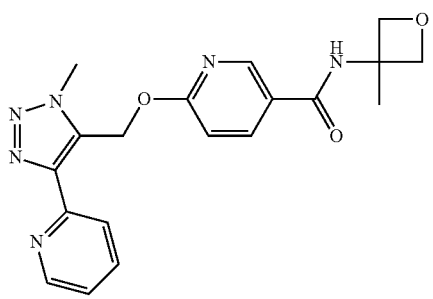 [SMILES: Cn1nnc(-c2ccccn2)c1COc1ccc(C(=O)NC2(C)COC2)cn1]

As described for example 26b, 6-(3-methyl-5-pyridin-2-yl-3H-[1,2,3]triazol-4-ylmethoxy)-nicotinic acid (80 mg, 0.26 mmol) was converted, using 3-methyl-3-oxetanamine instead of 4-aminotetrahydropyran, to the title compound (91 mg, 93%) which was obtained as an off white solid. MS: m/e=381.2 [M+H]$^+$.

Example 31

6-(3-Methyl-5-pyridin-2-yl-3H-[1,2,3]triazol-4-ylmethoxy)-N-morpholin-4-yl-nicotinamide

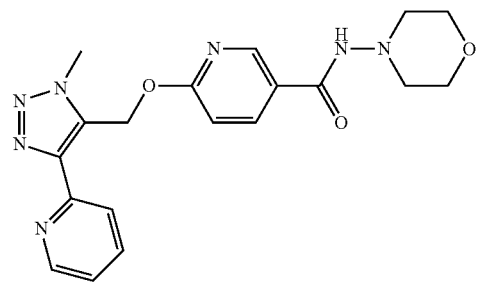 [SMILES: Cn1nnc(-c2ccccn2)c1COc1ccc(C(=O)NN2CCOCC2)cn1]

As described for example 26b, 6-(3-methyl-5-pyridin-2-yl-3H-[1,2,3]triazol-4-ylmethoxy)-nicotinic acid (75 mg, 0.24 mmol) was converted, using N-aminomorpholine instead of 4-aminotetrahydropyran, to the title compound (74 mg, 78%) which was obtained as a white solid. MS: m/e=396.3 [M+H]$^+$.

Example 32

6-(3-Methyl-5-pyridin-2-yl-3H-[1,2,3]triazol-4-yl-methoxy)-nicotinic acid N,N'-dimethyl-hydrazide

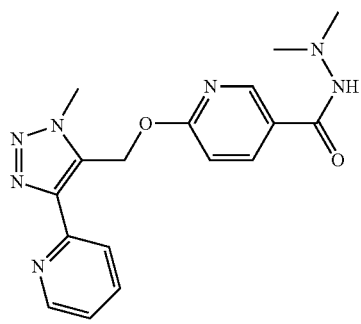 [SMILES: CN(C)NC(=O)c1ccc(OCc2c(-c3ccccn3)nnn2C)nc1]

As described for example 26b, 6-(3-methyl-5-pyridin-2-yl-3H-[1,2,3]triazol-4-ylmethoxy)-nicotinic acid (75 mg, 0.24 mmol) was converted, using N,N-dimethylhydrazine instead of 4-aminotetrahydropyran, to the title compound (65 mg, 76%) which was obtained as an off white solid. MS: m/e=396.3 [M+H]$^+$.

Example 33

6-(3-Methyl-5-pyridin-2-yl-3H-[1,2,3]triazol-4-yl-methoxy)-N-(3,3,3-trifluoro-2-hydroxy-propyl)-nicotinamide

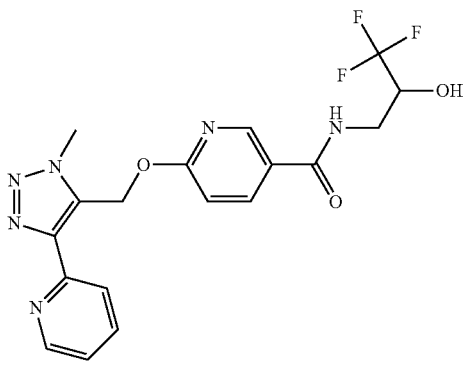 [SMILES: Cn1nnc(-c2ccccn2)c1COc1ccc(C(=O)NCC(O)C(F)(F)F)cn1]

As described for example 26b, 6-(3-methyl-5-pyridin-2-yl-3H-[1,2,3]triazol-4-ylmethoxy)-nicotinic acid (75 mg, 0.24 mmol) was converted, using 3-amino-1,1,1-trifluoro-2-propanol instead of 4-aminotetrahydropyran, to the title compound (63 mg, 62%) which was obtained as a white solid. MS: m/e=423.1 [M+H]$^+$.

Example 34

6-[5-(5-Fluoro-pyridin-2-yl)-3-methyl-3H-[1,2,3]triazol-4-ylmethoxy]-nicotinic acid methyl ester

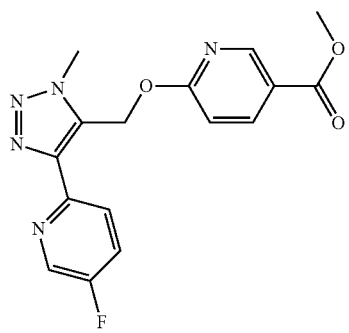 [SMILES: COC(=O)c1ccc(OCc2c(-c3ccc(F)cn3)nnn2C)nc1]

a) 2-Ethynyl-5-fluoro-pyridine

To a mixture of 5-fluoro-2-formylpyridine (1.10 g, 9.0 mmol) in MeOH (38 mL) was added potassium carbonate (2.44 g, 0.018 mol) followed by a solution of (1-diazo-2-oxo-propyl)-phosphonic acid dimethyl ester (2.03 g, 11 mmol) in MeOH (12 mL). The mixture was stirred at room temperature for 90 min, then extracted with diethylether. The organic layers were then washed with sodium hydrogen carbonate solution (1 M) and brine, dried over sodium sulfate, filtered and evaporated at to give the title compound (1.01 g, 78%) as a light brown liquid. MS: m/e=121.0 [M]$^+$.

b) (5-Fluoro-pyridin-2-yl)-propynoic acid ethyl ester

As described for example 25b, 2-ethynyl-5-fluoro-pyridine (990 mg, 8.0 mmol), instead of 2-ethynyl-pyridine, was converted to the title compound (1.18 g, 75%) which was obtained as a light yellow solid. MS: m/e=194.1 [M+H]$^+$.

c) 5-(5-Fluoro-pyridin-2-yl)-3-trimethylsilanylmethyl-3H-[1,2,3]triazole-4-carboxylic acid ethyl ester As described for example 25c, (5-fluoro-pyridin-2-yl)-propynoic acid ethyl ester (1.69 g, 9.0 mmol), instead of pyridin-2-yl-propynoic acid ethyl ester, was converted to the title compound (776 mg, 28%) which was obtained as a light yellow solid. MS: m/e=323.1 [M+H]$^+$.

d) [5-(5-Fluoro-pyridin-2-yl)-3-trimethylsilanylmethyl-3H-[1,2,3]triazol-4-yl]-methanol To a solution of 5-(5-fluoro-pyridin-2-yl)-3-trimethylsilanylmethyl-3H-[1,2,3]triazole-4-carboxylic acid ethyl ester (530 mg, 1.64 mmol) in toluene (15 mL) at −7° C. was added sodiumdihydro-bis(2-methoxyethoxy)aluminate (705 μL, 2.47 mmol) and the reaction mixture was stirred at room temperature for 16 h. The mixture was then cooled with ice and NaOH (1 N, 3.3 mL) and extracted with ethyl acetate and the combined organic extracts washed with brine, dried over sodium sulphate, filtered and evaporated to afford the title compound (440 mg, 84%) as a light brown oil. MS: m/e=281.1 [M+H]+.

e) [5-(5-Fluoro-pyridin-2-yl)-3-methyl-3H-[1,2,3] triazol-4-yl]-methanol

As described for example 25e, [5-(5-fluoro-pyridin-2-yl)-3-trimethylsilanylmethyl-3H-[1,2,3]triazol-4-yl]-methanol (421 mg, 1.5 mmol), instead of (5-pyridin-2-yl-3-trimethyl-silanylmethyl-3H-[1,2,3]triazol-4-yl)-methanol, was converted to the title compound (257 mg, 82%) which was obtained as a white solid. MS: m/e=209.1 [M+H]+.

f) 6-[5-(5-Fluoro-pyridin-2-yl)-3-methyl-3H-[1,2,3] triazol-4-ylmethoxy]-nicotinic acid methyl ester As described for example 25f, [5-(5-fluoro-pyridin-2-yl)-3-methyl-3H-[1,2,3]triazol-4-yl]-methanol (285 mg, 1.4 mmol), instead of (3-methyl-5-pyridin-2-yl-3H-[1,2,3]triazol-4-yl)-methanol, was converted to the title compound (420 mg, 76%) which was obtained as a white solid. MS: m/e=344.0 [M+H]+.

Example 35

6-[5-(5-Fluoro-pyridin-2-yl)-3-methyl-3H-[1,2,3] triazol-4-ylmethoxy]-N-(tetrahydro-pyran-4-yl)-nicotinamide

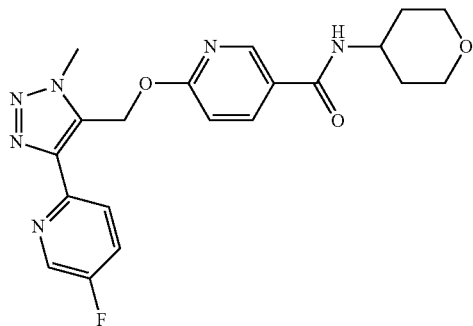

a) 6-[5-(5-Fluoro-pyridin-2-yl)-3-methyl-3H-[1,2,3] triazol-4-ylmethoxy]-nicotinic acid As described for example 26a, 6-[5-(5-fluoro-pyridin-2-yl)-3-methyl-3H-[1,2,3]triazol-4-ylmethoxy]-nicotinic acid methyl ester (396 mg, 0.8 mmol), instead of 6-(3-methyl-5-pyridin-2-yl-3H-[1,2,3]triazol-4-ylmethoxy)-nicotinic acid methyl ester, was converted to the title compound (270 mg, 81%) which was obtained as a white solid. MS: m/e=328.3 [M−H]−.

b) 6-[5-(5-Fluoro-pyridin-2-yl)-3-methyl-3H-[1,2,3] triazol-4-ylmethoxy]-N-(tetrahydro-pyran-4-yl)-nicotinamide As described for example 26b, 6-[5-(5-fluoro-pyridin-2-yl)-3-methyl-3H-[1,2,3]triazol-4-ylmethoxy]-nicotinic acid (82 mg, 0.25 mmol), instead of 6-(3-methyl-5-pyridin-2-yl-3H-[1,2,3]triazol-4-ylmethoxy)-nicotinic acid, was converted to the title compound (80 mg, 78%) which was obtained as a white solid. MS: m/e=413.4 [M+H]+.

Example 36

6-[5-(5-Fluoro-pyridin-2-yl)-3-methyl-3H-[1,2,3] triazol-4-ylmethoxy]-N-isopropyl-nicotinamide

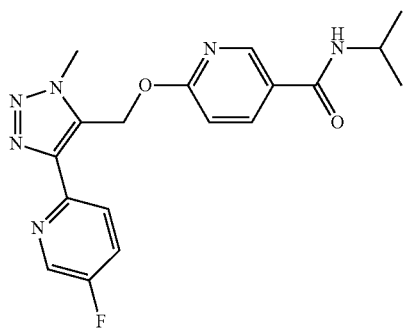

As described for example 35b, 6-[5-(5-fluoro-pyridin-2-yl)-3-methyl-3H-[1,2,3]triazol-4-ylmethoxy]-nicotinic acid (82 mg, 0.25 mmol) was converted, using isopropylamine instead of 4-aminotetrahydropyran, to the title compound (38 mg, 41%) which was obtained as a white solid. MS: m/e=371.1 [M+H]+.

Example 37

6-[5-(5-Fluoro-pyridin-2-yl)-3-methyl-3H-[1,2,3] triazol-4-ylmethoxy]-N-(2-hydroxy-1,1-dimethyl-ethyl)-nicotinamide

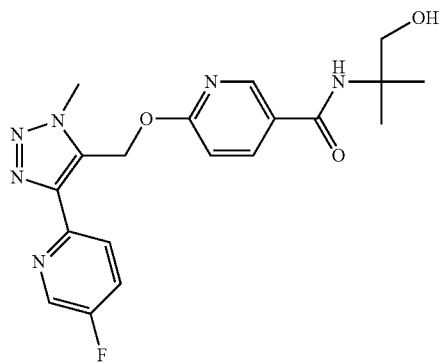

As described for example 35b, 6-[5-(5-fluoro-pyridin-2-yl)-3-methyl-3H-[1,2,3]triazol-4-ylmethoxy]-nicotinic acid (80 mg, 0.24 mmol) was converted, using 2-amino-2-methyl-1-propanol instead of 4-aminotetrahydropyran, to the title compound (94 mg, 97%) which was obtained as a white solid. MS: m/e=401.3 [M+H]+.

Example 38

6-[5-(5-Fluoro-pyridin-2-yl)-3-methyl-3H-[1,2,3]triazol-4-ylmethoxy]-N-(3-methyl-oxetan-3-yl)-nicotinamide

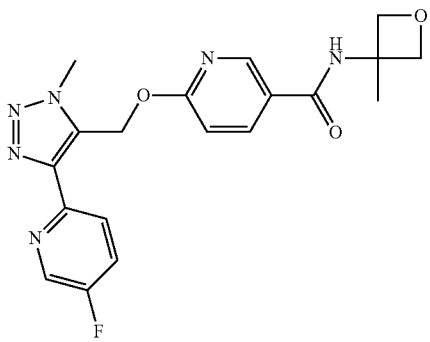 [SMILES: Cn1nnc(-c2ccc(F)cn2)c1COc1ccc(C(=O)NC2(C)COC2)cn1]

As described for example 35b, 6-[5-(5-fluoro-pyridin-2-yl)-3-methyl-3H-[1,2,3]triazol-4-ylmethoxy]-nicotinic acid (80 mg, 0.24 mmol) was converted, using 3-methyl-3-oxetanamine instead of 4-aminotetrahydropyran, to the title compound (88 mg, 91%) which was obtained as a white solid. MS: m/e=399.2 [M+H]$^+$.

Example 39

6-[5-(5-Fluoro-pyridin-2-yl)-3-methyl-3H-[1,2,3]triazol-4-ylmethoxy]-N-morpholin-4-yl-nicotinamide

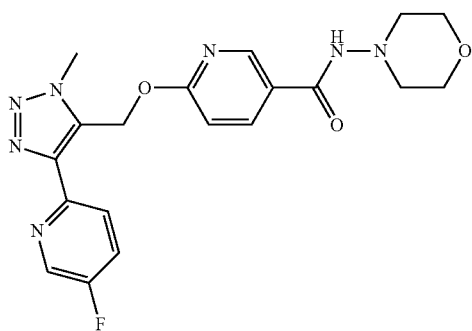

As described for example 35b, 6-[5-(5-fluoro-pyridin-2-yl)-3-methyl-3H-[1,2,3]triazol-4-ylmethoxy]-nicotinic acid (80 mg, 0.24 mmol) was converted, using 4-aminomorpholine instead of 4-aminotetrahydropyran, to the title compound (87 mg, 87%) which was obtained as a white solid. MS: m/e=414.4 [M+H]$^+$.

Example 40

5-[5-(5-Fluoro-pyridin-2-yl)-3-methyl-3H-[1,2,3]triazol-4-ylmethoxy]-pyridine-2-carboxylic acid isopropylamide

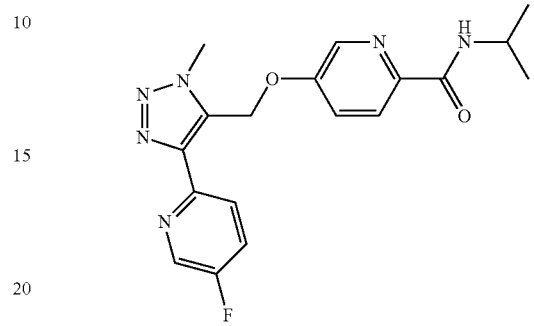

a) 5-[5-(5-Fluoro-pyridin-2-yl)-3-methyl-3H-[1,2,3]triazol-4-ylmethoxy]-pyridine-2-carboxylic acid ethyl ester To a solution of [5-(5-fluoro-pyridin-2-yl)-3-methyl-3H-[1,2,3]triazol-4-yl]-methanol (416 mg, 2.0 mmol), 5-hydroxy-pyridine-2-carboxylic acid ethyl ester (362 mg, 2.60 mmol) and triphenylphosphine (682 mg, 2.6 mmol) in THF (10 mL) was added diethyl azodicarboxylate (40% in toluene, 1.19 mL, 2.6 mmol) dropwise at 0° C. The reaction mixture was then stirred at room temperature for 1 h and then evaporated. Purification by chromatography (silica, 50 to 100% ethyl acetate in heptane) afforded the title compound (386 mg, 77%) as a white solid after recrystallisation from ethyl acetate. MS: m/e=358.3 [M+H]$^+$.

b) 5-[5-(5-Fluoro-pyridin-2-yl)-3-methyl-3H-[1,2,3]-triazol-4-ylmethoxy]-pyridine-2-carboxylic acid A solution of lithium hydroxide monohydrate (59 mg, 1.41 mmol) in water (1.8 mL) was added dropwise to a suspension of 5-[5-(5-fluoro-pyridin-2-yl)-3-methyl-3H-[1,2,3]triazol-4-ylmethoxy]-pyridine-2-carboxylic acid ethyl ester (252 mg, 0.71 mmol) in THF (1.8 mL) and MeOH (0.4 mL). The reaction mixture was then stirred at room temperature for 2 h. The reaction mixture was then evaporated and the residue dissolved in water, acidified with HCl (1N), and the resulting precipitate filtered off to afford the title product (180 mg, 78%) as a white solid after trituration with ethyl acetate. MS: m/e=330.1 [M+H]$^+$.

c) 5-[5-(5-Fluoro-pyridin-2-yl)-3-methyl-3H-[1,2,3]triazol-4-ylmethoxy]-pyridine-2-carboxylic acid isopropylamide To a solution of 5-[5-(5-fluoro-pyridin-2-yl)-3-methyl-3H-[1,2,3]triazol-4-ylmethoxy]-pyridine-2-carboxylic acid (82 mg, 0.25 mmol) and TBTU (88 mg, 0.27 mmol) in DMF (1.2 mL) was added DIPEA (213 µL, 1.25 mmol). Then isopropylamine (23 µL, 0.27 mmol) was added and the mixture was stirred at room temperature under Ar for 1 h. The mixture was then evaporated and purification by chromatography (silica, 50 to 100% ethyl acetate in heptane) afforded the title compound (57 mg, 62%) as a white solid after recrystallisation from ethyl acetate/heptane. MS: m/e=371.1 [M+H]⁺.

Example 41

6-[5-(4-Fluoro-phenyl)-3-methyl-3H-[1,2,3]triazol-4-ylmethoxy]-pyridazine-3-carboxylic acid ethyl ester

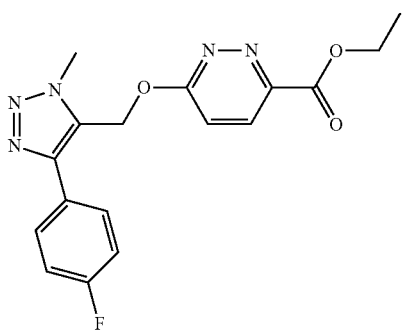 [SMILES: CCOC(=O)c1ccc(OCc2c(-c3ccc(F)cc3)nnn2C)nn1]

a) 3-Chloro-6-[5-(4-fluoro-phenyl)-3-methyl-3H-[1,2,3]triazol-4-ylmethoxy]-pyridazine To a suspension of sodium hydride (55%, 93 mg, 2.11 mmol) in THF (3 mL) a solution of (3-methyl-5-phenyl-3H-[1,2,3]triazol-4-yl)-methanol (400 mg, 2.11 mmol) in THF (5 mL) was added under ice cooling. After the addition was complete the mixture was allowed to warm up to room temperature and stirred for 30 min. Again under ice cooling a solution of 3,6-dichloropyridazine (357 mg, 2.11 mmol) in THF (5 mL) was added and the reaction mixture stirred at room temperature for 16 h. The mixture was then poured into ice water and extracted with ethyl acetate and the combined organic extracts washed with brine, dried over sodium sulphate, filtered and evaporated. Purification by chromatography (silica, 0 to 50% ethyl acetate in heptane) afforded the title compound (580 mg, 90%) as a white solid. MS: m/e=302.2 [M+H]⁺.

b) 6-[5-(4-Fluoro-phenyl)-3-methyl-3H-[1,2,3]triazol-4-ylmethoxy]-pyridazine-3-carboxylic acid ethyl ester To a suspension of 3-chloro-6-[5-(4-fluoro-phenyl)-3-methyl-3H-[1,2,3]triazol-4-ylmethoxy]-pyridazine (558 mg, 1.75 mmol) in ethanol (8 mL) was added sodium carbonate (185 mg, 1.745 mmol) followed by 1,1'-bis(diphenylphosphino) ferrocene (97 mg, 0.18 mmol) and palladium(II) acetate (40 mg, 0.18 mmol). The reaction flask was filled with Ar three times after a short evacuation. The fourth time the flask was flushed with CO-gas (balloon). The mixture was stirred under CO atmosphere at 50° C. over night, then cooled to room temperature and filtered over dicalite and washed well with DCM. The filtrate was then evaporated. Purification by chromatography (silica, 0 to 50% ethyl acetate in heptane) afforded the title compound (500 mg, 80%) as an off white solid. MS: m/e=358.2 [M+H]⁺.

Example 42

6-[5-(4-Fluoro-phenyl)-3-methyl-3H-[1,2,3]triazol-4-ylmethoxy]-pyridazine-3-carboxylic acid (tetrahydro-pyran-4-yl)-amide

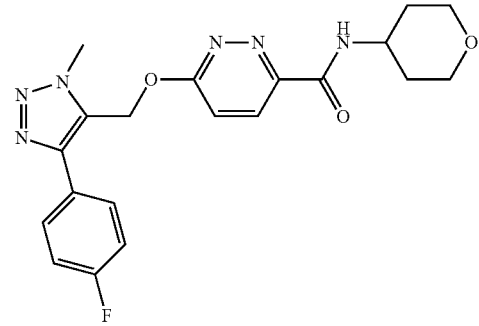 [SMILES: Cn1nnc(-c2ccc(F)cc2)c1COc1ccc(C(=O)NC2CCOCC2)nn1]

a) 6-[5-(4-Fluoro-phenyl)-3-methyl-3H-[1,2,3]triazol-4-ylmethoxy]-pyridazine-3-carboxylic acid A solution of lithium hydroxide monohydrate (111 mg, 3.09 mmol) in water (5 mL) was added dropwise to a suspension of 6-[5-(4-fluoro-phenyl)-3-methyl-3H-[1,2,3]triazol-4-ylmethoxy]-pyridazine-3-carboxylic acid ethyl ester (471 mg, 1.32 mmol) in THF (5 mL). The reaction mixture was then stirred at room temperature for 16 h. The reaction mixture was then evaporated and the residue dissolved in water, acidified with HCl (1N), and the resulting precipitate filtered off to afford the title product (430 mg, 99%) as a white solid after trituration with ethyl acetate. MS: m/e=328.3 [M−H]⁻.

b) 6-[5-(4-Fluoro-phenyl)-3-methyl-3H-[1,2,3]triazol-4-ylmethoxy]-pyridazine-3-carboxylic acid (tetrahydro-pyran-4-yl)-amide To a solution of 6-[5-(4-fluoro-phenyl)-3-methyl-3H-[1,2,3]triazol-4-ylmethoxy]-pyridazine-3-carboxylic acid (67 mg, 0.20 mmol) and TBTU (72 mg, 0.22 mmol) in DMF (2 mL) was added DIPEA (175 µL, 1.0 mmol). Then 4-aminotetrahydropyran (23 mg, 0.22 mmol) was added and the mixture was stirred at room temperature under Ar for 16 h. The mixture was then evaporated and purification by chromatography (silica, 50 to 100% ethyl acetate in heptane) afforded the title compound (62 mg, 73%) as an off white solid. MS: m/e=413.3 [M+H]⁺.

Example 43

6-[5-(4-Fluoro-phenyl)-3-methyl-3H-[1,2,3]triazol-4-ylmethoxy]-pyridazine-3-carboxylic acid isopropylamide

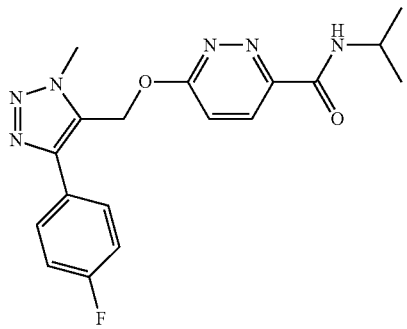 [SMILES: CC(C)NC(=O)c1ccc(OCc2c(-c3ccc(F)cc3)nnn2C)nn1]

As described for example 42b, 6-[5-(4-fluoro-phenyl)-3-methyl-3H-[1,2,3]triazol-4-ylmethoxy]-pyridazine-3-carboxylic acid (67 mg, 0.20 mmol) was converted, using isopropylamine instead of 4-aminotetrahydropyran, to the title compound (44 mg, 58%) which was obtained as a white solid. MS: m/e=371.1 [M+H]+.

Example 44

6-[5-(4-Fluoro-phenyl)-3-methyl-3H-[1,2,3]triazol-4-ylmethoxy]-pyridazine-3-carboxylic acid (2-hydroxy-1,1-dimethyl-ethyl)-amide

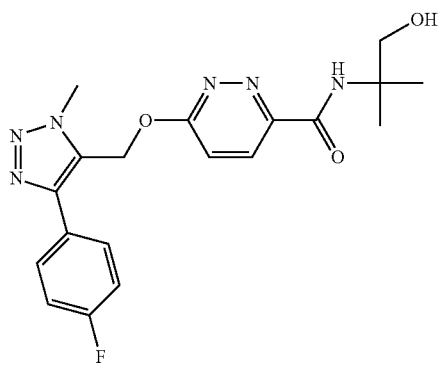 [SMILES: Cn1nnc(-c2ccc(F)cc2)c1COc1ccc(C(=O)NC(C)(C)CO)nn1]

As described for example 42b, 6-[5-(4-fluoro-phenyl)-3-methyl-3H-[1,2,3]triazol-4-ylmethoxy]-pyridazine-3-carboxylic acid (67 mg, 0.20 mmol) was converted, using 2-amino-2-methyl-1-propanol instead of 4-aminotetrahydropyran, to the title compound (37 mg, 40%) which was obtained as a white solid. MS: m/e=401.3 [M+H]+.

Example 45

6-[5-(4-Fluoro-phenyl)-3-methyl-3H-[1,2,3]triazol-4-ylmethoxy]-pyridazine-3-carboxylic acid morpholin-4-ylamide

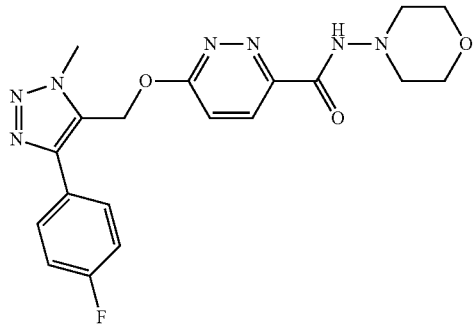 [SMILES: Cn1nnc(-c2ccc(F)cc2)c1COc1ccc(C(=O)NN2CCOCC2)nn1]

As described for example 42b, 6-[5-(4-fluoro-phenyl)-3-methyl-3H-[1,2,3]triazol-4-ylmethoxy]-pyridazine-3-carboxylic acid (67 mg, 0.20 mmol) was converted, using 4-aminomorpholine instead of 4-aminotetrahydropyran, to the title compound (25 mg, 29%) which was obtained as a white solid. MS: m/e=414.3 [M+H]+.

Example 46

3-Chloro-6-(3-methyl-5-pyridin-2-yl-3H-[1,2,3]triazol-4-ylmethoxy)-pyridazine

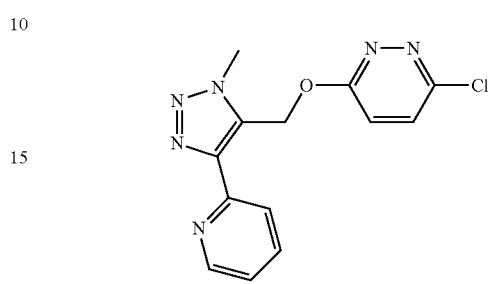

To a suspension of sodium hydride (55%, 92 mg, 2.10 mmol) in THF (3 mL) was added a solution of (3-methyl-5-pyridin-2-yl-3H-[1,2,3]triazol-4-yl)-methanol (400 mg, 2.103 mmol) in THF (5 mL) under ice cooling. The mixture was then allowed to warm up to room temperature and stirred for 30 min. Again under ice cooling was added a solution of 3,6-dichloropyridazine (315 mg, 2.10 mmol) in THF (5 mL) and the resulting mixture stirred at room temperature for 16 h. The mixture was then poured into ice water and extracted with ethyl acetate and the combined organic extracts washed with brine, dried over sodium sulphate, filtered and evaporated. Purification by chromatography (silica, 0 to 50% ethyl acetate in heptane) afforded the title compound (630 mg, 99%) as a white solid. MS: m/e=303.0 [M+H]+.

Example 47

6-(3-Methyl-5-pyridin-2-yl-3H-[1,2,3]triazol-4-ylmethoxy)-pyridazine-3-carboxylic acid ethyl ester

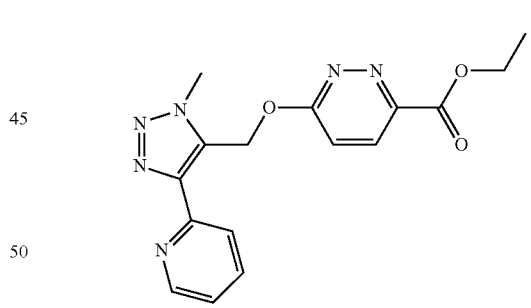

To a suspension of 3-chloro-6-(3-methyl-5-pyridin-2-yl-3H-[1,2,3]triazol-4-ylmethoxy)-pyridazine (620 mg, 2.05 mmol) in ethanol (10 mL) was added sodium carbonate (220 mg, 2.05 mmol) followed by 1,1'-bis(diphenylphosphino)ferrocene (115 mg, 0.21 mmol) and palladium(II) acetate (46 mg, 0.21 mmol). The reaction flask was filled with Ar three times after a short evacuation. The fourth time the flask was flushed with CO-gas (balloon). The mixture was stirred under CO atmosphere at 50° C. over night, then cooled to room temperature and filtered over dicalite and washed well with DCM. The filtrate was then evaporated. Purification by chromatography (silica, 0 to 50% ethyl acetate in heptane) afforded the title compound (582 mg, 84%) as an off white solid. MS: m/e=341.1 [M+H]+.

Example 48

6-(3-Methyl-5-pyridin-2-yl-3H-[1,2,3]triazol-4-yl-methoxy)-pyridazine-3-carboxylic acid (tetrahydro-pyran-4-yl)-amide

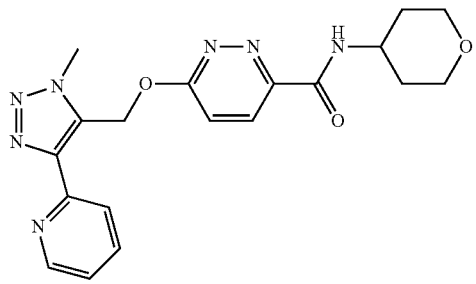 [SMILES: Cn1nnc(-c2ccccn2)c1COc1ccc(C(=O)NC2CCOCC2)nn1]

a) 6-(3-Methyl-5-pyridin-2-yl-3H-[1,2,3]triazol-4-ylmethoxy)-pyridazine-3-carboxylic acid A solution of lithium hydroxide monohydrate (130 mg, 3.06 mmol) in water (5 mL) was added dropwise to a suspension of 6-(3-methyl-5-pyridin-2-yl-3H-[1,2,3]triazol-4-yl-methoxy)-pyridazine-3-carboxylic acid ethyl ester (521 mg, 1.53 mmol) in THF (5 mL) and MeOH (0.5 mL). The reaction mixture was then stirred at room temperature for 2 h. The reaction mixture was then evaporated and the residue dissolved in water, acidified with HCl (1N), and the resulting precipitate filtered off to afford the title product (320 mg, 67%) as a white solid. MS: m/e=311.2 [M−H]⁻.

b) 6-(3-Methyl-5-pyridin-2-yl-3H-[1,2,3]triazol-4-ylmethoxy)-pyridazine-3-carboxylic acid (tetrahydro-pyran-4-yl)-amide To a solution of 6-(3-methyl-5-pyridin-2-yl-3H-[1,2,3]triazol-4-ylmethoxy)-pyridazine-3-carboxylic acid (98 mg, 0.31 mmol) and TBTU (111 mg, 0.35 mmol) in DMF (2 mL) was added DIPEA (270 µL, 1.57 mmol). Then 4-aminotetrahydropyran (35 mg, 0.35 mmol) was added and the mixture was stirred at room temperature under Ar for 16 h. The mixture was then evaporated and purification by chromatography (silica, 50 to 100% ethyl acetate in heptane) afforded the title compound (101 mg, 81%) as an off white solid. MS: m/e=396.2 [M+H]⁺.

Example 49

6-(3-Methyl-5-pyridin-2-yl-3H-[1,2,3]triazol-4-yl-methoxy)-pyridazine-3-carboxylic acid isopropylamide

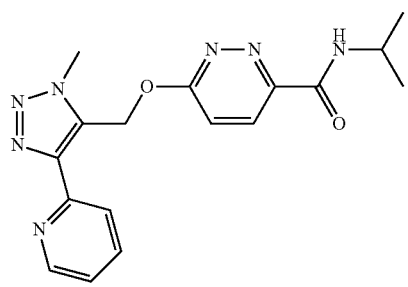 [SMILES: CC(C)NC(=O)c1ccc(OCc2c(-c3ccccn3)nnn2C)nn1]

As described for example 48b, 6-(3-methyl-5-pyridin-2-yl-3H-[1,2,3]triazol-4-ylmethoxy)-pyridazine-3-carboxylic acid (98 mg, 0.31 mmol) was converted, using isopropylamine instead of 4-aminotetrahydropyran, to the title compound (101 mg, 91%) which was obtained as an off white solid. MS: m/e=354.2 [M+H]⁺.

Example 50

3-Chloro-6-[5-(5-fluoro-pyridin-2-yl)-3-methyl-3H-[1,2,3]triazol-4-ylmethoxy]-pyridazine

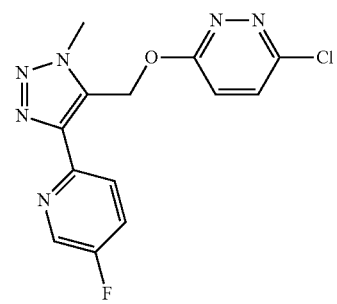 [SMILES: Cn1nnc(-c2ccc(F)cn2)c1COc1ccc(Cl)nn1]

As described for example 46, [5-(5-fluoro-pyridin-2-yl)-3-methyl-3H-[1,2,3]triazol-4-yl]-methanol (400 mg, 1.92 mmol), instead of (3-methyl-5-pyridin-2-yl-3H-[1,2,3]triazol-4-yl)-methanol, was converted to the title compound (563 mg, 91%) which was obtained as a white solid. MS: m/e=321.1 [M+H]⁺.

Example 51

6-[5-(5-Fluoro-pyridin-2-yl)-3-methyl-3H-[1,2,3]triazol-4-ylmethoxy]-pyridazine-3-carboxylic acid (2-hydroxy-1,1-dimethyl-ethyl)-amide

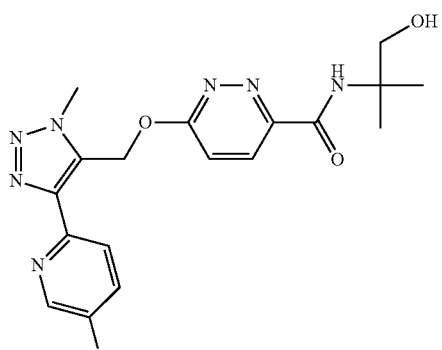

a) 6-[5-(5-Fluoro-pyridin-2-yl)-3-methyl-3H-[1,2,3]triazol-4-ylmethoxy]-pyridazine-3-carboxylic acid ethyl ester As described for example 47, 3-chloro-6-[5-(5-fluoro-pyridin-2-yl)-3-methyl-3H-[1,2,3]triazol-4-ylmethoxy]-pyridazine (532 mg, 1.66 mmol), instead of 3-chloro-6-(3-methyl-5-pyridin-2-yl-3H-[1,2,3]triazol-4-ylmethoxy)-pyridazine, was converted to the title compound (531 mg, 89%) which was obtained as a white solid. MS: m/e=359.1 [M+H]+.

b) 6-[5-(5-Fluoro-pyridin-2-yl)-3-methyl-3H-[1,2,3]triazol-4-ylmethoxy]-pyridazine-3-carboxylic acid As described for example 48a, 6-[5-(5-fluoro-pyridin-2-yl)-3-methyl-3H-[1,2,3]triazol-4-ylmethoxy]-pyridazine-3-carboxylic acid ethyl ester (500 mg, 1.40 mmol), instead of 6-(3-methyl-5-pyridin-2-yl-3H-[1,2,3]triazol-4-ylmethoxy)-pyridazine-3-carboxylic acid ethyl ester, was converted to the title compound (424 mg, 92%) which was obtained as an off white solid. MS: m/e=329.1 [M−H]−.

c) 6-[5-(5-Fluoro-pyridin-2-yl)-3-methyl-3H-[1,2,3]triazol-4-ylmethoxy]-pyridazine-3-carboxylic acid (2-hydroxy-1,1-dimethyl-ethyl)-amide To a solution of 6-[5-(5-fluoro-pyridin-2-yl)-3-methyl-3H-[1,2,3]triazol-4-ylmethoxy]-pyridazine-3-carboxylic acid (50 mg, 0.15 mmol) and TBTU (54 mg, 0.17 mmol) in DMF (2 mL) was added DIPEA (130 µL, 0.76 mmol). Then 2-amino-2-methyl-1-propanol (16 µL, 0.167 mmol) was added and the mixture was stirred at room temperature under Ar for 1 h. The mixture was then evaporated and purification by chromatography (silica, 50 to 100% ethyl acetate in heptane) afforded the title compound (56 mg, 92%) as a white foam. MS: m/e=402.4 [M+H]+.

Example 52

6-[5-(5-Fluoro-pyridin-2-yl)-3-methyl-3H-[1,2,3]triazol-4-ylmethoxy]-pyridazine-3-carboxylic acid morpholin-4-ylamide

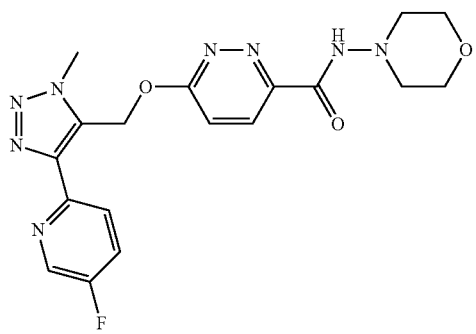 [SMILES: Cn1nnc(-c2ccc(F)cn2)c1COc1ccc(C(=O)NN2CCOCC2)nn1]

As described for example 51c, 6-[5-(5-fluoro-pyridin-2-yl)-3-methyl-3H-[1,2,3]triazol-4-ylmethoxy]-pyridazine-3-carboxylic acid (50 mg, 0.15 mmol) was converted, using N-aminomorpholine instead of 2-amino-2-methyl-1-propanol, to the title compound (35 mg, 56%) which was obtained as a light yellow solid. MS: m/e=415.3 [M+H]+.

Example 53

5-[5-(4-Fluoro-phenyl)-3-methyl-3H-[1,2,3]triazol-4-ylmethoxy]-pyrazine-2-carboxylic acid isopropylamide

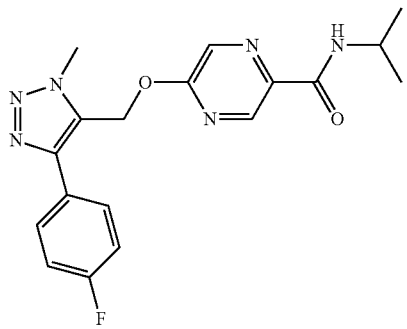 [SMILES: CC(C)NC(=O)c1cnc(OCc2c(-c3ccc(F)cc3)nnn2C)cn1]

a) 5-[5-(4-Fluoro-phenyl)-3-methyl-3H-[1,2,3]triazol-4-ylmethoxy]-pyrazine-2-carboxylic acid methyl ester To a suspension of NaH (55% in oil, 131 mg, 3.0 mmol) in THF (3.9 mL) was added a solution of [5-(4-fluoro-phenyl)-3-methyl-3H-[1,2,3]triazol-4-yl]-methanol (622 mg, 3.0 mmol) in THF (7.9 mL) dropwise at 0° C. and the reaction mixture was stirred at room temperature for 30 min. Then a solution of methyl 5-chloropyrazine-2-carboxylate (569 mg, 3.3 mmol) in THF (7.9 mL) was added dropwise at 0° C. and the reaction mixture was stirred at room temperature for 16 h. The mixture was then poured into ice water and extracted with ethyl acetate and the combined organic extracts washed with brine, dried over sodium sulphate, filtered and evaporated. Purification by chromatography (silica, 0 to 50% ethyl acetate in heptane, then 0 to 5% methanol in dichloromethane) afforded the title compound (474 mg, 46%) as an off white gum. MS: m/e=344.1 [M+H]+.

b) 5-[5-(4-Fluoro-phenyl)-3-methyl-3H-[1,2,3]-triazol-4-ylmethoxy]-pyrazine-2-carboxylic acid A solution of lithium hydroxide monohydrate (107 mg, 2.55 mmol) in water (3.2 mL) was added dropwise to a suspension of 5-[5-(4-fluoro-phenyl)-3-methyl-3H-[1,2,3]triazol-4-ylmethoxy]-pyrazine-2-carboxylic acid methyl ester (438 mg, 1.27 mmol) in THF (1.8 mL). The reaction mixture was then stirred at room temperature for 1 h and was then evaporated and the residue dissolved in water, acidified with HCl (1N), and the resulting precipitate filtered off to afford the title product (403 mg, 96%) as a white solid. MS: m/e=328.1 [M−H]−.

c) 5-[5-(4-Fluoro-phenyl)-3-methyl-3H-[1,2,3]triazol-4-ylmethoxy]-pyrazine-2-carboxylic acid isopropylamide To a solution of 5-[5-(4-fluoro-phenyl)-3-methyl-3H-[1,2,3]triazol-4-ylmethoxy]-pyrazine-2-carboxylic acid (96 mg, 0.29 mmol) and TBTU (103 mg, 0.32 mmol) in DMF (1.5 mL) was added DIPEA (250 µL, 1.46 mmol). Then isopropylamine (27 µL, 0.32 mmol) was added and the mixture was stirred at room temperature under Ar for 1 h. The mixture was then evaporated and purification by chromatography (silica, 50 to 100% ethyl acetate in heptane) afforded the title compound (53 mg, 49%) as a white solid after recrystallisation from ethyl acetate/heptane. MS: m/e=371.3 [M+H]⁺.

Example 54

5-[5-(4-Fluoro-phenyl)-3-methyl-3H-[1,2,3]triazol-4-ylmethoxy]-pyrazine-2-carboxylic acid (tetrahydro-pyran-4-yl)-amide

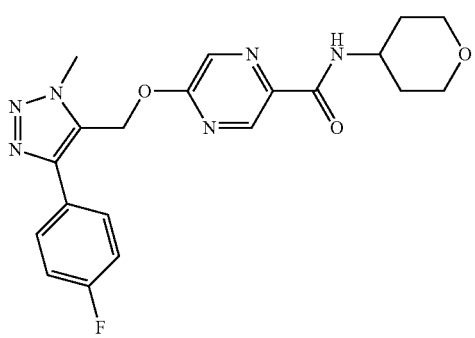 [SMILES: Cn1nnc(-c2ccc(F)cc2)c1COc1cnc(C(=O)NC2CCOCC2)cn1]

As described for example 53c, 5-[5-(4-fluoro-phenyl)-3-methyl-3H-[1,2,3]triazol-4-ylmethoxy]-pyrazine-2-carboxylic acid (96 mg, 0.29 mmol) was converted, using 4-aminotetrahydropyran instead of isopropylamine, to the title compound (74 mg, 62%) which was obtained as an off white solid. MS: m/e=413.4 [M+H]⁺.

Example 55

6-{(E)-2-[5-(4-Fluoro-phenyl)-3-methyl-3H-[1,2,3]triazol-4-yl]-vinyl}-nicotinic acid methyl ester

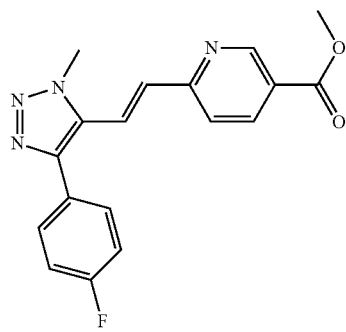 [SMILES: COC(=O)c1ccc(/C=C/c2c(-c3ccc(F)cc3)nnn2C)nc1]

a) 4-(4-Fluoro-phenyl)-1-trimethylsilanylmethyl-1H-[1,2,3]triazole

To a suspension of copper(I)iodide (1.14 g, 20 mol %) in DMF (300 mL) was added DIPEA (5.14 mL, 6.0 mmol) and 4-fluorophenylacetylene (3.60 g 30 mmol) at room temperature and then trimethyl(triazomethyl)silane (3.88 g, 30.0 mmol) was added. The resulting reaction mixture was stirred at room temperature for 18 h. The mixture was poured into water:brine (1:1) and then extracted with ethyl acetate. The combined organic extracts were then washed with brine, dried over sodium sulphate, filtered and evaporated. Purification by chromatography (silica, 0 to 100% ethyl acetate in heptane) afforded the title compound (5.96 g, 80%) as an off white solid. MS: m/e=250.1 [M+H]⁺.

b) 4-(4-Fluoro-phenyl)-1-methyl-1H-[1,2,3]triazole

To a solution of 4-(4-fluoro-phenyl)-1-trimethylsilanylmethyl-1H-[1,2,3]triazole (5.80 g, 23 mmol) in THF (85 mL) was added water (840 µL, 47 mmol) and then tetrabutylammonium fluoride (1 M in THF, 27.9 mL, 28 mmol) was added dropwise at 0° C. The reaction mixture was stirred at 0° C. for 1 h. The resulting mixture was poured into water and then the THF was evaporated. The aqueous layer was then extracted with ethyl acetate and the combined organic extracts washed with brine, dried over sodium sulphate, filtered and evaporated. Purification by chromatography (silica, 50 to 100% ethyl acetate in heptane) afforded the title compound (4.0 g, 98%) as an off white solid. MS: m/e=178.1 [M+H]⁺.

c) 5-(4-Fluoro-phenyl)-3-methyl-3H-[1,2,3]-triazole-4-carbaldehyde

To a solution of 4-(4-fluoro-phenyl)-1-methyl-1H-[1,2,3]triazole (709 mg, 4.0 mmol) in THF (20 mL) was added n-BuLi (1.6 M in hexane, 3.0 mL, 4.8 mmol) dropwise at −75° C. under Argon. The resulting solution was stirred at −75° C. for 1 h, then DMF (401 µL, 5.2 mmol) was added dropwise at −75° C. and the reaction mixture was allowed to warm up to room temperature over 1 h. The mixture was then poured into saturated ammonium chloride solution and extracted with ethyl acetate and the combined organic extracts washed with brine, dried over sodium sulphate, filtered and evaporated. Purification by chromatography (silica, 0 to 100% ethyl acetate in heptane) afforded the title compound (773 mg, 94%) as a white solid. MS: m/e=206.2 [M]⁺.

d) 6-{(E)-2-[5-(4-Fluoro-phenyl)-3-methyl-3H-[1,2,3]triazol-4-yl]-vinyl}-nicotinic acid methyl ester To a solution of 5-(4-fluoro-phenyl)-3-methyl-3H-[1,2,3]triazole-4-carbaldehyde (308 mg, 1.5 mmol) in acetic anhydride (0.8 mL) and AcOH (141 µL) was added methyl-6-methylnicotinate (227 mg, 1.5 mmol) and the reaction mixture was heated at 120° C. for 144 h. The mixture was then poured into water, sodium hydroxide (2 N) added and extracted with ethyl acetate and the combined organic extracts washed with brine, dried over sodium sulphate, filtered and evaporated. Purification by chromatography (silica, 0 to 10% methanol in dichloromethane) afforded the title compound (154 mg, 30%) as a light brown solid. MS: m/e=339.1 [M+H]⁺.

Example 56

6-{(E)-2-[5-(4-Fluoro-phenyl)-3-methyl-3H-[1,2,3]triazol-4-yl]-vinyl}-N-isopropyl-nicotinamide

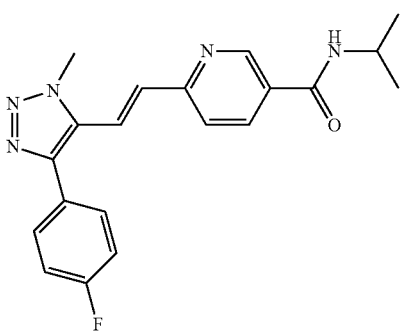 [SMILES: CC(C)NC(=O)c1ccc(/C=C/c2c(-c3ccc(F)cc3)nnn2C)nc1]

a) 6-{(E)-2-[5-(4-Fluoro-phenyl)-3-methyl-3H-[1,2,3]triazol-4-yl]-vinyl}-nicotinic acid A solution of lithium hydroxide monohydrate (34 mg, 0.8 mmol) in water (1.0 mL) was added dropwise to a suspension of 6-{(E)-2-[5-(4-fluoro-phenyl)-3-methyl-3H-[1,2,3]triazol-4-yl]-vinyl}-nicotinic acid methyl ester (136 mg, 0.4 mmol) in THF (1.0 mL) and methanol (0.2 mL). The reaction mixture was then stirred at room temperature for 1 h and was then evaporated and the residue dissolved in water, acidified with HCl (1N), and the resulting precipitate filtered off to afford the title product (114 mg, 87%) as a white solid. MS: m/e=323.2 [M−H]⁻.

b) 6-{(E)-2-[5-(4-Fluoro-phenyl)-3-methyl-3H-[1,2,3]-triazol-4-yl]-vinyl}-N-isopropyl-nicotinamide To a solution of 6-{(E)-2-[5-(4-fluoro-phenyl)-3-methyl-3H-[1,2,3]triazol-4-yl]-vinyl}-nicotinic acid (49 mg, 0.15 mmol) and TBTU (53 mg, 0.17 mmol) in DMF (0.8 mL) was added DIPEA (129 µL, 0.76 mmol). Then isopropylamine (14 µL, 0.17 mmol) was added and the mixture was stirred at room temperature under Ar for 1 h. The mixture was then evaporated and purification by chromatography (silica, 0 to 10% methanol in dichloromethane) afforded the title compound (45 mg, 82%) as a light yellow solid after recrystallisation from methanol/water. MS: m/e=366.1 [M+H]⁺.

Example 57

6-{(E)-2-[5-(4-Fluoro-phenyl)-3-methyl-3H-[1,2,3]triazol-4-yl]-vinyl}-N-(tetrahydro-pyran-4-yl)-nicotinamide

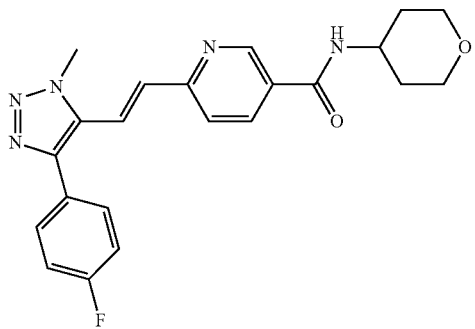 [SMILES: Cn1nnc(-c2ccc(F)cc2)c1/C=C/c1ccc(C(=O)NC2CCOCC2)cn1]

As described for example 56b, 6-{(E)-2-[5-(4-fluoro-phenyl)-3-methyl-3H-[1,2,3]triazol-4-yl]-vinyl}-nicotinic acid (49 mg, 0.15 mmol) was converted, using 4-aminotetrahydropyran instead of isopropylamine, to the title compound (45 mg, 82%) which was obtained as a light yellow solid. MS: m/e=366.1 [M+H]⁺.

Example 58

6-[5-(4-Fluoro-phenyl)-3-methyl-3H-[1,2,3]triazol-4-ylethynyl]-N-isopropyl-nicotinamide

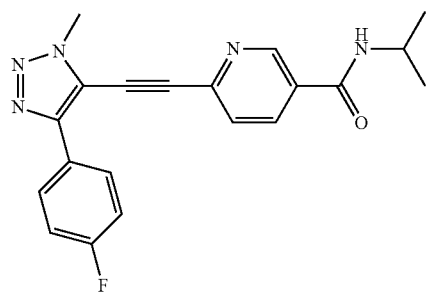 [SMILES: CC(C)NC(=O)c1ccc(C#Cc2c(-c3ccc(F)cc3)nnn2C)nc1]

a) 5-Ethynyl-4-(4-fluoro-phenyl)-1-methyl-1H-[1,2,3]triazole

To a mixture of 5-(4-fluoro-phenyl)-3-methyl-3H-[1,2,3]triazole-4-carbaldehyde (616 mg, 3.0 mmol) in MeOH (13 mL) was added potassium carbonate (829 mg, 6.0 mmol) followed by a solution of (1-diazo-2-oxo-propyl)-phosphonic acid dimethyl ester (634 mg, 3.3 mmol) in MeOH (4 mL) at room temperature and the resulting mixture stirred for 1 h. The mixture was then poured into sodium carbonate solution (1 M) and extracted with ethyl acetate and the combined organic extracts washed with brine, dried over sodium sulphate, filtered and evaporated. Purification by chromatography (silica, 0 to 50% ethyl acetate in heptane) afforded the title compound (556 mg, 92%) as a light red solid. MS: m/e=202.2 [M]⁺.

b) 6-[5-(4-Fluoro-phenyl)-3-methyl-3H-[1,2,3]triazol-4-ylethynyl]-nicotinic acid methyl ester A mixture of 5-ethynyl-4-(4-fluoro-phenyl)-1-methyl-1H-[1,2,3]triazole (101 mg, 0.5 mmol), methyl 6-bromonicotinate (130 mg, 0.6 mmol), triethylamine (174 µL, 1.25 mmol) and PdCl₂(PPh₃)₂ (11 mg, 0.3 mol %) in DMF (1 mL) was evaporated and flushed with Ar five times. Then CuI (2 mg, 0.2 mol %) was added and the reaction mixture was stirred at 90° C. for 30 min and DMF (1 mL) was added. The mixture was then poured into sodium hydroxide solution (1 M) and extracted with ethyl acetate and the combined organic extracts washed with brine, dried over sodium sulphate, filtered and evaporated. Purification by chromatography (silica, 0 to 50% ethyl acetate in heptane) afforded the title compound (133 mg, 79%) as a light yellow solid. MS: m/e=337.1 [M]⁺.

c) 6-[5-(4-Fluoro-phenyl)-3-methyl-3H-[1,2,3]triazol-4-ylethynyl]-nicotinic acid A solution of lithium hydroxide monohydrate (30 mg, 0.72 mmol) in water (0.9 mL) was added dropwise to a suspension of 6-[5-(4-fluoro-phenyl)-3-methyl-3H-[1,2,3]triazol-4-ylethynyl]-nicotinic acid methyl ester (121 mg, 0.36 mmol) in THF (0.9 mL) and methanol (0.2 mL). The reaction mixture was then stirred at room temperature for 18 h and was then evaporated and the residue dissolved in water, acidified with HCl (1N), and the resulting precipitate filtered off to afford the title product (89 mg, 77%) as a light yellow solid after trituration with ethyl acetate. MS: m/e=321.1 [M–H]⁻.

d) 6-[5-(4-Fluoro-phenyl)-3-methyl-3H-[1,2,3]triazol-4-ylethynyl]-N-isopropyl-nicotinamide To a solution of 6-[5-(4-fluoro-phenyl)-3-methyl-3H-[1,2,3]triazol-4-ylethynyl]-nicotinic acid (69 mg, 0.21 mmol) and TBTU (76 mg, 0.24 mmol) in DMF (1.0 mL) was added DIPEA (183 μL, 1.07 mmol). Then isopropylamine (20 μL, 0.24 mmol) was added and the mixture was stirred at room temperature under Ar for 1 h. The mixture was then evaporated and purification by chromatography (silica, 50 to 100% ethyl acetate in heptane) afforded the title compound (39 mg, 50%) as a light yellow solid after recrystallisation from ethyl acetate/heptane. MS: m/e=364.2 [M+H]⁺.

Example 59

6-[5-(4-Fluoro-phenyl)-3-methyl-3H-[1,2,3]triazol-4-ylethynyl]-N-(tetrahydro-pyran-4-yl)-nicotinamide

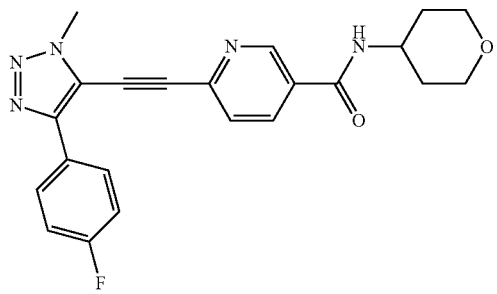 [SMILES: Cn1nnc(-c2ccc(F)cc2)c1C#Cc1ccc(C(=O)NC2CCOCC2)cn1]

As described for example 58d, 6-[5-(4-fluoro-phenyl)-3-methyl-3H-[1,2,3]triazol-4-ylethynyl]-nicotinic acid (69 mg, 0.21 mmol) was converted, using 4-aminotetrahydropyran instead of isopropylamine, to the title compound (64 mg, 74%) which was obtained as a light yellow solid. MS: m/e=406.2 [M+H]⁺.

Example 60

6-[3-(4-Fluoro-phenyl)-5-methyl-3H-[1,2,3]triazol-4-ylmethoxy]-nicotinic acid methyl ester

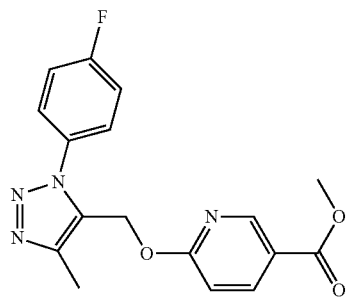 [SMILES: COC(=O)c1ccc(OCc2c(C)nnn2-c2ccc(F)cc2)nc1]

a) 1-Azido-4-fluoro-benzene

Prepared in analogy to J. Org. Chem. (1989) 54:5938-5945. To a solution of sulfuric acid (40 mL) and trifluoroacetic acid (200 mL) was added 4-fluoroaniline (22.1 mL, 0.23 mol) dropwise. Then under ice-cooling a solution of sodium nitrite (20.6 g, 0.3 mol) in water (200 mL) was added over 30 min at 15-18° C. The solution was then stirred for 30 min while kept in the ice bath. A solution of sodium azide (25.42 g, 0.39 mol) in water (150 mL) was added dropwise over 30 min. Mixture was foaming and temperature went up to 10° C. while cooling with an ice bath. Reaction mixture was stirred without cooling for 1 h, then extracted with diethyl ether. The combined organic layers were washed with water two times. Then the combined organic layers were diluted with saturated aqueous sodium carbonate solution (500 mL) until the mixture became basic. The organic phase was separated and washed with brine, extracted again with diethyl ether. The organic layers were dried over sodium sulfate and evaporated at 40° C., minimum 50 mbar (already distillation of product), to afford the title product (30.42 g, 96%) as a brown liquid.

b) 1-[3-(4-Fluoro-phenyl)-5-methyl-4,5-dihydro-3H-[1,2,3]triazol-4-yl]-piperidine Prepared in analogy to EP 0 433 842 A2. A mixture of 1-azido-4-fluoro-benzene (2.80 g, 20 mmol) and 1-(1-propenyl)-piperidine (18%, 14.2 g, 20 mmol) was stirred under ice cooling (slowly exothermic in the beginning) and at room temperature for 144 h in the absence of light. Hexane was then added to the brown solutions and a solid formed which was filtered off, washed with hexane and dried in hv to give the title product (1.1 g) as a light pink solid. The filtrate was then evaporated and purification by chromatography (silica, 10 to 50% ethyl acetate in heptane) afforded the title compound (4.34 g) as a light yellow solid. Total yield (5.44 g, 98%). MS: m/e=263.1 [M+H]⁺.

c) 1-(4-Fluoro-phenyl)-4-methyl-1H-[1,2,3]-triazole

Prepared in analogy to EP 0 433 842 A2. A mixture of 1-[3-(4-fluoro-phenyl)-5-methyl-4,5-dihydro-3H-[1,2,3] triazol-4-yl]-piperidine (1.15 g, 0.004 mol) and potassium hydroxide in MeOH (2 N, 29.2 mL, 58 mmol) was heated under reflux for 6 h then cooled to room temperature. The mixture was then poured into water and extracted with diethyl ether and the combined organic extracts washed with brine, dried over sodium sulphate, filtered and evaporated to give the title product (555 mg) as a white solid. The filtrate was evaporated and purification by chromatography (silica, 10 to 60% ethyl acetate in heptane) afforded the title compound (41 mg, 79%) as an off white solid. Total yield (596 mg, 77%). MS: m/e=178.1 [M+H]⁺.

d) 3-(4-Fluoro-phenyl)-5-methyl-3H-[1,2,3]triazole-4-carbaldehyde

To a solution of 1-(4-fluoro-phenyl)-4-methyl-1H-[1,2,3] triazole (3.67 g, 21 mmol) in THF (110 mL) was added n-BuLi (1.6 M in hexane, 15.53 mL, 25 mmol) dropwise at −75° C. under Argon. The resulting solution was stirred at −75° C. for 1 h, then DMF (2.1 mL, 27 mmol) was added dropwise at −75° C. and the reaction mixture was allowed to warm up to room temperature over 1 h. The mixture was then poured into saturated ammonium chloride solution and extracted with ethyl acetate and the combined organic extracts washed with brine, dried over sodium sulphate, file) [3-(4-Fluoro-phenyl)-5-methyl-3H-[1,2,3]-triazol-4-yl]-methanol To a solution of 3-(4-fluoro-phenyl)-5-methyl-3H-[1,2,3] triazole-4-carbaldehyde (2.28 g, 11 mmol) in MeOH (180 mL) was added sodiumborohydride (210 mg, 6.0 mmol) at 0° C., and the resulting mixture stirred at 0° C. for 30 min, The mixture was then poured into saturated ammonium chloride solution and extracted with ethyl acetate and the combined organic extracts washed with brine, dried over sodium sulphate, filtered and evaporated to afford the title compound (2.05 g, 89%) as a white solid. MS: m/e=208.2 [M]$^+$.

f) 6-[3-(4-Fluoro-phenyl)-5-methyl-3H-[1,2,3]-triazol-4-ylmethoxy]-nicotinic acid methyl ester A solution of [3-(4-fluoro-phenyl)-5-methyl-3H-[1,2,3] triazol-4-yl]-methanol (425 mg, 2.05 mmol) in THF (3 mL) was added dropwise at 0° C. to a suspension of NaH (55% in oil, 100 mg, 2.05 mmol) in THF (6 mL) and the reaction mixture was then stirred at room temperature for 30 min. Then a solution of methyl 6-chloronicotinate (390 mg, 8.0 mmol) in THF (3 mL) was added dropwise at 0° C. and the reaction mixture stirred at room temperature for 20 h. The mixture was then poured into water extracted with ethyl acetate and the combined organic extracts washed with brine, dried over sodium sulphate, filtered and evaporated. Purification by chromatography (silica, 10 to 50% ethyl acetate in heptane) afforded the title compound (621 mg, 88%) as a white solid. MS: m/e=343.3 [M+H]$^+$.

Example 61

6-[3-(4-Fluoro-phenyl)-5-methyl-3H-[1,2,3]triazol-4-ylmethoxy]-N-(tetrahydro-pyran-4-yl)-nicotinamide

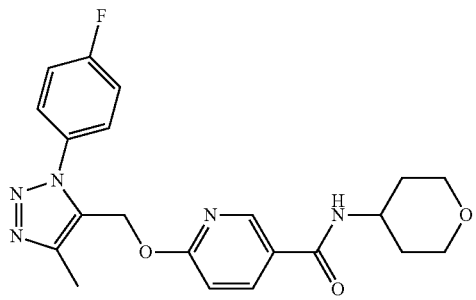

a) 6-[3-(4-Fluoro-phenyl)-5-methyl-3H-[1,2,3]triazol-4-ylmethoxy]-nicotinic acid A solution of lithium hydroxide monohydrate (143 mg, 3.39 mmol) in water (5.8 mL) was added dropwise to a suspension of 6-[3-(4-fluoro-phenyl)-5-methyl-3H-[1,2,3] triazol-4-ylmethoxy]-nicotinic acid methyl ester (581 mg, 1.7 mmol) in THF (5.8 mL) and methanol (2 mL). The reaction mixture was then stirred at room temperature for 30 min and was then evaporated and the residue dissolved in water, acidified with HCl (1N), and the resulting precipitate filtered off to afford the title product (538 mg, 97%) as a white solid. MS: m/e=327.2 [M−H]$^-$.

b) 6-[3-(4-Fluoro-phenyl)-5-methyl-3H-[1,2,3]-triazol-4-ylmethoxy]-N-(tetrahydro-pyran-4-yl)-nicotinamide To a solution of 6-[3-(4-fluoro-phenyl)-5-methyl-3H-[1,2,3]triazol-4-ylmethoxy]-nicotinic acid (83 mg, 0.25 mmol) and TBTU (90 mg, 0.28 mmol) in DMF (3.0 mL) was added DIPEA (217 µL, 1.26 mmol). Then 4-aminotetrahydropyran (28 mg, 0.28 mmol) was added and the mixture was stirred at room temperature under Ar for 30 min. The mixture was then evaporated and purification by chromatography (silica, 50 to 100% ethyl acetate in heptane) afforded the title compound (100 mg, 96%) as a white solid. MS: m/e=412.3 [M+H]$^+$.

Example 62

6-[3-(4-Fluoro-phenyl)-5-methyl-3H-[1,2,3]triazol-4-ylmethoxy]-N-isopropyl-nicotinamide

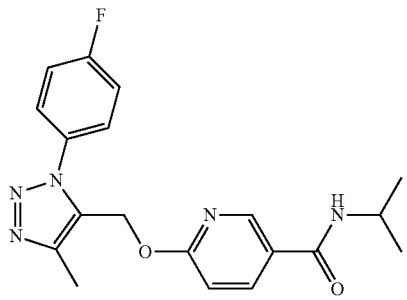

As described for example 61b, 6-[3-(4-fluoro-phenyl)-5-methyl-3H-[1,2,3]triazol-4-ylmethoxy]-nicotinic acid (83 mg, 0.25 mmol) was converted, using isopropylamine instead of 4-aminotetrahydropyran, to the title compound (85 mg, 91%) which was obtained as a white solid. MS: m/e=370.2 [M+H]$^+$.

Example 63

6-[3-(4-Fluoro-phenyl)-5-methyl-3H-[1,2,3]triazol-4-ylmethoxy]-N-(2-hydroxy-1,1-dimethyl-ethyl)-nicotinamide

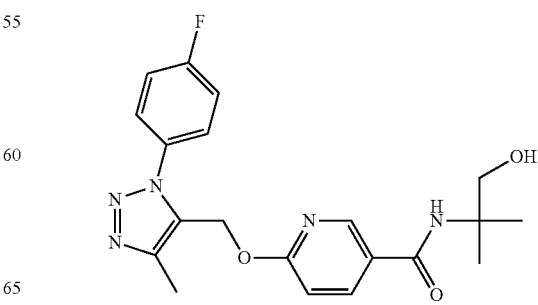

As described for example 61b, 6-[3-(4-fluoro-phenyl)-5-methyl-3H-[1,2,3]triazol-4-ylmethoxy]-nicotinic acid (83 mg, 0.25 mmol) was converted, using 2-amino-2-methyl-1-propanol instead of 4-aminotetrahydropyran, to the title compound (95 mg, 94%) which was obtained as a white foam. MS: m/e=400.2 [M+H]$^+$.

Example 64

6-[3-(4-Fluoro-phenyl)-5-methyl-3H-[1,2,3]triazol-4-ylmethoxy]-N-morpholin-4-yl-nicotinamide

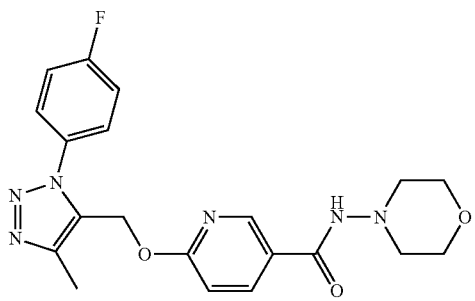 [SMILES: Cc1nnn(-c2ccc(F)cc2)c1COc1ccc(C(=O)NN2CCOCC2)cn1]

As described for example 61b, 6-[3-(4-fluoro-phenyl)-5-methyl-3H-[1,2,3]triazol-4-ylmethoxy]-nicotinic acid (83 mg, 0.25 mmol) was converted, using 4-aminomorpholine instead of 4-aminotetrahydropyran, to the title compound (81 mg, 78%) which was obtained as a white solid. MS: m/e=413.3 [M+H]$^+$.

Example 65

6-[3-(4-Fluoro-phenyl)-5-methyl-3H-[1,2,3]triazol-4-ylmethoxy]-N-(3-methyl-oxetan-3-yl)-nicotinamide

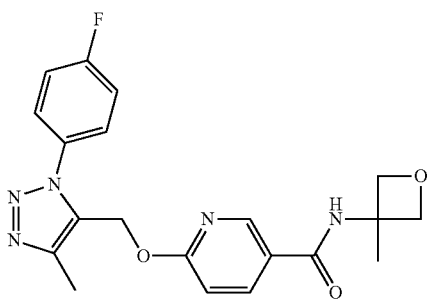 [SMILES: Cc1nnn(-c2ccc(F)cc2)c1COc1ccc(C(=O)NC2(C)COC2)cn1]

As described for example 61b, 6-[3-(4-fluoro-phenyl)-5-methyl-3H-[1,2,3]triazol-4-ylmethoxy]-nicotinic acid (83 mg, 0.25 mmol) was converted, using 3-methyl-3-oxetan-amine instead of 4-aminotetrahydropyran, to the title compound (91 mg, 91%) which was obtained as a white solid. MS: m/e=398.2 [M+H]$^+$.

Example 66

Methyl 6-((1-(2-fluorophenyl)-4-methyl-1H-1,2,3-triazol-5-yl)methoxy)nicotinate

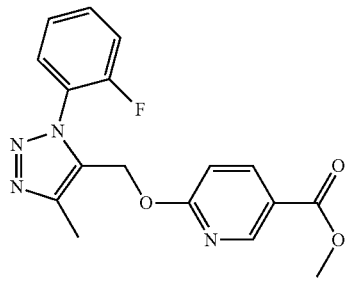 [SMILES: COC(=O)c1ccc(OCc2c(C)nnn2-c2ccccc2F)nc1]

a) 1-Azido-2-fluorobenzene

As described for example 60a, 2-fluoroaniline (5.0 g, 45 mmol), instead of 4-fluoroaniline, was converted to the title compound (6.28 g, 99%) which was obtained as a brown liquid.

b) 1-(1-(2-Fluorophenyl)-4-methyl-4,5-dihydro-1H-1,2,3-triazol-5-yl)piperidine

As described for example 60b, 1-azido-2-fluorobenzene (2.8 g, 20 mmol), instead of 1-azido-4-fluoro-benzene, was converted to the title compound (4.87 g, 93%) which was obtained as a brown solid. MS: m/e=263.2 [M+H]$^+$.

c) 1-(2-Fluorophenyl)-4-methyl-1H-1,2,3-triazole

As described for example 60c, 1-(1-(2-fluorophenyl)-4-methyl-4,5-dihydro-1H-1,2,3-triazol-5-yl)piperidine (1.32 g, 5.32 mmol), instead of 1-[3-(4-fluoro-phenyl)-5-methyl-4,5-dihydro-3H-[1,2,3]triazol-4-yl]-piperidine, was converted to the title compound (616 mg, 65%) which was obtained as a colourless liquid. MS: m/e=178.1 [M+H]$^+$.

d) 1-(2-Fluorophenyl)-4-methyl-1H-1,2,3-triazole-5-carbaldehyde

As described for example 60d, 1-(2-fluorophenyl)-4-methyl-1H-1,2,3-triazole (1.63 g, 9.2 mmol), instead of 1-(4-fluoro-phenyl)-4-methyl-1-[1,2,3]triazole, was converted to the title compound (1.45 g, 77%) which was obtained as a light yellow oil. MS: m/e=206.1 [M+H]$^+$.

e) (1-(2-Fluorophenyl)-4-methyl-1H-1,2,3-triazol-5-yl)methanol

As described for example 60e, 1-(2-fluorophenyl)-4-methyl-1H-1,2,3-triazole-5-carbaldehyde (469 mg, 2.19 mmol), instead of 3-(4-fluoro-phenyl)-5-methyl-3H-[1,2,3]triazole-4-carbaldehyde, was converted to the title compound (339 mg, 75%) which was obtained as a white solid. MS: m/e=208.1 [M+H]$^+$.

f) Methyl 6-((1-(2-fluorophenyl)-4-methyl-1H-1,2,3-triazol-5-yl)methoxy)nicotinate As described for example 60f, (1-(2-fluorophenyl)-4-methyl-1H-1,2,3-triazol-5-yl)methanol (317 mg, 1.53 mmol), instead of [3-(4-fluoro-phenyl)-5-methyl-3H-[1,2,3]triazol-4-yl]-methanol, was converted to the title compound (195 mg, 37%) which was obtained as a colourless gum. MS: m/e=343.1 [M+H]$^+$.

Example 67

6-((1-(2-Fluorophenyl)-4-methyl-1H-1,2,3-triazol-5-yl)methoxy)-N-isopropylnicotinamide

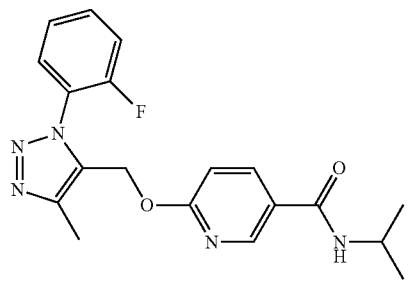 [SMILES: Cc1nnn(-c2ccccc2F)c1COc1ccc(C(=O)NC(C)C)cn1]

a) 6-((1-(2-Fluorophenyl)-4-methyl-1H-1,2,3-triazol-5-yl)methoxy)nicotinic acid As described for example 61a, methyl 6-((1-(2-fluorophenyl)-4-methyl-1H-1,2,3-triazol-5-yl)methoxy)nicotinate (160 mg, 0.47 mmol), instead of 6-[3-(4-fluoro-phenyl)-5-methyl-3H-[1,2,3]triazol-4-ylmethoxy]-nicotinic acid methyl ester, was converted to the title compound (132 mg, 86%) which was obtained as a white solid. MS: m/e=327.2 [M−H]$^-$.

b) 6-((1-(2-Fluorophenyl)-4-methyl-1H-1,2,3-triazol-5-yl)methoxy)-N-isopropylnicotinamide As described for example 62, 6-((1-(2-fluorophenyl)-4-methyl-1H-1,2,3-triazol-5-yl)methoxy)nicotinic acid (55 mg, 0.17 mmol), instead of 6-[3-(4-fluoro-phenyl)-5-methyl-3H-[1,2,3]triazol-4-ylmethoxy]-nicotinic acid, was converted to the title compound (48 mg, 78%) which was obtained as a white foam. MS: m/e=370.1 [M+H]$^+$.

Example 68

6-((1-(2-Fluorophenyl)-4-methyl-1H-1,2,3-triazol-5-yl)methoxy)-N-(tetrahydro-2H-pyran-4-yl)nicotinamide

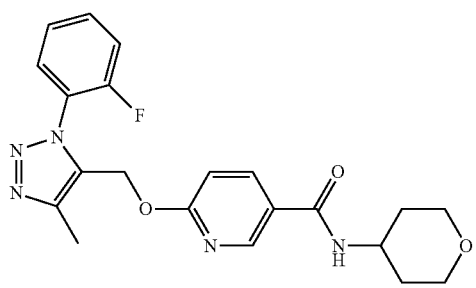 [SMILES: Cc1nnn(-c2ccccc2F)c1COc1ccc(C(=O)NC2CCOCC2)cn1]

As described for example 67, 6-((1-(2-fluorophenyl)-4-methyl-1H-1,2,3-triazol-5-yl)methoxy)nicotinic acid (55 mg, 0.17 mmol), was converted, using 4-aminotetrahydropyran instead of isopropylamine, to the title compound (42 mg, 61%) which was obtained as a white foam. MS: m/e=412.2 [M+H]$^+$.

Example 69

6-((1-(2-Fluorophenyl)-4-methyl-1H-1,2,3-triazol-5-yl)methoxy)-N-(3-methyloxetan-3-yl)nicotinamide

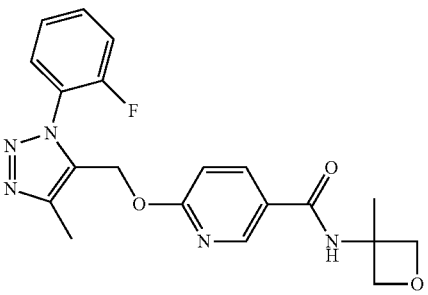 [SMILES: Cc1nnn(-c2ccccc2F)c1COc1ccc(C(=O)NC2(C)COC2)cn1]

As described for example 67, 6-((1-(2-fluorophenyl)-4-methyl-1H-1,2,3-triazol-5-yl)methoxy)nicotinic acid (78 mg, 0.24 mmol), was converted, using 3-methyloxetan-3-amine instead of isopropylamine, to the title compound (20 mg, 21%) which was obtained as an off white foam. MS: m/e=398.2 [M+H]$^+$.

Example 70

6-((1-(2-Fluorophenyl)-4-methyl-1H-1,2,3-triazol-5-yl)methoxy)-N-morpholinonicotinamide

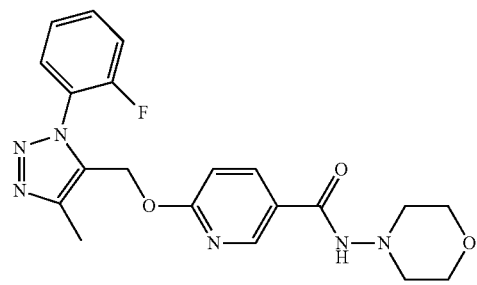

As described for example 67, 6-((1-(2-fluorophenyl)-4-methyl-1H-1,2,3-triazol-5-yl)methoxy)nicotinic acid (78 mg, 0.24 mmol), was converted, using 4-aminomorpholine instead of isopropylamine, to the title compound (65 mg, 66%) which was obtained as an off white foam. MS: m/e=413.4 [M+H]$^+$.

Example 71

N-Cyclopropyl-6-((1-(2-fluorophenyl)-4-methyl-1H-1,2,3-triazol-5-yl)methoxy)nicotinamide

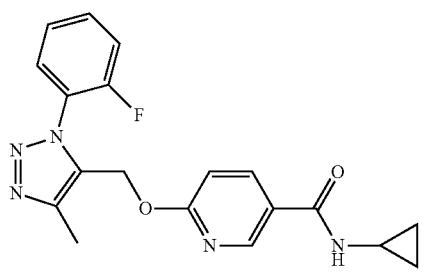 [SMILES: Cc1nnn(-c2ccccc2F)c1COc1ccc(C(=O)NC2CC2)cn1]

As described for example 67, 6-((1-(2-fluorophenyl)-4-methyl-1H-1,2,3-triazol-5-yl)methoxy)nicotinic acid (78 mg, 0.24 mmol), was converted, using cyclopropylamine instead of isopropylamine, to the title compound (72 mg, 83%) which was obtained as a white foam. MS: m/e=368.2 [M+H]$^+$.

Example 72

N-(Cyclopropylmethyl)-6-((1-(2-fluorophenyl)-4-methyl-1H-1,2,3-triazol-5-yl)methoxy)nicotinamide

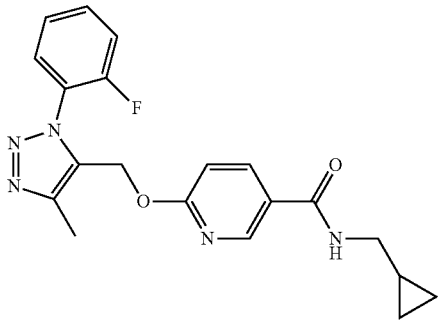 [SMILES: Cc1nnn(-c2ccccc2F)c1COc1ccc(C(=O)NCC2CC2)cn1]

As described for example 67, 6-((1-(2-fluorophenyl)-4-methyl-1H-1,2,3-triazol-5-yl)methoxy)nicotinic acid (78 mg, 0.24 mmol), was converted, using cyclopropylmethylamine instead of isopropylamine, to the title compound (54 mg, 60%) which was obtained as a white gum. MS: m/e=382.3 [M+H]$^+$.

Example 73

3-Chloro-6-[3-(4-fluoro-phenyl)-5-methyl-3H-[1,2,3]triazol-4-ylmethoxy]-pyridazine

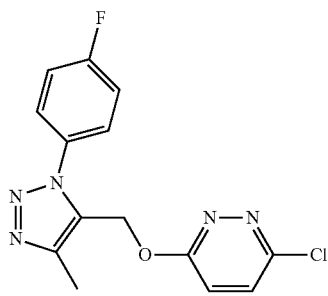 [SMILES: Cc1nnn(-c2ccc(F)cc2)c1COc1ccc(Cl)nn1]

To a suspension of sodium hydride (55%, 106 mg, 2.41 mmol) in THF (4 mL) a solution of [3-(4-fluoro-phenyl)-5-methyl-3H-[1,2,3]triazol-4-yl]-methanol (500 mg, 2.41 mmol) in THF (6 mL) was added under ice cooling. After the addition was complete the mixture was allowed to warm up to room temperature and stirred for 30 min. Again under ice cooling a solution of 3,6-dichloropyridazine (358 mg, 2.41 mmol) in THF (6 mL) was added and the reaction mixture stirred at room temperature for 16 h. The mixture was then poured into ice water and extracted with ethyl acetate and the combined organic extracts washed with brine, dried over sodium sulphate, filtered and evaporated. Purification by chromatography (silica, 0 to 50% ethyl acetate in heptane) afforded the title compound (735 mg, 95%) as a colourless gum. MS: m/e=3020.1 [M+H]$^+$.

Example 74

6-[3-(4-Fluoro-phenyl)-5-methyl-3H-[1,2,3]triazol-4-ylmethoxy]-pyridazine-3-carboxylic acid ethyl ester

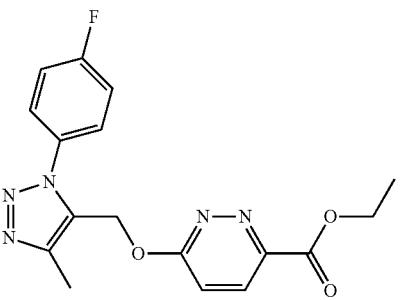 [SMILES: CCOC(=O)c1ccc(OCc2c(C)nnn2-c2ccc(F)cc2)nn1]

To a suspension of 3-chloro-6-[3-(4-fluoro-phenyl)-5-methyl-3H-[1,2,3]triazol-4-ylmethoxy]-pyridazine (696 mg, 2.18 mmol) in ethanol (11 mL) was added sodium carbonate (231 mg, 2.18 mmol) followed by 1,1'-bis(diphenylphosphino) ferrocene (121 mg, 0.22 mmol) and palladium(II) acetate (49 mg, 0.22 mmol). The reaction flask was filled with Ar three times after a short evacuation. The fourth time the flask was flushed with CO-gas (balloon). The mixture was stirred under CO atmosphere at 50° C. over night, then cooled to room temperature and filtered over dicalite and washed well with DCM. The filtrate was then evaporated. Purification by chromatography (silica, 0 to 50% ethyl acetate in heptane) afforded the title compound (725 mg, 93%) as a light yellow gum. MS: m/e=358.2 [M+H]$^+$.

Example 75

6-[3-(4-Fluoro-phenyl)-5-methyl-3H-[1,2,3]triazol-4-ylmethoxy]-pyridazine-3-carboxylic acid isopropylamide

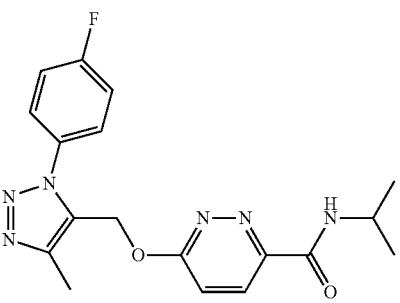 [SMILES: Cc1nnn(-c2ccc(F)cc2)c1COc1ccc(C(=O)NC(C)C)nn1]

a) 6-[3-(4-Fluoro-phenyl)-5-methyl-3H-[1,2,3]-triazol-4-ylmethoxy]-pyridazine-3-carboxylic acid A solution of lithium hydroxide monohydrate (163 mg, 3.88 mmol) in water (7 mL) was added dropwise to a suspension of 6-[3-(4-fluoro-phenyl)-5-methyl-3H-[1,2,3]triazol-4-ylmethoxy]-pyridazine-3-carboxylic acid ethyl ester (694 mg, 1.94 mmol) in THF (7 mL). The reaction mixture was then stirred at room temperature for 30 min and was then evaporated and the residue dissolved in water, acidified with HCl (1N), and the resulting precipitate filtered off to afford the title product (635 mg, 99%) as a white solid. MS: m/e=328.3 [M−H]$^−$.

b) 6-[3-(4-Fluoro-phenyl)-5-methyl-3H-[1,2,3]-triazol-4-ylmethoxy]-pyridazine-3-carboxylic acid isopropylamide To a solution of 6-[3-(4-fluoro-phenyl)-5-methyl-3H-[1,2,3]triazol-4-ylmethoxy]-pyridazine-3-carboxylic acid (85 mg, 0.26 mmol) and TBTU (92 mg, 0.28 mmol) in DMF (3.0 mL) was added DIPEA (221 μL, 1.29 mmol). Then isopropylamine (25 μL, 0.28 mmol) was added and the mixture was stirred at room temperature under Ar for 30 min. The mixture was then evaporated and purification by chromatography (silica, 50 to 100% ethyl acetate in heptane) afforded the title compound (84 mg, 88%) as a light yellow solid. MS: m/e=371.1 [M+H]$^+$.

Example 76

6-[3-(4-Fluoro-phenyl)-5-methyl-3H-[1,2,3]triazol-4-ylmethoxy]-pyridazine-3-carboxylic acid morpholin-4-ylamide

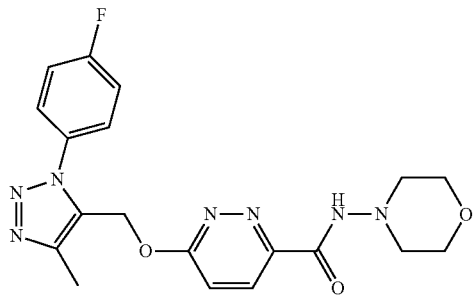

As described for example 75b, 6-[3-(4-fluoro-phenyl)-5-methyl-3H-[1,2,3]triazol-4-ylmethoxy]-pyridazine-3-carboxylic acid (85 mg, 0.26 mmol), was converted, using 4-aminomorpholine instead of isopropylamine, to the title compound (76 mg, 71%) which was obtained as a white solid. MS: m/e=414.3 [M+H]$^+$.

Example 77

6-[3-(4-Fluoro-phenyl)-5-methyl-3H-[1,2,3]triazol-4-ylmethoxy]-pyridazine-3-carboxylic acid (3-methyl-oxetan-3-yl)-amide

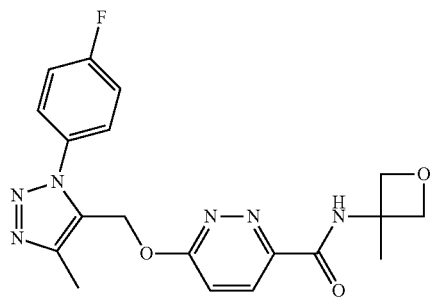 [SMILES: Cc1nnn(-c2ccc(F)cc2)c1COc1ccc(C(=O)NC2(C)COC2)nn1]

As described for example 75b, 6-[3-(4-fluoro-phenyl)-5-methyl-3H-[1,2,3]triazol-4-ylmethoxy]-pyridazine-3-carboxylic acid (85 mg, 0.26 mmol), was converted, using 3-methyl-3-oxetanamine instead of isopropylamine, to the title compound (96 mg, 94%) which was obtained as a light yellow solid. MS: m/e=399.2 [M+H]$^+$.

Example 78

6-[3-(4-Fluoro-phenyl)-5-methyl-3H-[1,2,3]triazol-4-ylmethoxy]-pyridazine-3-carboxylic acid (tetrahydro-pyran-4-yl)-amide

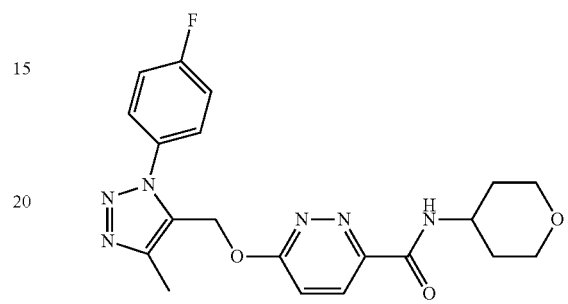

As described for example 75b, 6-[3-(4-fluoro-phenyl)-5-methyl-3H-[1,2,3]triazol-4-ylmethoxy]-pyridazine-3-carboxylic acid (85 mg, 0.26 mmol), was converted, using 4-aminotetrahydropyran instead of isopropylamine, to the title compound (86 mg, 81%) which was obtained as a white solid. MS: m/e=413.3 [M+H]$^+$.

Example 79

6-((1-(4-Fluorophenyl)-4-methyl-1H-1,2,3-triazol-5-yl)methoxy)-2-isopropyl-1H-pyrrolo[3,4-c]pyridin-3(2H)-one

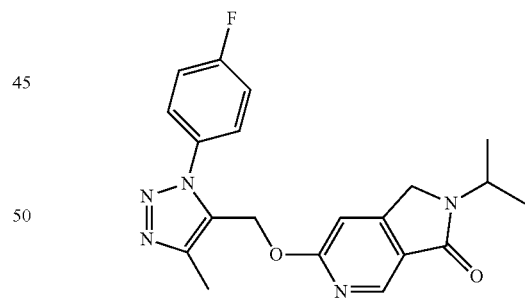

To a solution of [3-(4-fluoro-phenyl)-5-methyl-3H-[1,2,3]triazol-4-yl]-methanol (251 mg, 1.21 mmol) in THF (30 mL) was added 6-hydroxy-2-isopropyl-1H-pyrrolo[3,4-c]pyridin-3(2H)-one (232 mg, 1.21 mmol) and triphenylphosphine (413 mg, 1.58 mmol) at ambient temperature under an argon atmosphere. Then diethyl azodicarboxylate (624 μL, 1.58 mmol) was added and the reaction mixture was stirred for 72 h at room temperature. Concentration and purification by chromatography (silica, 20 to 50% ethyl acetate in heptane) afforded the title compound (141 mg, 31%) as a white solid. MS: m/e=382.2 [M+H]$^+$.

Example 80

5-[3-(4-Fluoro-phenyl)-5-methyl-3H-[1,2,3]triazol-4-ylmethoxy]-pyrazine-2-carboxylic acid (tetrahydro-pyran-4-yl)-amide

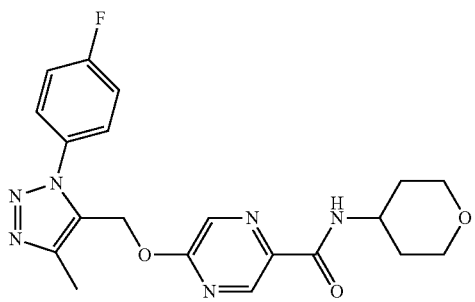 [SMILES: Cc1nnn(-c2ccc(F)cc2)c1COc1cnc(C(=O)NC2CCOCC2)cn1]

a) 5-[3-(4-Fluoro-phenyl)-5-methyl-3H-[1,2,3]-triazol-4-ylmethoxy]-pyrazine-2-carboxylic acid methyl ester To a suspension of NaH (55% in oil, 116 mg, 2.7 mmol) in THF (4 mL) was added a solution of [3-(4-fluoro-phenyl)-5-methyl-3H-[1,2,3]triazol-4-yl]-methanol (500 mg, 2.4 mmol) in THF (6 mL) dropwise at 0° C. and the reaction mixture was stirred at room temperature for 30 min. Then a solution of methyl 5-chloropyrazine-2-carboxylate (460 mg, 2.65 mmol) in THF (6 mL) was added dropwise at 0° C. and the reaction mixture was stirred at room temperature for 16 h. The mixture was then poured into ice water and extracted with ethyl acetate and the combined organic extracts washed with brine, dried over sodium sulphate, filtered and evaporated. Purification by chromatography (silica, 0 to 50% ethyl acetate in heptane, then 0 to 5% methanol in dichloromethane) afforded the title compound (787 mg, 95%) as a white solid. MS: m/e=344.3 [M+H]$^+$.

b) 5-[3-(4-Fluoro-phenyl)-5-methyl-3H-[1,2,3]triazol-4-ylmethoxy]-pyrazine-2-carboxylic acid A solution of lithium hydroxide monohydrate (180 mg, 4.25 mmol) in water (7.3 mL) was added dropwise to a suspension of 5-[3-(4-fluoro-phenyl)-5-methyl-3H-[1,2,3]triazol-4-ylmethoxy]-pyrazine-2-carboxylic acid methyl ester (730 mg, 2.13 mmol) in THF (7.3 mL). The reaction mixture was then stirred at room temperature for 30 min and was then evaporated and the residue dissolved in water, acidified with HCl (1N), and the resulting precipitate filtered off to afford the title product (700 mg, 100%) as a white solid. MS: m/e=330.1 [M−H]$^-$.

c) 5-[3-(4-Fluoro-phenyl)-5-methyl-3H-[1,2,3]triazol-4-ylmethoxy]-pyrazine-2-carboxylic acid (tetrahydro-pyran-4-yl)-amide To a solution of 5-[3-(4-fluoro-phenyl)-5-methyl-3H-[1,2,3]triazol-4-ylmethoxy]-pyrazine-2-carboxylic acid (83 mg, 0.25 mmol) and TBTU (90 mg, 0.28 mmol) in DMF (3.0 mL) was added DIPEA (216 μL, 1.26 mmol). Then 4-aminotetrahydropyran (28 mg, 0.28 mmol) was added and the mixture was stirred at room temperature under Ar for 30 min. The mixture was then evaporated and purification by chromatography (silica, 50 to 100% ethyl acetate in heptane) afforded the title compound (92 mg, 89%) as a white solid. MS: m/e=413.3 [M+H]$^+$.

Example 81

5-[3-(4-Fluoro-phenyl)-5-methyl-3H-[1,2,3]triazol-4-ylmethoxy]-pyrazine-2-carboxylic acid isopropylamide

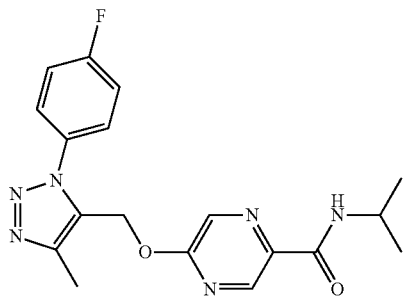 [SMILES: Cc1nnn(-c2ccc(F)cc2)c1COc1cnc(C(=O)NC(C)C)cn1]

As described for example 80c, 5-[3-(4-fluoro-phenyl)-5-methyl-3H-[1,2,3]triazol-4-ylmethoxy]-pyrazine-2-carboxylic acid (83 mg, 0.25 mmol), was converted, using isopropylamine instead of 4-aminotetrahydropyran, to the title compound (90 mg, 96%) which was obtained as an off white solid. MS: m/e=371.1 [M+H]$^+$.

Example 82

5-[3-(4-Fluoro-phenyl)-5-methyl-3H-[1,2,3]triazol-4-ylmethoxy]-pyrazine-2-carboxylic acid (2-hydroxy-1,1-dimethyl-ethyl)-amide

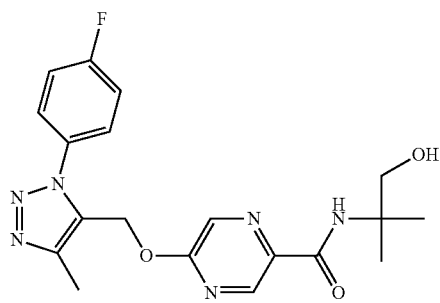 [SMILES: Cc1nnn(-c2ccc(F)cc2)c1COc1cnc(C(=O)NC(C)(C)CO)cn1]

As described for example 80c, 5-[3-(4-fluoro-phenyl)-5-methyl-3H-[1,2,3]triazol-4-ylmethoxy]-pyrazine-2-carboxylic acid (83 mg, 0.25 mmol), was converted, using 2-amino-2-methyl-1-propanol instead of 4-aminotetrahydropyran, to the title compound (95 mg, 94%) which was obtained as a light yellow gum. MS: m/e=401.3 [M+H]$^+$.

Example 83

5-[3-(4-Fluoro-phenyl)-5-methyl-3H-[1,2,3]triazol-4-ylmethoxy]-pyrazine-2-carboxylic acid morpholin-4-ylamide

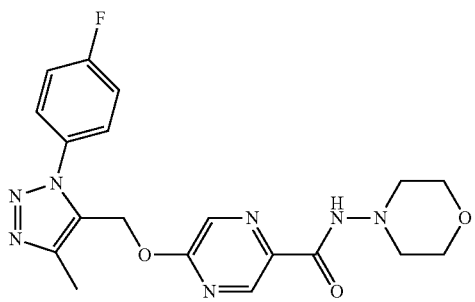 [SMILES: Cc1nnn(-c2ccc(F)cc2)c1COc1cnc(C(=O)NN2CCOCC2)cn1]

As described for example 80c, 5-[3-(4-fluoro-phenyl)-5-methyl-3H-[1,2,3]triazol-4-ylmethoxy]-pyrazine-2-carboxylic acid (83 mg, 0.25 mmol), was converted, using 4-aminomorpholine instead of 4-aminotetrahydropyran, to the title compound (62 mg, 60%) which was obtained as a white solid. MS: m/e=414.4 [M+H]$^+$.

Example 84

5-[3-(4-Fluoro-phenyl)-5-methyl-3H-[1,2,3]triazol-4-ylmethoxy]-pyrazine-2-carboxylic acid (3-methyl-oxetan-3-yl)-amide

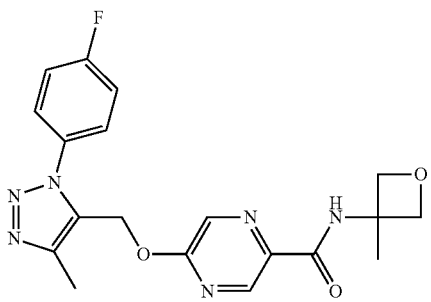 [SMILES: Cc1nnn(-c2ccc(F)cc2)c1COc1cnc(C(=O)NC2(C)COC2)cn1]

As described for example 80c, 5-[3-(4-fluoro-phenyl)-5-methyl-3H-[1,2,3]triazol-4-ylmethoxy]-pyrazine-2-carboxylic acid (83 mg, 0.25 mmol), was converted, using 3-methyl-3-oxetanamine instead of 4-aminotetrahydropyran, to the title compound (63 mg, 63%) which was obtained as an off white solid. MS: m/e=399.2 [M+H]$^+$.

Biochemical Assay

The ability of compounds present invention to bind to GABA A receptor subtypes was determined by competition for [$^3$H]flumazenil (85 Ci/mmol; Roche) binding to HEK293 cells expressing rat (stably transfected) or human (transiently transfected) receptors of composition α1β2/3γ2, α2β3γ2, α3β3γ2 and α5β3γ2.

Membrane Preparation

Cell pellets were suspended in Krebs-tris buffer (4.8 mM KCl, 1.2 mM CaCl$_2$, 1.2 mM MgCl$_2$, 120 mM NaCl, 15 mM Tris; pH 7.5; binding assay buffer), homogenized by polytron for ca. 20 sec on ice and centrifuged for 60 min at 4° C. (50000 g; Sorvall, rotor: SM24=20000 rpm). The cell pellets were resuspended in Krebs-tris buffer and homogenized by polytron for ca. 15 sec on ice. Protein was measured (Bradford method, Bio-Rad) and aliquots of 1 mL were prepared and stored at −80° C.

Radioligand Binding Assay

Radioligand binding assays were carried out in a volume of 200 mL (96-well plates) which contained 100 mL of cell membranes, [$^3$H]flumazenil at a concentration of 1 nM for α1, α2, α3 subunits and 0.5 nM for α5 subunits and the test compound in the range of 10-10$^{-3}$×10$^{-6}$ M. Nonspecific binding was defined by 10$^{-5}$ M diazepam and typically represented less than 5% of the total binding. Assays were incubated to equilibrium for 1 hour at 4° C. and harvested onto GF/C uni-filters (Packard) by filtration using a Packard harvester and washing with ice-cold wash buffer (50 mM Tris; pH 7.5). After drying, filter-retained radioactivity was detected by liquid scintillation counting.

Data Calculation

K$_i$ values were calculated using Excel-Fit (Microsoft) and are the means of two determinations. The compounds of the accompanying examples were tested in the above described assay, and the particular compounds were found to possess a K$_i$ value for displacement of [$^3$H]flumazenil from α5 subunits of the rat GABA A receptor of 100 nM or less. A particular embodiment embraces compounds with a K$_i$ of 35 nM or less. In a particular embodiment the compounds of the invention are binding selectively for the α5 subunit relative to the α1, α2 and α3 subunit.

The invention claimed is:

1. A compound of formula (I)

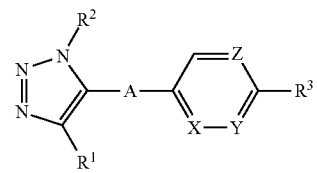

(I)

wherein

A is —CH$_2$—O—; wherein X is N, Y is CR$^9$ and Z is CR$^{10}$, or X is CH, Y is N and Z is CR$^{10}$; or X is N, Y is CR$^9$ and Z is N; or X is N, Y is N and Z is CR$^{10}$;

R$^1$ and R$^2$ are each independently alkyl, aryl optionally substituted by one halo or heteroaryl optionally substituted by one halo, wherein one of R$^1$ or R$^2$ is alkyl;

R$^3$ is halo, haloalkyl, —C(O)R$^4$, or —C(O)NR$^5$R$^6$;

R$^4$ is alkoxy;

R$^5$ is alkyl, haloalkyl, hydroxyalkyl, halohydroxyalkyl, —(CH$_2$)$_n$-cycloalkyl, —(CH$_2$)$_n$-heterocycloalkyl, or —(CH$_2$)$_n$—NR$^7$R$^8$, wherein said heterocycloalkyl is optionally substituted by one or two alkyl or oxo;

R$^6$ is H, alkyl, or is alkylene together with R$^9$ or R$^{10}$;

or R$^5$ and R$^6$ together with the nitrogen to which they are bound form a heterocycloalkyl optionally substituted by one or more oxo;

R$^7$ and R$^8$ are each independently alkyl;

R$^9$ and R$^{10}$ are each independently H, or one of R$^9$ or R$^{10}$ is alkylene together with R$^6$; and n is an integer from 0 to 1;

or a pharmaceutically acceptable salt or ester thereof.

2. The compound of claim 1, wherein $R^3$ is —C(O)NR$^5$R$^6$.

3. The compound of claim 1, wherein $R^3$ is —C(O)R$^4$, and $R^4$ is alkoxy.

4. The compound of claim 1, wherein $R^5$ is alkyl, haloalkyl, hydroxyalkyl, halohydroxyalkyl, cycloalkylmethyl, cycloalkyl, heterocycloalkyl, heterocycloalkyl substituted by alkyl, or N(alkyl)$_2$.

5. The compound of claim 1, wherein $R^5$ is iso-propyl, trifluoro-ethyl, hydroxy-ethyl, 2-hydroxy-1,1-dimethyl-ethyl, 3,3,3-trifluoro-2-hydroxy-propyl, cyclopropyl-methyl, cyclopropyl, methyl-oxetanyl, dioxo-tetrahydro-thiophenyl, tetrahydro-pyranyl, morpholinyl, or N(CH$_3$)$_2$.

6. The compound of claim 1, wherein $R^6$ is H.

7. The compound of claim 1, wherein $R^5$ and $R^6$ together with the nitrogen to which they are bound form a heterocycloalkyl optionally substituted by one or two oxo.

8. The compound of claim 1, wherein $R^5$ and $R^6$ together with the nitrogen to which they are bound form dioxo-thiomorpholinyl or 2-oxa-6-azaspiro[3.3]heptan-6-yl.

9. The compound of claim 1, wherein $R^6$ together with $R^{10}$ is alkylene.

10. The compound of claim 1, selected from the group consisting of:
N-Isopropyl-6-(3-methyl-5-phenyl-3H-[1,2,3]triazol-4-ylmethoxy)-nicotinamide;
6-(3-Methyl-5-phenyl-3H-[1,2,3]triazol-4-ylmethoxy)-N-(tetrahydro-pyran-4-yl)-nicotinamide;
6-(3-Methyl-5-phenyl-3H-[1,2,3]triazol-4-ylmethoxy)-N-morpholin-4-yl-nicotinamide;
N-Cyclopropyl-6-(3-methyl-5-phenyl-3H-[1,2,3]triazol-4-ylmethoxy)-nicotinamide;
N-Cyclopropylmethyl-6-(3-methyl-5-phenyl-3H-[1,2,3]triazol-4-ylmethoxy)-nicotinamide;
N-(1,1-Dioxo-tetrahydro-1,6-thiophen-3-yl)-6-(3-methyl-5-phenyl-3H-[1,2,3]triazol-4-ylmethoxy)-nicotinamide;
6-(3-Methyl-5-phenyl-3H-[1,2,3]triazol-4-ylmethoxy)-N-(2,2,2-trifluoro-ethyl)-nicotinamide;
N-(2-Hydroxy-ethyl)-6-(3-methyl-5-phenyl-3H-[1,2,3]triazol-4-ylmethoxy)-nicotinamide;
6-[5-(4-Fluoro-phenyl)-3-methyl-3H-[1,2,3]triazol-4-ylmethoxy]-nicotinic acid methyl ester; and
6-[5-(4-Fluoro-phenyl)-3-methyl-3H-[1,2,3]triazol-4-ylmethoxy]-N-(tetrahydro-pyran-4-ye-nicotinamide;
or a pharmaceutically acceptable salt or ester thereof.

11. The compound of claim 1, selected from the group consisting of:
6-[5-(4-Fluoro-phenyl)-3-methyl-3H-[1,2,3]triazol-4-ylmethoxy]-N-isopropyl-nicotinamide;
6-[5-(4-Fluoro-phenyl)-3-methyl-3H-[1,2,3]triazol-4-ylmethoxy]-N-(2-hydroxy-1,1-dimethyl-ethyl)-nicotinamide;
6-[5-(4-Fluoro-phenyl)-3-methyl-3H-[1,2,3]triazol-4-ylmethoxy]-N-(3-methyl-oxetan-3-yl)-nicotinamide;
6-[5-(4-Fluoro-phenyl)-3-methyl-3H-[1,2,3]triazol-4-ylmethoxy]-N-morpholin-4-yl-nicotinamide;
6-[5-(4-Fluoro-phenyl)-3-methyl-3H-[1,2,3]triazol-4-ylmethoxy]-N-(3,3,3-trifluoro-2-hydroxy-propyl)-nicotinamide;
6-[5-(4-Fluoro-phenyl)-3-methyl-3H-[1,2,3]triazol-4-ylmethoxy]-N-(2-hydroxy-ethyl)-nicotinamide;
6-((4-(4-Fluorophenyl)-1-methyl-1H-1,2,3-triazol-5-yl)methoxy)-2-isopropyl-1H-pyrrolo[3,4-c]pyridin-3(2H)-one;
Methyl 6-((4-(2-fluorophenyl)-1-methyl-1H-1,2,3-triazol-5-yl)methoxy)nicotinate;
6-((4-(2-Fluorophenyl)-1-methyl-1H-1,2,3-triazol-5-yl)methoxy)-N-(tetrahydro-2H-pyran-4-yl)nicotinamide; and
6-((4-(2-Fluorophenyl)-1-methyl-1H-1,2,3-triazol-5-yl)methoxy)-N-isopropylnicotinamide;
or a pharmaceutically acceptable salt or ester thereof.

12. The compound of claim 1, selected from the group consisting of:
6-((4-(2-Fluorophenyl)-1-methyl-1H-1,2,3-triazol-5-yl)methoxy)-N-(3-methyloxetan-3-yl)nicotinamide;
(1,1-Dioxo-1,6-thiomorpholin-4-yl)-{6-[5-(2-fluoro-phenyl)-3-methyl-3H-[1,2,3]triazol-4-ylmethoxy]-pyridin-3-yl}-methanone;
(6-((4-(2-Fluorophenyl)-1-methyl-1H-1,2,3-triazol-5-yl)methoxy)pyridin-3-yl)(2-oxa-6-azaspiro[3.3]heptan-6-yl)methanone;
6-((4-(2-Fluorophenyl)-1-methyl-1H-1,2,3-triazol-5-yl)methoxy)-N-morpholinonicotinamide;
6-(3-Methyl-5-pyridin-2-yl-3H-[1,2,3]triazol-4-ylmethoxy)-nicotinic acid methyl ester;
6-(3-Methyl-5-pyridin-2-yl-3H-[1,2,3]triazol-4-ylmethoxy)-N-(tetrahydro-pyran-4-yl)-nicotinamide;
N-Isopropyl-6-(3-methyl-5-pyridin-2-yl-3H-[1,2,3]triazol-4-ylmethoxy)-nicotinamide;
N-(2-Hydroxy-1,1-dimethyl-ethyl)-6-(3-methyl-5-pyridin-2-yl-3H-[1,2,3]triazol-4-ylmethoxy)-nicotinamide;
N-(2-Hydroxy-ethyl)-6-(3-methyl-5-pyridin-2-yl-3H-[1,2,3]triazol-4-ylmethoxy)-nicotinamide; and
N-(3-Methyl-oxetan-3-yl)-6-(3-methyl-5-pyridin-2-yl-3H-[1,2,3]triazol-4-ylmethoxy)-nicotinamide;
or a pharmaceutically acceptable salt or ester thereof.

13. The compound of claim 1, selected from the group consisting of:
6-(3-Methyl-5-pyridin-2-yl-3H-[1,2,3]triazol-4-ylmethoxy)-N-morpholin-4-yl-nicotinamide;
6-(3-Methyl-5-pyridin-2-yl-3H-[1,2,3]triazol-4-ylmethoxy)-nicotinic acid N,N'-dimethyl-hydrazide;
6-(3-Methyl-5-pyridin-2-yl-3H-[1,2,3]triazol-4-ylmethoxy)-N-(3,3,3-trifluoro-2-hydroxy-propyl)-nicotinamide;
6-[5-(5-Fluoro-pyridin-2-yl)-3-methyl-3H-[1,2,3]triazol-4-ylmethoxy]-nicotinic acid methyl ester;
6-[5-(5-Fluoro-pyridin-2-yl)-3-methyl-3H-[1,2,3]triazol-4-ylmethoxy]-N-(tetrahydro-pyran-4-yl)-nicotinamide;
6-[5-(5-Fluoro-pyridin-2-yl)-3-methyl-3H-[1,2,3]triazol-4-ylmethoxy] isopropyl-nicotinamide;
6-[5-(5-Fluoro-pyridin-2-yl)-3-methyl-3H-[1,2,3]triazol-4-ylmethoxy]-N-(2-hydroxy-1,1-dimethyl-ethyl)-nicotinamide;
6-[5-(5-Fluoro-pyridin-2-yl)-3-methyl-3H-[1,2,3]triazol-4-ylmethoxy]-N-(3-methyl-oxetan-3-yl)-nicotinamide;
6-[5-(5-Fluoro-pyridin-2-yl)-3-methyl-3H-[1,2,3]triazol-4-ylmethoxy]-N-morpholin-4-yl-nicotinamide; and
5-[5-(5-Fluoro-pyridin-2-yl)-3-methyl-3H-[1,2,3]triazol-4-ylmethoxy]-pyridine-2-carboxylic acid isopropylamide;
or a pharmaceutically acceptable salt or ester thereof.

14. The compound of claim 1, selected from the group consisting of:
6-[5-(4-Fluoro-phenyl)-3-methyl-3H-[1,2,3]triazol-4-ylmethoxy]-pyridazine-3-carboxylic acid ethyl ester;
6-[5-(4-Fluoro-phenyl)-3-methyl-3H-[1,2,3]triazol-4-ylmethoxy]-pyridazine-3-carboxylic acid (tetrahydro-pyran-4-yl)-amide;
6-[5-(4-Fluoro-phenyl)-3-methyl-3H-[1,2,3]triazol-4-ylmethoxy]-pyridazine-3-carboxylic acid isopropylamide;

6-[5-(4-Fluoro-phenyl)-3-methyl-3H-[1,2,3]triazol-4-yl-methoxy-3-pyridazine-3-carboxylic acid (2-hydroxy-1,1-dimethyl-ethyl)-amide;
6-[5-(4-Fluoro-phenyl)-3-methyl-3H-[1,2,3]triazol-4-yl-methoxy]-pyridazine-3-carboxylic acid morpholin-4-ylamide;
3-Chloro-6-(3-methyl-5-pyridin-2-yl-3H-[1,2,3]triazol-4-ylmethoxy)-pyridazine;
6-(3-Methyl-5-pyridin-2-yl-3H-[1,2,3]triazol-4-yl-methoxy)-pyridazine-3-carboxylic acid ethyl ester;
6-(3-Methyl-5-pyridin-2-yl-3H-[1,2,3]triazol-4-yl-methoxy)-pyridazine-3-carboxylic acid (tetrahydro-pyran-4-yl)-amide;
6-(3-Methyl-5-pyridin-2-yl-3H-[1,2,3]triazol-4-yl-methoxy)-pyridazine-3-carboxylic acid isopropylamide; and
3-Chloro-6-[5-(5-fluoro-pyridin-2-yl)-3-methyl-3H-[1,2,3]triazol-4-ylmethoxy]-pyridazine;
or a pharmaceutically acceptable salt or ester thereof.

15. The compound of claim 1, selected from the group consisting of:
  6-[5-(5-Fluoro-pyridin-2-yl)-3-methyl-3H-[1,2,3]triazol-4-ylmethoxy]-pyridazine-3-carboxylic acid (2-hydroxy-1,1-dimethyl-ethyl)-amide;
  6-[5-(5-Fluoro-pyridin-2-yl)-3-methyl-3H-[1,2,3]triazol-4-ylmethoxy]-pyridazine-3-carboxylic acid morpholin-4-ylamide;
  5-[5-(4-Fluoro-phenyl)-3-methyl-3H-[1,2,3]triazol-4-ylmethoxy]-pyrazine-2-carboxylic acid isopropylamide;
  5-[5-(4-Fluoro-phenyl)-3-methyl-3H-[1,2,3]triazol-4-yl-methoxy]-pyrazine-2-carboxylic acid (tetrahydro-pyran-4-yl)-amide; and
  6-[3-(4-Fluoro-phenyl)-5-methyl-3H-[1,2,3]triazol-4-yl-methoxy]-nicotinic acid methyl ester;
  or a pharmaceutically acceptable salt or ester thereof.

16. The compound of claim 1, selected from the group consisting of:
  6-[3-(4-Fluoro-phenyl)-5-methyl-3H-[1,2,3]triazol-4-yl-methoxy]-N-(tetrahydro-pyran-4-yl)-nicotinamide;
  6-[3-(4-Fluoro-phenyl)-5-methyl-3H-[1,2,3]triazol-4-yl-methoxy]-N-isopropyl-nicotinamide;
  6-[3-(4-Fluoro-phenyl)-5-methyl-3H-[1,2,3]triazol-4-yl-methoxy]-N-(2-hydroxy-1,1-dimethyl-ethyl)-nicotinamide;
  6-[3-(4-Fluoro-phenyl)-5-methyl-3H-[1,2,3]triazol-4-yl-methoxy]-N-morpholin-4-yl-nicotinamide;
  6-[3-(4-Fluoro-phenyl)-5-methyl-3H-[1,2,3]triazol-4-yl-methoxy]-N-(3-methyl-oxetan-3-yl)-nicotinamide;
  Methyl 6-((1-(2-fluorophenyl)-4-methyl-1H-1,2,3-triazol-5-yl)methoxy)nicotinate;
  6-((1-(2-Fluorophenyl)-4-methyl-1H-1,2,3-triazol-5-yl)methoxy)-N-isopropylnicotinamide;
  6-((1-(2-Fluorophenyl)-4-methyl-1H-1,2,3-triazol-5-yl)methoxy)-N-(tetrahydro-2H-pyran-4-yl)nicotinamide;
  6-((1-(2-Fluorophenyl)-4-methyl-1H-1,2,3-triazol-5-yl)methoxy)-N-(3-methyloxetan-3-yl)nicotinamide; and
  6-((1-(2-Fluorophenyl)-4-methyl-1H-1,2,3-triazol-5-yl)methoxy)-N-morpholinonicotinamide;
  or a pharmaceutically acceptable salt or ester thereof.

17. The compound of claim 1, selected from the group consisting of:
  N-Cyclopropyl-6-((1-(2-fluorophenyl)-4-methyl-1H-1,2,3-triazol-5-yl)methoxy)nicotinamide;
  N-(Cyclopropylmethyl)-6-((1-(2-fluorophenyl)-4-methyl-1H-1,2,3-triazol-5-yl)methoxy)nicotinamide;
  3-Chloro-6-[3-(4-fluoro-phenyl)-5-methyl-3H-[1,2,3]triazol-4-ylmethoxy]-pyridazine;
  6-[3-(4-Fluoro-phenyl)-5-methyl-3H-[1,2,3]triazol-4-yl-methoxy]-pyridazine-3-carboxylic acid ethyl ester;
  6-[3-(4-Fluoro-phenyl)-5-methyl-3H-[1,2,3]triazol-4-yl-methoxy]-pyridazine-3-carboxylic acid isopropylamide;
  6-[3-(4-Fluoro-phenyl)-5-methyl-3H-[1,2,3]triazol-4-yl-methoxy]-pyridazine-3-carboxylic acid morpholin-4-ylamide;
  6-[3-(4-Fluoro-phenyl)-5-methyl-3H-[1,2,3]triazol-4-yl-methoxy]-pyridazine-3-carboxylic acid (3-methyl-oxetan-3-yl)-amide;
  6-[3-(4-Fluoro-phenyl)-5-methyl-3H-[1,2,3]triazol-4-yl-methoxy]-pyridazine-3-carboxylic acid (tetrahydro-pyran-4-yl)-amide;
  6-((1-(4-Fluorophenyl)-4-methyl-1H-1,2,3-triazol-5-yl)methoxy)-2-isopropyl-1H-pyrrolo[3,4-c]pyridin-3(2H)-one; and
  5-[3-(4-Fluoro-phenyl)-5-methyl-3H-[1,2,3]triazol-4-yl-methoxy]-pyrazine-2-carboxylic acid (tetrahydro-pyran-4-yl)-amide;
  or a pharmaceutically acceptable salt or ester thereof.

18. The compound of claim 1, selected from the group consisting of:
  5-[3-(4-Fluoro-phenyl)-5-methyl-3H-[1,2,3]triazol-4-yl-methoxy]-pyrazine-2-carboxylic acid isopropylamide;
  5-[3-(4-Fluoro-phenyl)-5-methyl-3H-[1,2,3]triazol-4-yl-methoxy]-pyrazine-2-carboxylic acid (2-hydroxy-1,1-dimethyl-ethyl)-amide;
  5-[3-(4-Fluoro-phenyl)-5-methyl-3H-[1,2,3]triazol-4-yl-methoxy]-pyrazine-2-carboxylic acid morpholin-4-ylamide; and
  5-[3-(4-Fluoro-phenyl)-5-methyl-3H-[1,2,3]triazol-4-yl-methoxy]-pyrazine-2-carboxylic acid (3-methyl-oxetan-3-yl)-amide;
  or a pharmaceutically acceptable salt or ester thereof.

19. The compound of claim 1, selected from the group consisting of:
  N-Cyclopropyl-6-(3-methyl-5-phenyl-3H-[1,2,3]triazol-4-ylmethoxy)-nicotinamide;
  6-[5-(4-Fluoro-phenyl)-3-methyl-3H-[1,2,3]triazol-4-yl-methoxy]-N-isopropyl-nicotinamide;
  6-[5-(4-Fluoro-phenyl)-3-methyl-3H-[1,2,3]triazol-4-yl-methoxy]-N-morpholin-4-yl-nicotinamide;
  N-(2-Hydroxy-1,1-dimethyl-ethyl)-6-(3-methyl-5-pyridin-2-yl-3H-[1,2,3]triazol-4-ylmethoxy)-nicotinamide;
  6-(3-Methyl-5-pyridin-2-yl-3H-[1,2,3]triazol-4-yl-methoxy)-nicotinic acid N,N'-dimethyl-hydrazide;
  6-[5-(5-Fluoro-pyridin-2-yl)-3-methyl-3H-[1,2,3]triazol-4-ylmethoxy]-N-(2-hydroxy-1,1-dimethyl-ethyl)-nicotinamide;
  6-[5-(5-Fluoro-pyridin-2-yl)-3-methyl-3H-[1,2,3]triazol-4-ylmethoxy]-N-morpholin-4-yl-nicotinamide;
  6-[3-(4-Fluoro-phenyl)-5-methyl-3H-[1,2,3]triazol-4-yl-methoxy]-N-(2-hydroxy-1,1-dimethyl-ethyl)-nicotinamide;
  6-[3-(4-Fluoro-phenyl)-5-methyl-3H-[1,2,3]triazol-4-yl-methoxy]-N-(3-methyl-oxetan-3-yl)-nicotinamide;
  6-((1-(2-Fluorophenyl)-4-methyl-1H-1,2,3-triazol-5-yl)methoxy)-N-(tetrahydro-2H-pyran-4-yl)nicotinamide; and
  6-((1-(2-Fluorophenyl)-4-methyl-1H-1,2,3-triazol-5-yl)methoxy)-N-(3-methyloxetan-3-yl)nicotinamide; or
  a pharmaceutically acceptable salt or ester thereof.

* * * * *